(12) United States Patent
Becker-Pelster et al.

(10) Patent No.: US 9,624,199 B2
(45) Date of Patent: Apr. 18, 2017

(54) SUBSTITUTED BIPIPERIDINYL DERIVATIVES

(71) Applicant: Bayer Pharma Aktiengesellschaft, Berlin (DE)

(72) Inventors: Eva Maria Becker-Pelster, Wuppertal (DE); Philipp Buchgraber, Berlin (DE); Anja Buchmüller, Essen (DE); Karen Engel, Roβdorf (DE); Andreas Göller, Wuppertal (DE); Herbert Himmel, Essen (DE); Raimund Kast, Wuppertal (DE); Joerg Keldenich, Berlin (DE); Carsten Schmeck, Mülheim (DE); Hanna Tinel, Wuppertal (DE); Frank Wunder, Wuppertal (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/106,286

(22) PCT Filed: Dec. 16, 2014

(86) PCT No.: PCT/EP2014/077868
§ 371 (c)(1),
(2) Date: Jun. 18, 2016

(87) PCT Pub. No.: WO2015/091420
PCT Pub. Date: Jun. 25, 2015

(65) Prior Publication Data
US 2016/0304492 A1 Oct. 20, 2016

(30) Foreign Application Priority Data

Dec. 19, 2013 (EP) .................................... 13198387
Nov. 12, 2014 (EP) .................................... 14192879

(51) Int. Cl.
| | | |
|---|---|---|
| *C07D 401/14* | (2006.01) | |
| *A61K 31/4545* | (2006.01) | |
| *A61K 31/506* | (2006.01) | |
| *A61K 31/541* | (2006.01) | |
| *A61K 45/06* | (2006.01) | |
| *A61K 31/5377* | (2006.01) | |
| *C07D 491/107* | (2006.01) | |

(52) U.S. Cl.
CPC ........ *C07D 401/14* (2013.01); *A61K 31/4545* (2013.01); *A61K 31/506* (2013.01); *A61K 31/5377* (2013.01); *A61K 31/541* (2013.01); *A61K 45/06* (2013.01); *C07D 491/107* (2013.01)

(58) Field of Classification Search
CPC .............. C07D 401/14; C07D 491/107; A61K 31/4545; A61K 31/506; A61K 31/5377; A61K 31/541; A61K 45/06

USPC ........................................................ 514/210.2
See application file for complete search history.

(56) References Cited

U.S. PATENT DOCUMENTS

| | | |
|---|---|---|
| 6,444,681 B1 | 9/2002 | Flavahan et al. |
| 6,495,555 B1 | 12/2002 | Kennis et al. |
| 2004/0010008 A1 | 1/2004 | Palani et al. |
| 2004/0092551 A1 | 5/2004 | Palani et al. |
| 2004/0092745 A1 | 5/2004 | Palani et al. |
| 2005/0182095 A1 | 8/2005 | Ting et al. |
| 2006/0025441 A1 | 2/2006 | Miller et al. |
| 2006/0223792 A1 | 10/2006 | Butler et al. |
| 2008/0214575 A1 | 9/2008 | Palani et al. |
| 2011/0262352 A1 | 10/2011 | Din Belle et al. |
| 2014/0023614 A1 | 1/2014 | Barawkar et al. |

FOREIGN PATENT DOCUMENTS

| | | |
|---|---|---|
| CA | 2371587 | 9/2005 |
| WO | 94/22826 | 10/1994 |
| WO | 97/26265 | 7/1997 |
| WO | 99/03861 | 1/1999 |
| WO | 00/06568 | 2/2000 |
| WO | 00/06569 | 2/2000 |
| WO | 00/66559 | 11/2000 |
| WO | 01/19355 | 3/2001 |
| WO | 01/19776 | 3/2001 |
| WO | 01/19780 | 3/2001 |
| WO | 01/19778 | 3/2002 |

(Continued)

OTHER PUBLICATIONS

European Patent Office, International Search Report and Written Opinion received for International Patent Application No. PCT/EP2014/077868, Jun. 25, 2015, 31 pages.

(Continued)

*Primary Examiner* — Yevegeny Valenrod
(74) *Attorney, Agent, or Firm* — Aseem Mehta

(57) ABSTRACT

The invention relates to novel substituted bipiperidinyl derivatives, to processes for their preparation, to their use for the treatment and/or prevention of diseases and to their use for preparing medicaments for the treatment and/or prevention of diseases, in particular for the treatment and/or prevention of diabetic microangiopathies, diabetic ulcers on the extremities, in particular for promoting wound healing of diabetic foot ulcers, diabetic heart failure, diabetic coronary microvascular heart disorders, peripheral and cardial vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies.

19 Claims, No Drawings

(56) References Cited

FOREIGN PATENT DOCUMENTS

| WO | 02/42301 | 5/2002 |
|---|---|---|
| WO | 02/070462 | 9/2002 |
| WO | 02/070510 | 9/2002 |
| WO | 02/081449 | 10/2002 |
| WO | 03/020716 | 3/2003 |
| WO | 03/095451 | 11/2003 |
| WO | 2004/067513 | 8/2004 |
| WO | 2005/042517 | 5/2005 |
| WO | 2005/077369 | 8/2005 |
| WO | 2010/058060 | 5/2010 |
| WO | 2012/127506 | 9/2012 |

OTHER PUBLICATIONS

Chotani, et al., "Distinct cAMP signaling pathways differentially regulate alpha2C adrenenoxceptor expression: role in serum induction in human arteriolar smooth muscle cells", Am J Physiol Heart Circ Physiol 288, 2005, pp. H69-H76.

Chotani, et al., "Silent alpha2C adrenergic receptors enable cold-induced vasoconstriction in cutaneous arteries", Am J Heart Circ Physiol 278, 2000, pp. H1075-H1083.

Cryan, et al., "Assessing antidepressant activity in rodents: recent developments and future needs", Trends Pharmacol. Sci. 23, 2002, pp. 238-245.

De Vry, et al., "Comparison of hypericum extracts with imipramine and fluoxetine in animal models of depression and alcoholism", Eur. Neuropsychopharmacology 9, 1999, pp. 461-468.

Gyires, et al., "alpha2-Adrenoceptor subtypes-mediated physiological, pharmacological actions", Neurochemistry International 55, 2009, pp. 447-453.

International Bureau of WIPO, International Preliminary Report on Patentability for International Patent Application No. PCT/EP2014/077868, Jun. 21, 2016, 10 pages.

Kanagy, "alpha2-Adrenergic receptor signalling in hypertension", Clinical Science 109, 2005, pp. 431-437.

Keenan, et al., "alpha2-Adrenergic receptors in platelets from patients with Raynaud'syndrome", Surgery, V94(2), 1983, 6 pages.

Porsolt, et al., "Behavioural despair in rats: a new model sensitive to antidepressant treatments", European Journal of Pharmacology, 47, 1978, pp. 379-391.

Porsolt, et al., "Rodent models of depression: forced swimming and tail suspension behavioral despair tests in rats and mice", Current Protocols in Neuroscience, Chapter 8:Unit 8.10A, 2001, pp. 1-10.

Tan, et al., "The alpha2-Adrenergic Receptors", The Receptors: Adrenergic Receptors in the 21st Century, 2005, pp. 241-265.

Vogelsberger, "Neue Tiermodelle für die Indikation Claudicatio Intermittens", [Novel animal models for the indication intermittent claudication] (pocket book), publisher: VVB Laufersweiler Verlag ISBN-10: 383595007X, ISBN-13: 978-3835950078, Mar. 2006, 29 pages.

Witte, et al., "Experimental heart failure in rats: effects on cardiovascular circadian rhythms and on myocardial β-adrenergic signaling", Cardiovasc. Res. 47(2), 2000, pp. 203-405.

Wuitschik, et al., "Spirocyclic Oxetanes: Synthesis and Properties", Angew. Chem. Int. Ed., 47, 2008, pp. 4512-4515.

Shirley et al., "Some Observations Pertaing to the Mechanism of Metalation of Aromatic Substrates with Alkyllithium Reagents", Journal of Organometallic Chemistry, 69, pp. 327-344, 1974.

Bujalska et al., "$\alpha_1$- and $\alpha_2$- Adrenoreceptor antagonists in streptozotocin- and vincristine-induced hyperalgesia," Pharmacological Reports, vol. 60, No. 4, Jul. 1, 2008, pp. 499-507, Institute of Pharmacology, Polish Academy of Sciences.

European Patent Office, International Search Report (with English translation) for International Patent Application No. PCT/EP2014/077865, Mar. 26, 2015, 7 pages.

European Patent Office, International Search Report (with English translation) for International Patent Application No. PCT/EP2014/077865, Jun. 25, 2015, 14 pages.

PCT International Search Report and Written Opinion received in PCT Application No. PCT/EP2014/077863 (Translations), Jun. 25, 2015, 32 pages.

European Patent Office, International Search Report (with English translation) for International Patent Application No. PCT/EP2014/077862, Jun. 26, 2015, 8 pages.

European Patent Office, Written Opinion (with English translation) for International Patent Application No. PCT/EP2014/077862, Jun. 30, 2015, 25 pages.

International Bureau Of WIPO, International Preliminary Report on Patentability for International Patent Application No. PCT/EP2014/077862, Jun. 21, 2016, 13 pages.

International Bureau Of WIPO, International Preliminary Report on Patentability for International Patent Application No. PCT/EP2014/077863, Jun. 21, 2016, 10 pages.

International Bureau Of WIPO, International Preliminary Report on Patentability for International Patent Application No. PCT/EP2014/077865, Jun. 21, 2016, 7 pages.

USPTO, Notice of Allowance for U.S. Appl. No. 15/106,283, Sep. 14, 2016, 28 pages.

USPTO, Notice of Allowance for U.S. Appl. No. 15/106,283, Dec. 22, 2016, 7 pages.

SUBSTITUTED BIPIPERIDINYL DERIVATIVES

CROSS-REFERENCE TO RELATED APPLICATIONS

This application is a U.S. national phase application of International Patent Application No. PCT/EP2014/077868, filed Dec. 16, 2014 and titled SUBSTITUTED BIPIPERIDINYL DERIVATIVES AS ADRENORECEPTOR ALPHA 2C ANTAGONISTS, which claims priority to both European Patent Application No. 13198387.6, filed Dec. 19, 2013 and titled SUBSTITUTED BIPIPERIDINYL DERIVATIVES AS ADRENORECEPTOR ALPHA 2C ANTAGONISTS, and European Patent Application No. 14192879.6, filed Nov. 12, 2014 and titled SUBSTITUTED BIPIPERIDINYL DERIVATIVES AS ADRENORECEPTOR ALPHA 2C ANTAGONISTS, the contents of all of which are incorporated herein by reference in their entirety.

The invention relates to novel substituted bipiperidinyl derivatives, to processes for their preparation, to their use in a method for the treatment and/or prophylaxis of diseases and to their use for preparing medicaments for the treatment and/or prophylaxis of diseases, in particular of cardiovascular disorders, diabetic microangiopathies, diabetic ulcers on the extremities, in particular for promoting wound healing of diabetic foot ulcers, diabetic heart failure, diabetic coronary microvascular heart disorders, peripheral and cardiac vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies.

Adrenoreceptor $\alpha_2$ receptors ($\alpha_2$-ARs) belong to the family of the G-protein-coupled receptors. They bind to the pertussis toxin-sensitive inhibitory G protein $G_i$ and $G_0$ and reduce adenylate cyclase activity. They are involved in the mediation of diverse physiological effects in various tissues following stimulation by endogenous catecholamines (adrenaline, noradrenaline) which are either released by synapses or reach the site of action via the blood. $\alpha_2$-AR play an important physiological role, mainly for the cardiovascular system, but also in the central nervous system. Biochemical, physiological and pharmacological studies have shown that, in addition to various a1-AR subtypes, there are three $\alpha_2$-AR subtypes ($\alpha_{2A}$, $\alpha_{2B}$ and $\alpha_{2C}$) in many target cells and tissues of cardiovascular relevance, which makes them attractive target proteins for therapeutic interventions. However, the elucidation of the precise physiological task of the receptor subtypes remains difficult because of a lack of highly selective ligands and/or antagonists of the respective $\alpha_2$-AR (Gyires et al., $\alpha_2$-Adrenoceptor subtypes-mediated physiological, pharmacological actions, Neurochemistry International 55, 447-453, 2009; Tan and Limbird, The $\alpha_2$-Adrenergic Receptors: Adrenergic Receptors in the 21st Century/Receptors, 2005, 241-265).

Cardiovascular changes such as, for example, the regulation of the contractility of the heart are regulated, firstly, by the central modulation of the sympathetic efferent nerves. Furthermore, the sympathetic efferent system also regulates direct effects on smooth muscle cells and the endothelial cells of the vessels. Thus, the sympathetic system is involved in the regulation of the output performance of the heart, but also in the control of local perfusion of various vascular beds. This is also controlled via $\alpha_2$-ARs involved in the regulation of the peripheral resistance. Thus, blood vessels are innervated by sympathetic nerve fibres which run in the adventitia and whose endings are provided with varicosities for the release of noradrenaline. Released noradrenaline modulates, via the $\alpha_2$-AR in endothelial cells and smooth muscle cells, the respective local vascular tone.

In addition to the effects on the sympathetic efferent nerves, the peripheral cardiovascular function is also regulated by pre- and postsynaptic $\alpha_2$-AR. Smooth muscle cells and endothelial cells express different $\alpha_2$-AR subtypes. The activation of $\alpha_{2A}$, $\alpha_{2B}$ and $\alpha_{2C}$ receptors on smooth muscle cells leads to contraction with resulting vasoconstriction (Kanagy, Clinical Science 109:431-437, 2005). However, the distribution of the respective receptor subtypes varies in the different vascular beds, between the species and between different vessel sizes. Thus, $\alpha_{2A}$-AR appear to be expressed virtually exclusively in large arteries, whereas $\alpha_{2B}$-AR contribute more to the vascular tone in small arteries and veins. AR$\alpha_{2B}$ appears to play a role in salt-induced hypertension (Gyires et al., $\alpha_2$-Adrenoceptor subtypes-mediated physiological, pharmacological actions, Neurochemistry International 55, 447-453, 2009). The role of AR$\alpha_{2C}$ on haemodynamics is not yet completely understood; however, AR$\alpha_{2C}$ receptors appear to mediate venous vasoconstriction. They are also involved in cold-induced enhancement of adrenoceptor-induced vasoconstriction (Chotani et al., Silent $\alpha_{2C}$ adrenergic receptors enable cold-induced vasoconstriction in cutaneous arteries. Am J Physiol 278:H1075-H1083, 2000; Gyires et al., $\alpha_2$-Adrenoceptor subtypes-mediated physiological, pharmacological actions, Neurochemistry International 55, 447-453, 2009). Cold and other factors (e.g. tissue proteins, oestrogen) regulate the functional coupling of AR$\alpha_{2C}$ to intracellular signal pathways (Chotani et al., Distinct cAMP signaling pathways differentially regulate $\alpha_{2C}$ adrenenoxceptor expression: role in serum induction in human arteriolar smooth muscle cells. Am J Physiol Heart Circ Physiol 288: H69-H76, 2005). For this reason, it makes sense to investigate selective inhibitors of AR-$\alpha_2$ subtypes for their perfusion-modulating effect on different vascular beds under different pathophysiological conditions.

Under pathophysiological conditions, the adrenergic system may be activated, which can lead, for example, to hypertension, heart failure, increased platelet activation, endothelial dysfunction, atherosclerosis, angina pectoris, myocardial infarction, thromboses, peripheral circulatory disturbances, stroke and sexual dysfunction. Thus, for example, the pathophysiology of Raynaud's syndrome and scleroderma is substantially unclear, but is associated with a changed adrenergic activity. Thus, patients suffering from spastic Raynaud's syndrome show, for example, a significantly elevated expression of AR$\alpha_2$ receptoren on their platelets. This may be connected with the vasospastic attacks observed in these patients (Keenan and Porter, $\alpha_2$-Adrenergic receptors in platelets from patients with Raynaud's syndrome, Surgery, V94(2), 1983).

By virtue of the expected high efficiency and low level of side effects, a possible treatment for such disorders targeting the modulation of the activated adrenergic system in organisms is a promising approach. In particular in diabetics, who frequently have elevated catecholamine levels, peripheral circulatory disturbances (microangiopathies) such as diabetic retinopathy, nephropathy or else pronounced wound healing disorders (diabetic foot ulcers) play a large role. In peripheral occlusive disease, diabetes mellitus is one of the most important comorbidities and also plays a crucial role in the progression of the disease (micro- and macroangiopathy). Higher expression of the adrenoreceptor $\alpha_{2C}$ receptors associated with elevated catecholamine levels may be involved in these pathophysiological processes in diabetics.

In 2011 there were 350 million diabetics worldwide (≈6.6% of the population), and this number is expected to double by 2028. Diabetic foot ulcers are the most frequent cause of hospitalizations of diabetics. The risk of a diabetic developing a diabetic foot ulcer in his or her lifetime is 15-25%, 15% of all diabetic foot ulcers lead to amputation. World-wide, 40-70% of all non-traumatic amputations are carried out on diabetics. Risk factors for diabetic foot ulcers are traumata, poor metabolic control, sensory, motoric and autonomous polyneuropathy, inappropriate footwear, infections and peripheral arterial disorders. The treatment of diabetic foot ulcers requires interdisciplinary teams and employs a multifactor approach: weight loss, revascularization (in the case of peripheral arterial occlusive disease, PAOD), improvements in metabolic control, wound excision, dressings, dalteparin, Regranex (PDGF) and amputation. The treatment costs per diabetic foot ulcer (without amputation) are 7000-10 000 USD. 33% of all diabetic foot ulcers do not heal within 2 years, and there is a high relapse rate (34% within the first year, 61% over 3 years).

Accordingly, it is an object of the present invention to provide novel selective adrenoreceptor $\alpha_{2C}$ receptor antagonists for the treatment and/or prophylaxis of diseases such as, for example, cardiovascular disorders, in humans and animals.

It is another object of the present invention to provide novel selective adrenoreceptor $\alpha_{2C}$ receptor antagonists for the treatment and/or prophylaxis of peripheal circulatory disturbances (microangiopathies) such as, for example, diabetic retinopathy, diabetic nephropathy and wound healing disorders (diabetic foot ulcers).

WO 2005/042517, WO 2003/020716, WO 2002/081449 and WO 2000/066559 describe structurally similar bipiperidinyl derivatives as inhibitors of the CCR5 receptor, inter alia for the treatment of HIV. WO 2005/077369 describes structurally similar bipiperidinyl derivatives as inhibitors of the CCR3 receptor, inter alia for the treatment of asthma. WO 94/22826 describes structurally similar piperidines as active compounds having peripheral vasodilating action. U.S. Pat. No. 6,444,681 B1 describes the general use of an $\alpha_{2C}$ antagonist as peripheral vasodilator.

The invention provides compounds of the formula (I)

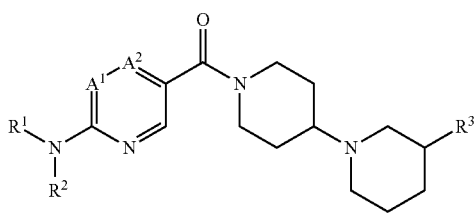

(I)

in which $R^1$ represents $C_2$-$C_6$-alkyl or benzyl,
where alkyl may be substituted by 1 to 2 substituents independently of one another selected from the group consisting of hydroxy, $C_1$-$C_4$-alkoxy, $C_1$-$C_4$-cycloalkyloxy and aminocarbonyloxo,
where benzyl may be substituted by 1 or 2 substituents independently of one another selected from halogen;

and $R^2$ is selected from the group consisting of hydrogen and $C_1$-$C_4$-alkyl;

or $R^1$ and $R^2$ together with the nitrogen atom to which they are attached form a 4- to 7-membered N-heterocycle,
where the N-heterocycle may be substituted by 1 to 3 substituents independently of one another selected from the group consisting of $C_1$-$C_4$-alkyl, $C_1$-$C_4$-alkoxy, $C_1$-$C_4$-alkoxy-$C_1$-$C_4$-alkyl, halogen, oxo, hydroxy, monofluoromethyl, difluoromethyl, trifluoromethyl, hydroxycarbonyl, tert-butoxycarbonyl and aminocarbonyl, or where the N-heterocycle may have two substituents which, together with the carbon atom of the N-heterocycle to which they are jointly attached, form a 4- to 6-membered heterocycle,
where this N-heterocycle for its part may be substituted by 1 to 3 substituents independently of one another selected from the group consisting of oxo, methyl and ethyl;

$R^3$ represents $C_1$-$C_3$-alkyl, $C_1$-$C_3$-alkoxycarbonyl, $C_3$-$C_6$-cycloalkyl, $C_3$-$C_6$-cycloalkyl-$C_1$-$C_3$-alkoxy, $C_3$-$C_6$-cycloalkoxy, trifluoromethoxy-$C_1$-$C_4$-alkoxy, 5- or 6-membered heteroaryl or —OCONR$^4$R$^5$,
where alkyl may be substituted by a substituent selected from the group consisting of $C_1$-$C_4$-alkoxy, $C_3$-$C_6$-cycloalkoxy, trifluoromethoxy and phenoxy,
in which this phenoxy for its part may be substituted by 1 to 3 substituents independently of one another selected from the group consisting of halogen,
and
where heteroaryl may be substituted by 1 to 3 substituents independently of one another selected from the group consisting of $C_1$-$C_4$-alkyl and $C_3$-$C_6$-cycloalkyl,
where this alkyl for its part may be substituted by a substituent selected from the group consisting of $C_1$-$C_3$-alkoxy and $C_3$-$C_6$-cycloalkyl, $R^4$ represents $C_1$-$C_4$-alkyl,
$R^5$ represents hydrogen or $C_1$-$C_4$-alkyl, or $R^4$ and $R^5$ together with the nitrogen atom to which they are attached form a pyrrolidinyl ring,
$A^1$ represents CH and $A^2$ represents N;

or $A^1$ represents N and $A^2$ represents CH;

or $A^1$ and $A^2$ represent CH;

or one of the salts thereof, solvates thereof or solvates of the salts thereof.

Compounds of the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by formula (I) and are mentioned below as embodiments and the salts, solvates and solvates of the salts thereof if the compounds that are encompassed by formula (I) and mentioned below are not already salts, solvates and solvates of the salts.

Preferred salts in the context of the present invention are physiologically acceptable salts of the compounds according to the invention. However, the invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulphonic acids, e.g.

salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

According to one embodiment of the invention, salts of the compounds of the formula (I) are salts of formic acid.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "xHCl", "xCF3COOH", "xNa+" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Depending, inter alia, on the basicity of the compound in question, the term "xacid" represents various ratios of the acid to the compound in question, for example 10:1 to 1:10; 8:1 to 1:8; 7:1 to 1:7; 5:1 to 1:5; 4.5:1 to 1:4.5; 4:1 to 1:4; 3.5:1 to 1:3.5; 3:1 to 1:3; 2.5:1 to 1:2.5; 2:1 to 1:2; 1.5:1 to 1:1.5; and 1:1.

Designated as solvates in the context of the invention are those forms of the compounds according to the invention which form a complex in the solid or liquid state by coordination with solvent molecules. Hydrates are a specific form of the solvates in which the coordination is with water.

The present invention additionally also encompasses prodrugs of the compounds of the invention. The term "prodrugs" encompasses compounds which for their part may be biologically active or inactive but are converted during their residence time in the body into compounds according to the invention (for example by metabolism or hydrolysis).

Depending on their structure, the compounds according to the invention may exist in stereoisomeric forms (enantiomers, diastereomers). The invention therefore encompasses the enantiomers or diastereomers and the respective mixtures thereof. It is possible to isolate the stereoisomerically homogeneous constituents from such mixtures of enantiomers and/or diastereomers in a known manner. Chromatographic methods, in particular HPLC chromatography using a chiral or achiral phase, are preferably used for this purpose.

If the compounds according to the invention can occur in tautomeric forms, the present invention encompasses all the tautomeric forms.

The present invention encompasses all possible stereoisomeric forms of the compounds of the formula (I) and of their starting materials, even if no stereoisomerism is stated.

The present invention also encompasses all suitable isotopic variants of the compounds of the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulphur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound of the invention, especially those in which one or more radioactive isotopes have been incorporated, may be beneficial, for example, for the examination of the mechanism of action or of the active compound distribution in the body; due to comparatively easy preparability and detectability, especially compounds labelled with $^{3}H$ or $^{14}C$ isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds of the invention may therefore in some cases also constitute a preferred embodiment of the present invention. Isotopic variants of the compounds of the invention can be prepared by the processes known to those skilled in the art, for example by the methods described further down and the procedures described in the working examples, by using corresponding isotopic modifications of the respective reagents and/or starting materials.

In the context of the present invention, unless specified otherwise, the substituents are defined as follows:

Alkyl per se and "Alk" and "alkyl" in alkoxy, alkoxyalkyl, alkylamino and alkoxycarbonyl represent a straight-chain or branched alkyl radical having 1 to 6 carbon atoms, preferably 1 to 4 carbon atoms, by way of example and with preference methyl, ethyl, n-propyl, isopropyl, n-butyl, sec-butyl, tert-butyl, n-pentyl, sec-pentyl and n-hexyl.

Alkoxy per se and "alkoxy" in alkoxyalkyl, cycloalkoxy, cycloalkylalkoxy, haloalkoxy represents, by way of example and with preference, methoxy, ethoxy, n-propoxy, isopropoxy, n-butoxy, sec-butoxy and tert-butoxy.

Alkoxyalkyl, by way of example and with preference, represents methoxymethyl, ethoxymethyl, n-propoxymethyl, isopropoxymethyl, n-butoxymethyl, tert-butoxymethyl, methoxyethyl, ethoxyethyl, n-propoxyethyl, isopropoxyethyl, n-butoxyethyl and tert-butoxyethyl.

Alkoxycarbonyl, by way of example and with preference, represents methoxycarbonyl, ethoxycarbonyl, n-propoxycarbonyl, isopropoxycarbonyl, n-butoxycarbonyl and tert-butoxycarbonyl.

Cycloalkyl represents a monocyclic cycloalkyl group having generally 3 to 6, preferably 3 or 6, carbon atoms; cycloalkyl groups which may be mentioned by way of example and with preference are cyclopropyl, cyclobutyl, cyclopentyl and cyclohexyl.

Heteroaryl represents an aromatic monocyclic radical having generally 5 or 6 ring atoms and up to 4 heteroatoms from the group consisting of S, O and N, where a nitrogen atom may also form an N-oxide, by way of example and with preference thienyl, furyl, pyrrolyl, thiazolyl, oxazolyl, isoxazolyl, oxadiazolyl, pyrazolyl, imidazolyl, triazolyl, pyridyl, pyrimidyl, pyridazinyl, pyrazinyl. According to one embodiment, heteroaryl is selected from oxazolyl, isoxazolyl, oxadiazolyl, pyrazolyl, imidazolyl, triazolyl, pyridyl and pyrimidyl.

Halogen represents fluorine, chlorine, bromine and iodine, preferably fluorine and chlorine.

Haloalkyl represents an alkyl radical as defined above which is mono- or polyhalogenated up to the maximum possible number of substituents. In the case of polyhalogenation, the halogen atoms can be identical or different. In the context of the present invention, halogen is fluorine, chlorine, bromine or iodine, preferably fluorine or chlorine.

N-Heterocycle in the definition of the radicals $R^1$ and $R^2$ represents a saturated or partially unsaturated monocyclic radical having 4 to 7 ring atoms having a nitrogen heteroatom and up to 3 further heteroatoms and/or hetero groups from the group consisting of S, O, N, SO and $SO_2$, where a nitrogen atom may also form an N-oxide, by way of example and with preference azetidine, pyrrolidine, piperidine, azepane, piperazine, morpholine, thiomorpholine, 1-oxidothiomorpholine and 1,1-dioxidothiomorpholine, particularly preferably azetidine, pyrrolidine, piperidine, morpholine and 1,1-dioxidothiomorpholine.

Heterocycle in the definition of the radicals $R^1$ and $R^2$, having a joint carbon atom with the N-heterocycle to which it is attached, represents a saturated and partially unsaturated monocyclic radical having 4 to 6 ring atoms and up to 4 heteroatoms and/or hetero groups from the group consisting of S, O, N, SO and $SO_2$, where a nitrogen atom may also form an N-oxide, by way of example and with preference azetidine, oxetane, thietane, pyrrolidine, tetrahydrofuran, piperidine, morpholine, thiomorpholine, piperazine and tetrahydropyran, particularly preferably azetidine and oxetane and even more preferably oxetane.

When radicals in the compounds of the invention are substituted, the radicals may be mono- or polysubstituted, unless specified otherwise. In the context of the present invention, all radicals which occur more than once are defined independently of one another. Substitution by one, two or three identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

Preference is given to compounds of the formula (I) in which
$R^1$ represents $C_2$-$C_6$-alkyl or benzyl,
  where alkyl may be substituted by 1 to 2 substituents independently of one another selected from the group consisting of hydroxy, $C_1$-$C_4$-alkoxy and aminocarbonyloxo, where benzyl may be substituted by 1 or 2 substituents independently of one another selected from fluorine and chlorine;
and
$R^2$ is selected from the group consisting of hydrogen and $C_1$-$C_4$-alkyl;
or
$R^1$ and $R^2$ together with the nitrogen atom to which they are attached form an azetidine, pyrrolidine, piperidine, azepane, piperazine, morpholine, thiomorpholine, 1-oxidothiomorpholine or 1,1-dioxidothiomorpholine,
  where azetidine, pyrrolidine, piperidine, azepane, piperazine, morpholine, thiomorpholine, 1-oxidothiomorpholine and 1,1-dioxidothiomorpholine may be substituted by 1 to 3 substituents independently of one another selected from the group consisting of $C_1$-$C_2$-alkyl, $C_1$-$C_2$-alkoxy, $C_1$-$C_2$-alkoxy-$C_1$-$C_2$-alkyl and halogen,
or
  where azetidine, pyrrolidine, piperidine, azepane, piperazine, morpholine, thiomorpholine, 1-oxidothiomorpholine and 1,1-dioxidothiomorpholine may have two substituents which together with the carbon atom of the azetidine, pyrrolidine, piperidine, azepane, piperazine, morpholine, thiomorpholine, 1-oxidothiomorpholine or 1,1-dioxidothiomorpholine to which they are jointly attached form an azetidine or oxetane,
    where this azetidine or oxetane for its part may be substituted by 1 to 2 substituents independently of one another selected from the group consisting of 3-methyl and 3-ethyl,
$R^3$ is selected from the group consisting of $C_1$-$C_4$-alkyl and $C_3$-$C_6$-cycloalkyl-$C_1$-$C_4$-alkoxy;
$A^1$ represents CH and $A^2$ represents N;
or
$A^1$ represents N and $A^2$ represents CH;
or
$A^1$ and $A^2$ represent CH;
or one of the salts thereof, solvates thereof or solvates of the salts thereof.

Preference is also given to compounds of the formula (I) in which
$R^1$ represents $C_2$-$C_4$-alkyl or benzyl,
  where alkyl may be substituted by 1 to 2 substituents independently of one another selected from the group consisting of hydroxy, $C_1$-$C_2$-alkoxy and aminocarbonyloxo,
  where benzyl may be substituted by 1 or 2 fluorine substituents,
and
$R^2$ represents hydrogen or $C_1$-$C_2$-alkyl;
or
$R^1$ and $R^2$ together with the nitrogen atom to which they are attached form an azetidine, pyrrolidine, piperidine, morpholine or 1,1-dioxidothiomorpholine,
  where azetidine, pyrrolidine, piperidine, morpholine or 1,1-dioxidothiomorpholine may be substituted by 1 to 2 substituents selected independently from the group consisting of methyl, methoxy, methoxymethyl and fluorine,
or
  where azetidine, pyrrolidine, piperidine, morpholine and 1,1-dioxidothiomorpholine may have two substituents which together with the carbon atom of the azetidine, pyrrolidine, piperidine, morpholine or 1,1-dioxidothiomorpholine to which they are jointly attached form an azetidine or oxetane, where this azetidine or oxetane for its part may be substituted by 1 to 2 substituents independently of one another selected from the group consisting of 3-methyl and 3-ethyl, R³ is selected from the group consisting of methyl and cyclopropylmethoxy;

A¹ represents CH and A² represents N;

or

A¹ represents N and A² represents CH;

or

A¹ and A² represent CH;

or one of the salts thereof, solvates thereof or solvates of the salts thereof.

Preference is also given to compounds of the formula (I) in which

R¹ is selected from the group consisting of methoxyethyl, hydroxy-sec-butyl, sec-butyl carbamate, methoxy-sec-butyl and benzyl, where benzyl may be substituted by 1 to 2 fluorine substituents;

and

R² represents hydrogen or methyl;

or

R¹ and R² together with the nitrogen atom to which they are attached form an azetidine, pyrrolidine, piperidine, morpholine or 1,1-dioxidothiomorpholine, where azetidine, pyrrolidine, piperidine, morpholine or 1,1-dioxidothiomorpholine may be substituted by 1 to 2 substituents selected independently from the group consisting of methyl, methoxy, methoxymethyl and fluorine, or where azetidine may have two substituents which together with the carbon atom of the azetidine to which they are jointly attached form an oxetane, R³ is selected from the group consisting of methyl and cyclopropylmethoxy;

A¹ represents CH;

and

A² represents N;

or

A¹ represents N;

and

A² represents CH;

or

A¹ and A² represent CH;

or one of the salts thereof, solvates thereof or solvates of the salts thereof.

Preference is also given to compounds of the formula (I) in which

R¹ represents benzyl, where benzyl is substituted by 2 fluorine substituents;

and

R² represents methyl;

R³ represents methyl;

A¹ and A² represent CH;

or one of the salts thereof, solvates thereof or solvates of the salts thereof.

Preference is also given to compounds of the formula (I) in which R¹ represents sec-butyl which may be substituted by a substituent selected from the group consisting of hydroxy, methoxy and carbamate.

Preference is also given to compounds of the formula (I) in which R¹ represents methoxyethyl.

Preference is also given to compounds of the formula (I) in which R¹ represents benzyl which may be substituted by 1-2 fluorine substituents.

Preference is also given to compounds of the formula (I) in which R² represents hydrogen.

Preference is also given to compounds of the formula (I) in which R² represents methyl.

Preference is also given to compounds of the formula (I) in which R¹ and R² together with the nitrogen atom to which they are attached form a 2-methoxymethylpyrrolidine, 3-methoxypyrrolidine, 4,4-difluoropiperidine, 3-methylpiperidine, morpholine, 1,1-dioxidothiomorpholine or 2-oxa-6-azaspiro[3.3]hept-6-yl.

Preference is also given to compounds of the formula (I) in which R³ represents methyl.

Preference is also given to compounds of the formula (I) in which R³ represents cyclopropylmethoxy.

Preference is also given to compounds of the formula (I) in which A¹ represents CH and A² represents N.

Preference is also given to compounds of the formula (I) in which A¹ represents N and A² represents CH.

Preference is also given to compounds of the formula (I) in which A¹ and A² represent CH.

Irrespective of the particular combinations of the radicals specified, the individual radical definitions specified in the particular combinations or preferred combinations of radicals are also replaced as desired by radical definitions of other combinations.

Very particular preference is given to combinations of two or more of the abovementioned preferred ranges.

Irrespective of the particular combinations of the radicals specified, the individual radical definitions specified in the particular combinations or preferred combinations of radicals are also replaced as desired by radical definitions of other combinations.

Very particular preference is given to combinations of two or more of the abovementioned preferred ranges.

The invention further provides a process for preparing the compounds of the formula (I) and their starting materials and intermediates, or the salts thereof, the solvates thereof or the solvates of the salts thereof, where

[A] compounds of the formula (II)

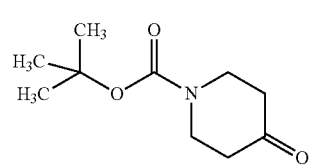

(II)

are reacted with compounds of the formula (III)

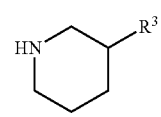

(III)

in which R³ has the meanings given above, in the presence of a reducing agent to give compounds of the formula (IV)

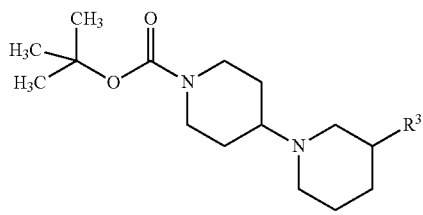

in which R³ has the meanings given above,
or
[B] compounds of the formula (IV)

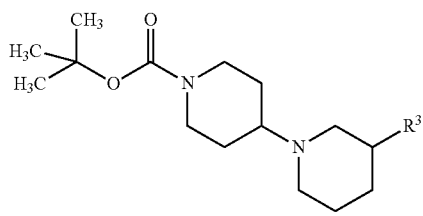

in which R³ has the meanings given above,
are reacted in the presence of an acid to give compounds of the formula (V)

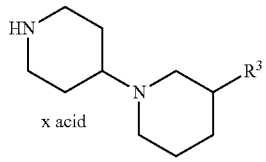

in which R³ has the meanings given above,
or
[C] compounds of the formula (VI)

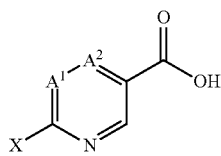

in which X represents halogen, preferably fluorine, chlorine or bromine, or sulphonylmethane,
in which A¹ represents CH and A² represents CH or N,
are reacted with compounds of the formula (VII)

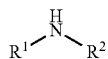

in which R¹ and R² have the meanings given above, to give compounds of the formula (VIII)

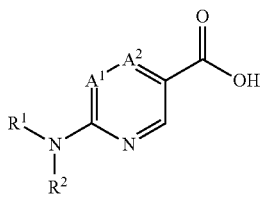

in which A¹ represents CH, A² represents CH or N and R¹ and R² have the meanings given above,
or
[D] compounds of the formula (VIII)

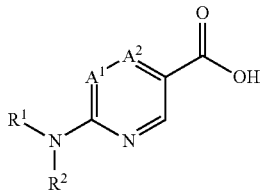

in which R¹, R², A¹ and A² have the meanings given above, are reacted with compounds of the formula (V)

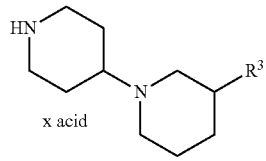

in which R³ has the meanings given above,
in the presence of a dehydrating agent to give compounds of the formula (I) or
[E] compounds of the formula (VI)

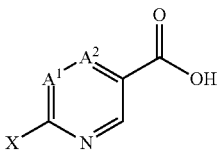

in which X represents halogen, preferably fluorine, chlorine or bromine, or sulphonylmethane,
A¹ and A² have the meanings given above, with the proviso that, if X represents halogen, A¹ represents CH and A² represents CH or N,
are reacted with compounds of the formula (V)

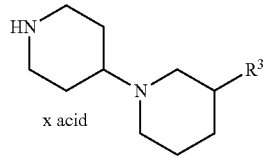

in which R³ has the meanings given above, in the presence of a dehydrating agent to give compounds of the formula (IX)

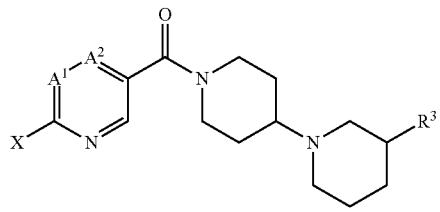

(IX)

in which R³, A¹ and A² have the meanings given above and in which X represents halogen, preferably fluorine, chlorine or bromine, or sulphonylmethane,
with the proviso that, if X represents halogen, A¹ represents CH and A² represents CH or N,
or
[F] compounds of the formula (IX)

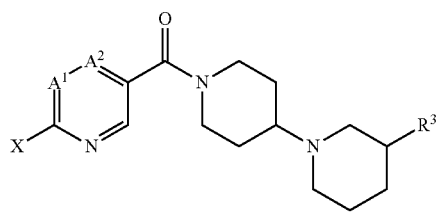

(IX)

in which R³, A¹ and A² have the meanings given above and in which X represents halogen, preferably fluorine, chlorine or bromine, or sulphonylmethane,
with the proviso that, if X represents halogen, A¹ represents CH and A² represents CH or N,
are reacted with compounds of the formula (VII)

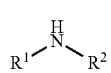

(VII)

in which R¹ and R² have the meanings given above,
to give compounds of the formula (I) in which R¹, R², R³, A¹ and A² have the meanings given above,
with the proviso that, if X in formula (IX) represents halogen, A¹ represents CH and A² represents CH or N, or
[G] compounds of the formula (X)

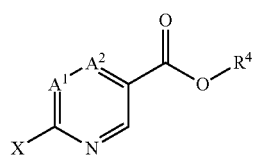

(X)

in which
X represents halogen, preferably chlorine, fluorine or bromine, or sulphonylmethane,
R⁴ represents $C_1$-$C_4$-alkyl, preferably methyl or ethyl, and
A¹ and A² have the meanings given above, are reacted in the presence of a base with compounds of the formula (VII)

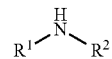

(VII)

in which R¹ and R² have the meanings given above,
to give compounds of the formula (XI)

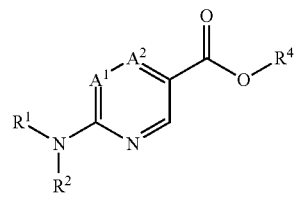

(XI)

in which
R⁴ represents $C_1$-$C_4$-alkyl, preferably methyl or ethyl, and
in which R¹, R², A¹ and A² have the meanings given above,
or
[H] compounds of the formula (VIII)

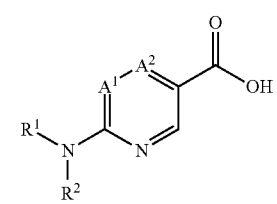

(VIII)

in which R¹, R², A¹ and A² have the meanings given above,
are reacted with compounds of the formula (V)

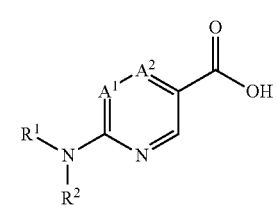

(V)

in which R³ has the meanings given above,
in the presence of a dehydrating agent to give compounds of the formula (I) or
[I] compounds of the formula (VIII)

(VIII)

in which R¹, R², A¹ and A² have the meanings given above, are reacted with piperidin-4-one to give compounds of the formula (XII)

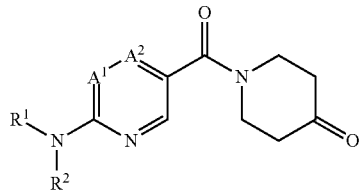
(XII)

in which $R^1$, $R^2$, $A^1$ and $A^2$ have the meanings given above,
or
[J] compounds of the formula (XII)

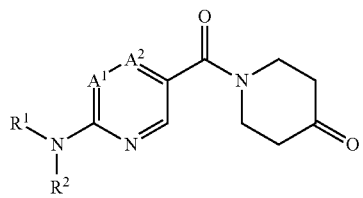
(XII)

in which $R^1$, $R^2$, $A^1$ and $A^2$ have the meanings given above, are reacted with compounds of the formula (III)

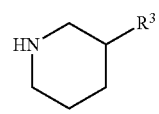
(III)

in which $R^3$ has the meanings given above,
in the presence of a reducing agent to give compounds of the formula (I).

The reaction according to process [A] is generally carried out in inert solvents, preferably in a temperature range of from −20° C. to 60° C. at atmospheric pressure and optionally in the presence of a base.

Inert solvents are, for example, alcohols such as methanol, ethanol, n-propanol or isopropanol, or ethers such as diethyl ether, dioxane or tetrahydrofuran, or dimethylformamide, or acetic acid or glacial acetic acid, or dichloromethane, trichloromethane or 1,2-dichloroethane. It is also possible to use mixtures of the solvents mentioned. Preference is given to dichloromethane or tetrahydrofuran.

Bases are, for example, organic bases such as trialkylamines, for example triethylamine, N-methylmorpholine, N-methylpiperidine, 4-dimethylaminopyridine or diisopropylethylamine; preference is given to diisopropylethylamine.

Reducing agents are, for example, sodium borohydride, lithium borohydride, sodium cyanoborohydride, lithium aluminium hydride, sodium bis(2-methoxyethoxy)aluminium hydride, sodium triacetoxyborohydride or borane/tetrahydrofuran; preference is given to sodium triacetoxyborohydride.

The compounds of the formulae (II) and (III) are known or can be synthesized by known processes from the appropriate starting materials.

Alternatively to process [A] described above, the preparation of the compounds of the formula (IV) may also comprise a process where
[K] compounds of the formula (II)

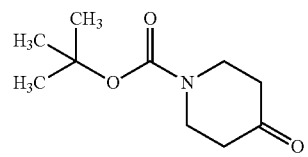
(II)

are reacted with compounds of the formula (III)

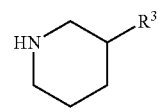
(III)

in which $R^3$ has the meanings given above,
to give compounds of the formula (IVa)

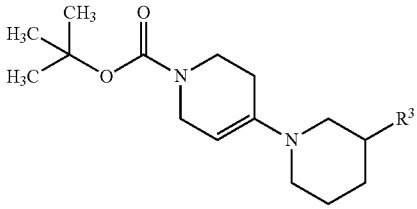
(IVa)

in which $R^3$ has the meanings given above,
or
[L] compounds of the formula (IVa)

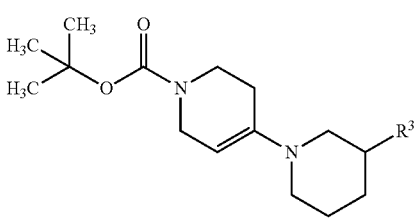
(IVa)

in which $R^3$ has the meanings given above,
are reacted in the presence of a reducing agent to give compounds of the formula (IV).

Reducing agents in a reaction according to process [L] can be, for example, sodium borohydride, lithium borohydride, sodium cyanoborohydride, lithium aluminium hydride, sodium bis(2-methoxyethoxy)aluminium hydride, sodium triacetoxyborohydride, borane/tetrahydrofuran, or hydrogen in the presence of palladium catalysts.

The reaction according to process [B] is generally carried out in inert solvents, preferably in a temperature range from −20° C. to 60° C. at atmospheric pressure.

Inert solvents are, for example, alcohols such as methanol, ethanol, n-propanol or isopropanol, or ethers such as diethyl ether, dioxane or tetrahydrofuran, or dimethylformamide, or dichloromethane, trichloromethane or 1,2-dichloroethane. It is also possible to use mixtures of the solvents mentioned. Preference is given to dichloromethane.

Acids are, for example, hydrogen chloride and trifluoroacetic acid; preference is given to hydrogen chloride. These acids are preferably added dissolved in an inert solvent. A solvent which is preferred for this purpose is dioxane.

The reaction according to process [C] is generally carried out in inert solvents, if appropriate in a microwave apparatus, preferably in a temperature range of from 100° C. to 220° C. at from atmospheric pressure to 5 bar.

Inert solvents are, for example, alcohols such as methanol, ethanol, n-propanol or isopropanol, or ethers such as diethyl ether, dioxane, tetrahydrofuran or N-methylmorpholinone, or dimethylformamide, or dichloromethane, trichloromethane, 1,2-dichloroethane or acetonitrile. It is also possible to use mixtures of the solvents mentioned. It is likewise possible to use at least one of the reactants, for example morpholines, as solvent. Preference is given to n-propanol or morpholine.

The reaction according to process [D] is generally carried out in inert solvents, if appropriate in the presence of a base, preferably in a temperature range of from −30° C. to 50° C. at atmospheric pressure.

Inert solvents are, for example, halogenated hydrocarbons, such as dichloromethane or trichloromethane, hydrocarbon such as benzene, nitromethane, dioxane, dimethylformamide or acetonitrile. It is also possible to use mixtures of the solvents mentioned. Particular preference is given to acetonitrile.

Suitable dehydrating agents are, for example, carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride (T3P), or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures of these, with bases.

Bases are, for example, alkali metal carbonates such as sodium carbonate or potassium carbonate, or sodium bicarbonate or potassium bicarbonate, or organic bases such as trialkylamines, for example triethylamine, N-methylmorpholine, N-methylpiperidine, 4-dimethylaminopyridine or diisopropylethylamine; preference is given to diisopropylethylamine.

The condensation is preferably carried out using propanephosphonic anhydride.

The dehydrating agents mentioned in the reaction according to process [E] may, for example, be those described in connection with the reactions according to process [D].

The reducing agents mentioned in the reaction according to process [F] may, for example, be those described in connection with the reactions according to process [C] or [G].

The reaction according to process [G] is generally carried out in inert solvents, preferably in a temperature range from 0° C. to 80° C. at atmospheric pressure.

Inert solvents are, for example, alcohols such as isopropanol or ethers such as diethyl ether, dioxane, tetrahydrofuran or N-methylmorpholinone, or dimethylformamide, or dichloromethane, trichloromethane, 1,2-dichloroethane, or acetonitrile. Preference is given to acetonitrile and N-methylmorpholine. It is also possible to use mixtures of the solvents mentioned.

Bases are, for example, alkali metal carbonates, for example sodium carbonate, potassium carbonate or caesium carbonate, or sodium bicarbonate, potassium bicarbonate or caesium bicarbonate, or organic bases such as trialkylamines, for example triethylamine, N-methylmorpholine, N-methylpiperidine, 4-dimethylaminopyridine or diisopropylethylamine, with potassium carbonate and sodium carbonate being preferred.

The compounds of the formulae (X) and (VII) are known or can be synthesized by known processes from the appropriate starting compounds.

The reaction according to process [H] is generally carried out in inert solvents, if appropriate in the presence of a base, preferably in a temperature range of from −30° C. to 50° C. at atmospheric pressure.

Inert solvents are, for example, halogenated hydrocarbons, such as dichloromethane or trichloromethane, hydrocarbon such as benzene, nitromethane, dioxane, dimethylformamide or acetonitrile. It is also possible to use mixtures of the solvents mentioned. Particular preference is given to acetonitrile.

Suitable dehydrating agents are, for example, carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride (T3P), or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures of these, with bases.

Bases are, for example, alkali metal carbonates such as sodium carbonate or potassium carbonate, or sodium bicarbonate or potassium bicarbonate, or organic bases such as trialkylamines, for example triethylamine, N-methylmorpholine, N-methylpiperidine, 4-dimethylaminopyridine or diisopropylethylamine; preference is given to diisopropylethylamine.

The condensation is preferably carried out using propanephosphonic anhydride.

The compounds of the formula (VIII) can be prepared by hydrolyzing the carboxylic ester in compounds of the formula (XI).

The hydrolysis is generally carried out in inert solvents, in the presence of at least one base, preferably in a temperature range from 0° C. to 90° C. at atmospheric pressure.

Bases are, for example, alkali metal hydroxides such as lithium hydroxide or sodium hydroxide, which can each be employed in the form of an aqueous solution. Preference is given to aqueous solutions of lithium hydroxide and sodium hydroxide.

Inert solvents are, for example, polar solvents such as alcohols, for example methanol, ethanol, n-propanol or isopropanol, or ethers such as diethyl ether, dioxane, tetrahydrofuran or N-methylmorpholine. It is also possible to use mixtures of the solvents mentioned. Preference is given to dioxane, ethanol and mixtures of tetrahydrofuran and methanol.

Reducing agents in a reaction according to process [H] can be, for example, sodium borohydride, lithium borohydride, sodium cyanoborohydride, lithium aluminium hydride, sodium bis(2-methoxyethoxy)aluminium hydride, sodium triacetoxyborohydride or borane/tetrahydrofuran.

The reaction according to process [I] is generally carried out in inert solvents, if appropriate in the presence of a base, preferably in a temperature range of from −30° C. to 50° C. at atmospheric pressure.

Inert solvents are, for example, halogenated hydrocarbons, such as dichloromethane or trichloromethane, hydrocarbon such as benzene, nitromethane, dioxane, dimethylformamide or acetonitrile. It is also possible to use mixtures of the solvents mentioned. Particular preference is given to acetonitrile.

Suitable dehydrating agents are, for example, carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride (T3P), or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures of these, with bases.

Bases are, for example, alkali metal carbonates such as sodium carbonate, potassium carbonate or caesium carbonate, or sodium bicarbonate, potassium bicarbonate or caesium bicarbonate, or organic bases such as trialkylamines, for example triethylamine, N-methylmorpholine, N-methylpiperidine, 4-dimethylaminopyridine or diisopropylethylamine, with diisopropylethylamine being preferred.

The condensation is preferably carried out using propanephosphonic anhydride.

Reducing agents in a reaction according to process [J] can be, for example, sodium borohydride, lithium borohydride, sodium cyanoborohydride, lithium aluminium hydride, sodium bis(2-methoxyethoxy)aluminium hydride, sodium triacetoxyborohydride or borane/tetrahydrofuran.

The invention furthermore provides a process for preparing the compounds of the formula (I) or the salts thereof, the solvates thereof or the solvates of the salts thereof, where this process comprises reactions according to the processes described above, selected from a group comprising the combinations

[A] and [B],

[C] and [D],

[E] and [F],

[G] and [H],

[I] and [J],

[A], [B] and [D],

[A], [B] and [E],

[A], [B] and [H],

[A], [B], [E] and [F].

The preparation of the compounds of the formula (I) can be illustrated by the synthesis schemes below.

Synthesis Scheme 1:

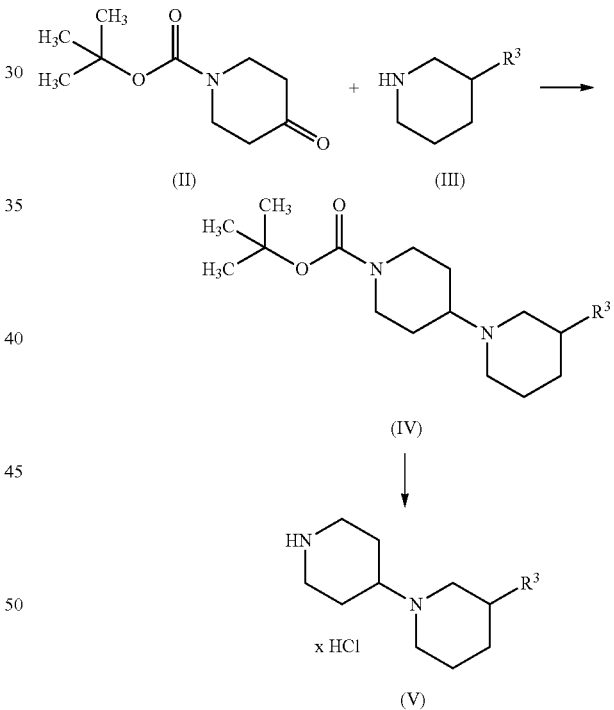

Synthesis Scheme 2:

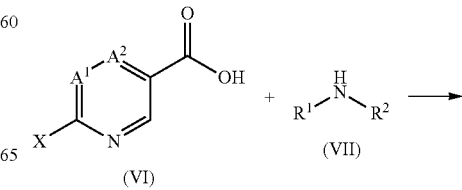

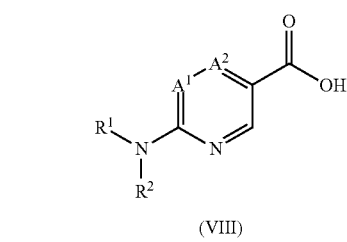
(VIII)
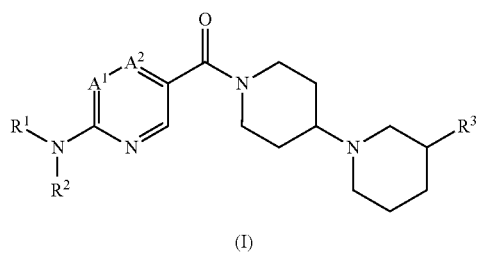
(I)
Synthesis Scheme 4:
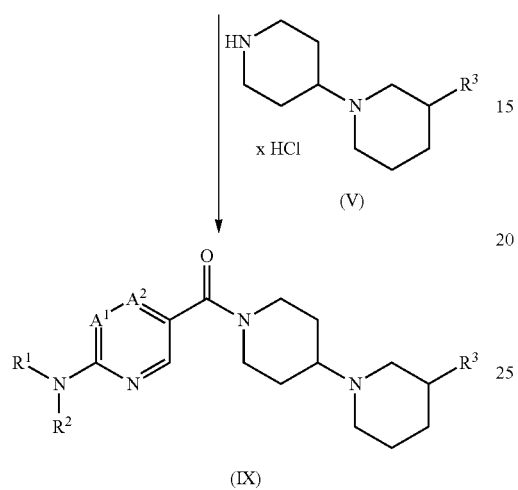
Synthesis Scheme 3:
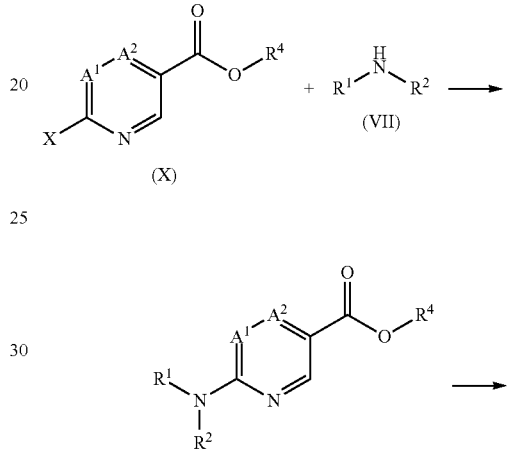
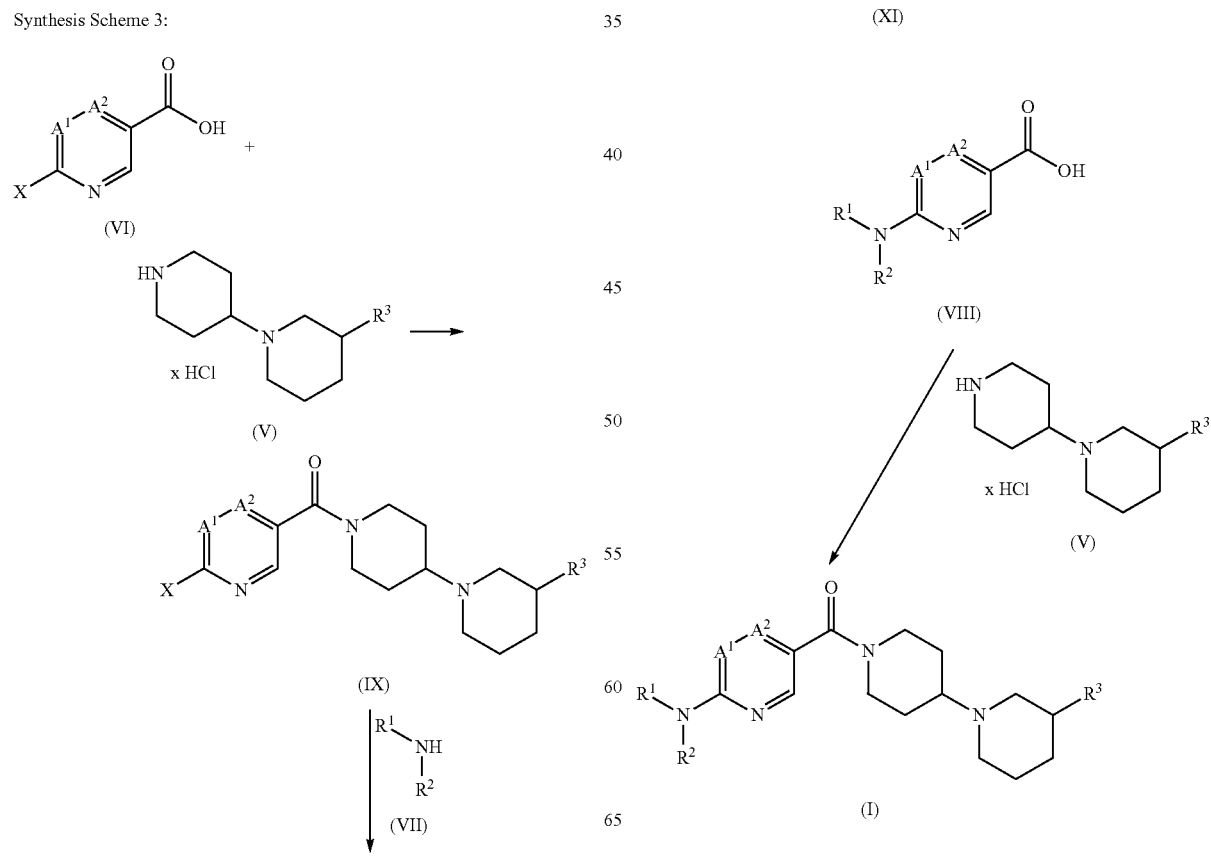

Synthesis Scheme 5 (alternative route):

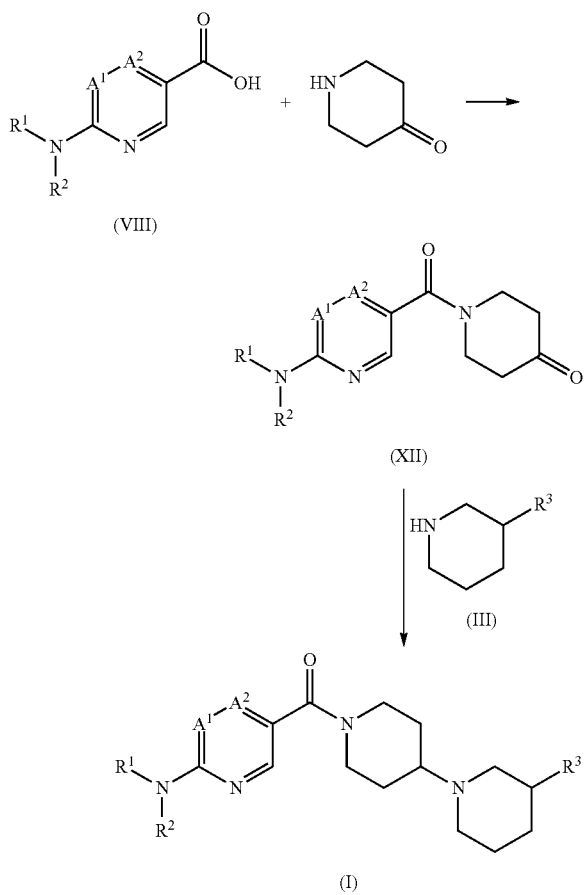

The invention also provides compounds of the formula

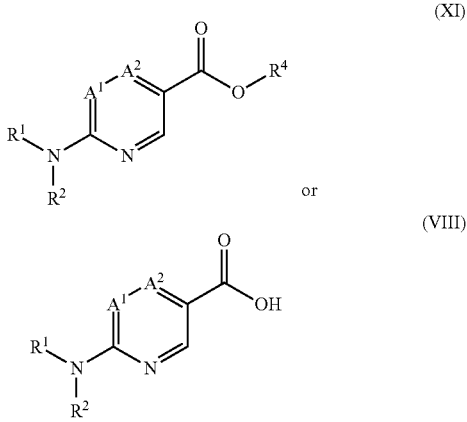

in which
R¹ represents benzyl, where benzyl is substituted by 2 fluorine substituents;
and
R² represents methyl;
R⁴ represents $C_1$-$C_4$-alkyl, preferably methyl or ethyl;
A¹ and A² represent CH;
and the salts thereof, the solvates thereof and the solvates of the salts thereof.

The compounds according to the invention have an unforeseeable useful spectrum of pharmacological activity, including useful pharmacokinetic properties. They are selective adrenoreceptor $α_{2C}$ receptor antagonists which lead to vasorelaxation and/or inhibit platelet aggregation and/or lower blood pressure and/or increase coronary or peripheral blood flow. Accordingly, they are suitable for the treatment and/or prophylaxis of diseases, preferably cardiovascular disorders, diabetic microangiopathies, diabetic ulcers on the extremities, in particular for promoting wound healing of diabetic foot ulcers, diabetic heart failure, diabetic coronary microvascular heart disorders, peripheral and cardiac vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies in humans and animals.

In particular, the compounds according to the invention show a disease-selective improvement of peripheral blood flow (micro- and macrocirculation) under pathophysiologically changed conditions, for example as a consequence of diabetes mellitus or atherosclerosis.

The compounds according to the invention are therefore suitable for use as medicaments for the treatment and/or prophylaxis of diseases in humans and animals.

Accordingly, the compounds according to the invention are suitable for the treatment of cardiovascular disorders such as, for example, for the treatment of high blood pressure, for primary and/or secondary prevention, and also for the treatment of heart failure, for the treatment of stable and unstable angina pectoris, pulmonary hypertension, peripheral and cardiac vascular disorders (e.g. peripheral occlusive disease), arrhythmias, for the treatment of thromboembolic disorders and ischaemias such as myocardial infarction, stroke, transitory and ischaemic attacks, peripheral circulatory disturbances, for the prevention of restenoses such as after thrombolysis therapies, percutaneous transluminal angioplasties (PTAs), percutaneous transluminal coronary angioplasties (PTCAs) and bypass, and also for the treatment of ischaemia syndrome, atherosclerosis, asthmatic disorders, diseases of the urogenital system such as, for example, prostate hypertrophy, erectile dysfunction, female sexual dysfunction and incontinence.

Moreover, the compounds according to the invention can be used for the treatment of primary and secondary Raynaud's phenomenon, of microcirculatory disturbances, intermittent claudication, peripheral and autonomous neuropathies, diabetic microangiopathies, diabetic nephropathy, diabetic retinopathy, diabetic ulcers on the extremities, diabetic erectile dysfunction, CREST syndrome, erythematosis, onychomycosis, tinnitus, dizzy spells, sudden deafness, Meniere's disease and of rheumatic disorders.

The compounds according to the invention are furthermore suitable for the treatment of respiratory distress syndromes and chronic-obstructive pulmonary disease (COPD), of acute and chronic kidney failure and for promoting wound healing and here in particular diabetic wound healing.

Moreover, the compounds of the formula (I) according to the invention are suitable for the treatment and/or prophylaxis of comorbidities and/or sequelae of diabetes mellitus. Examples of comorbidities and/or sequelae of diabetes mellitus are diabetic heart disorders such as, for example, diabetic coronary heart disorders, diabetic coronary microvascular heart disorders (coronary microvascular disease, MVD), diabetic heart failure, diabetic cardiomyopathy and myocardial infarction, hypertension, diabetic microangiopathies, diabetic retinopathy, diabetic neuropathy, stroke, diabetic nephropathy, diabetic erectile dysfunction, diabetic ulcers on the extremities and diabetic foot syndrome. Moreover, the compounds of the formula (I) according to the invention are suitable for promoting diabetic wound healing, in particular for promoting wound healing of diabetic foot ulcers. Promotion of wound healing of diabetic foot ulcers is defined, for example, as improved wound closure.

In addition, the compounds according to the invention are also suitable for controlling cerebral blood flow and are effective agents for controlling migraines. They are also suitable for the prophylaxis and control of sequelae of cerebral infarction (cerebral apoplexy) such as stroke, cerebral ischaemias and craniocerebral trauma. The compounds according to the invention can likewise be employed for controlling states of pain.

In addition, the compounds according to the invention can also be employed for the treatment and/or prevention of micro- and macrovascular damage (vasculitis), reperfusion damage, arterial and venous thromboses, oedemas, neoplastic disorders (skin cancer, liposarcomas, carcinomas of the gastrointestinal tract, of the liver, of the pancreas, of the lung, of the kidney, of the ureter, of the prostate and of the genital tract), of disorders of the central nervous system and neurodegenerative disorders (stroke, Alzheimer's disease, Parkinson's disease, dementia, epilepsy, depressions, multiple sclerosis, schizophrenia), of inflammatory disorders, autoimmune disorders (Crohn's disease, ulcerative colitis, lupus erythematosus, rheumatoid arthritis, asthma), kidney disorders (glomerulonephritis), thyroid disorders (hyperthyreosis), hyperhydrosis, disorders of the pancreas (pancreatitis), liver fibrosis, skin disorders (psoriasis, acne, eczema, neurodermitis, dermatitis, keratitis, formation of scars, formation of warts, chilblains), skin grafts, viral disorders (HPV, HCMV, HIV), cachexia, osteoporosis, avascular bone necrosis, gout, incontinence, for wound healing, for wound healing in patients having sickle cell anaemia, and for angiogenesis.

The present invention furthermore provides the use of the compounds according to the invention for the treatment and/or prophylaxis of disorders, preferably of thromboembolic disorders and/or thromboembolic complications.

"Thromboembolic disorders" in the sense of the present invention include in particular disorders such as ST-segment elevation myocardial infarction (STEMI) and non-ST-segment elevation myocardial infarction (non-STEMI), stable angina pectoris, unstable angina pectoris, reocclusions and restenoses after coronary interventions such as angioplasty, stent implantation or aortocoronary bypass, peripheral arterial occlusion diseases, pulmonary embolisms, deep venous thromboses and renal vein thromboses, transitory ischaemic attacks and also thrombotic and thromboembolic stroke and pulmonary hypertension.

Accordingly, the substances are also suitable for the prevention and treatment of cardiogenic thromboembolisms, such as, for example, brain ischaemias, stroke and systemic thromboembolisms and ischaemias, in patients with acute, intermittent or persistent cardiac arrhythmias, such as, for example, atrial fibrillation, and those undergoing cardioversion, furthermore in patients with heart valve disorders or with intravasal objects, such as, for example, artificial heart valves, catheters, intraaortic balloon counterpulsation and pacemaker probes. In addition, the compounds according to the invention are suitable for the treatment of disseminated intravasal coagulation (DIC).

Thromboembolic complications are furthermore encountered in connection with microangiopathic haemolytic anaemias, extracorporeal circulation, such as, for example, haemodialysis, haemofiltration, ventricular assist device and artificial hearts, and also heart valve prostheses.

The compounds according to the invention are particularly suitable for the primary and/or secondary prevention and treatment of heart failure.

In the context of the present invention, the term heart failure also includes more specific or related types of disease, such as right heart failure, left heart failure, global failure, ischaemic cardiomyopathy, dilated cardiomyopathy, congenital heart defects, heart valve defects, heart failure associated with heart valve defects, mitral stenosis, mitral insufficiency, aortic stenosis, aortic insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

The compounds according to the invention are particularly suitable for the treatment and/or prophylaxis of cardiovascular disorders, in particular heart failure, and/or circulatory disturbances and microangiopathies associated with diabetes mellitus.

The compounds according to the invention are also suitable for the primary and/or secondary prevention and treatment of the abovementioned disorders in children.

The present invention further provides the compounds according to the invention for use in a method for the treatment and/or prophylaxis of disorders, especially the disorders mentioned above.

The present invention further provides for the use of the compounds according to the invention for the treatment and/or prophylaxis of disorders, especially the disorders mentioned above.

The present invention further provides for the use of the compounds according to the invention for production of a medicament for the treatment and/or prophylaxis of disorders, especially the disorders mentioned above.

The present invention further provides a method for the treatment and/or prophylaxis of disorders, especially the disorders mentioned above, using a therapeutically effective amount of a compound according to the invention.

The present invention further provides adrenoreceptor α2C receptor antagonists for use in a method for the treatment and/or prophylaxis of comorbidities and/or sequelae of diabetes mellitus, diabetic heart disorders, diabetic coronary heart disorders, diabetic coronary microvascular heart disorders, diabetic heart failure, diabetic cardiomyopathy and myocardial infarction, diabetic microangiopathy, diabetic retinopathy, diabetic neuropathy, diabetic nephropathy, diabetic erectile dysfunction, diabetic ulcers on the extremities, diabetic foot ulcers, for promoting diabetic wound healing, and for promoting wound healing of diabetic foot ulcers.

The present invention further provides adrenoreceptor α2C receptor antagonists for use in a method for the treatment and/or prophylaxis of diabetic microangiopathies, diabetic retinopathy, diabetic neuropathy, diabetic nephropathy, diabetic erectile dysfunction, diabetic heart failure, diabetic coronary microvascular heart diseases, diabetic ulcers on the extremities, diabetic foot ulcers, for promoting diabetic wound healing and for promoting wound healing of diabetic foot ulcers.

The present invention further provides competitive adrenoreceptor α2C receptor antagonists for use in a method for the treatment and/or prophylaxis of comorbidities and/or sequelae of diabetes mellitus, diabetic heart disorders, diabetic coronary heart disorders, diabetic coronary microvascular heart disorders, diabetic heart failure, diabetic cardiomyopathy and myocardial infarction, diabetic microangiopathy, diabetic retinopathy, diabetic neuropathy, diabetic nephropathy, diabetic erectile dysfunction, diabetic ulcers on the extremities, diabetic foot ulcers, for promoting diabetic wound healing, and for promoting wound healing of diabetic foot ulcers.

The present invention further provides medicaments comprising at least one adrenoreceptor α2C receptor antagonist in combination with one or more inert non-toxic pharmaceutically suitable auxiliaries for the treatment and/or prophylaxis of comorbidities and/or sequelae of diabetes mellitus, diabetic heart disorders, diabetic coronary heart disorders, diabetic coronary microvascular heart disorders, diabetic heart failure, diabetic cardiomyopathy and myocardial infarction, diabetic microangiopathy, diabetic retinopathy, diabetic neuropathy, diabetic nephropathy, diabetic erectile dysfunction, diabetic ulcers on the extremities, diabetic foot ulcers, for promoting diabetic wound healing, and for promoting wound healing of diabetic foot ulcers.

The present invention further provides medicaments comprising at least one adrenoreceptor α2C receptor antagonist in combination with one or more inert non-toxic pharmaceutically suitable auxiliaries for the treatment and/or prophylaxis of diabetic microangiopathies, diabetic retinopathy, diabetic neuropathy, diabetic nephropathy, diabetic erectile dysfunction, diabetic heart failure, diabetic coronary microvascular heart diseases, diabetic ulcers on the extremities, diabetic foot ulcers, for promoting diabetic wound healing and for promoting wound healing, of diabetic foot ulcers.

The present invention further provides medicaments comprising at least one competitive adrenoreceptor α2C receptor antagonist in combination with one or more inert non-toxic pharmaceutically suitable auxiliaries for the treatment and/or prophylaxis of comorbidities and/or sequelae of diabetes mellitus, diabetic heart disorders, diabetic coronary heart disorders, diabetic coronary microvascular heart disorders, diabetic heart failure, diabetic cardiomyopathy and myocardial infarction, diabetic microangiopathy, diabetic retinopathy, diabetic neuropathy, diabetic nephropathy, diabetic erectile dysfunction, diabetic ulcers on the extremities, diabetic foot ulcers, for promoting diabetic wound healing, and for promoting wound healing of diabetic foot ulcers.

The present invention further provides medicaments comprising at least one adrenoreceptor α2C receptor antagonist in combination with one or more further active compounds selected from the group consisting of lipid metabolism-modulating active compounds, antidiabetics, hypotensive agents, agents which lower the sympathetic tone, perfusion-enhancing and/or antithrombotic agents and also antioxidants, aldosterone and mineralocorticoid receptor antagonists, vasopressin receptor antagonists, organic nitrates and NO donors, IP receptor agonists, positive inotropic compounds, calcium sensitizers, ACE inhibitors, cGMP- and cAMP-modulating compounds, natriuretic peptides, NO-independent stimulators of guanylate cyclase, NO-independent activators of guanylate cyclase, inhibitors of human neutrophil elastase, compounds which inhibit the signal transduction cascade, compounds which modulate the energy metabolism of the heart, chemokine receptor antagonists, p38 kinase inhibitors, NPY agonists, orexin agonists, anorectics, PAF-AH inhibitors, antiphlogistics, analgesics, antidepressants and other psychopharmaceuticals.

The present invention further provides medicaments comprising at least one competitive adrenoreceptor α2C receptor antagonist in combination with one or more further active compounds selected from the group consisting of lipid metabolism-modulating active compounds, antidiabetics, hypotensive agents, agents which lower the sympathetic tone, perfusion-enhancing and/or antithrombotic agents and also antioxidants, aldosterone and mineralocorticoid receptor antagonists, vasopressin receptor antagonists, organic nitrates and NO donors, IP receptor agonists, positive inotropic compounds, calcium sensitizers, ACE inhibitors, cGMP- and cAMP-modulating compounds, natriuretic peptides, NO-independent stimulators of guanylate cyclase, NO-independent activators of guanylate cyclase, inhibitors of human neutrophil elastase, compounds which inhibit the signal transduction cascade, compounds which modulate the energy metabolism of the heart, chemokine receptor antagonists, p38 kinase inhibitors, NPY agonists, orexin agonists, anorectics, PAF-AH inhibitors, antiphlogistics, analgesics, antidepressants and other psychopharmaceuticals.

The present invention further provides a method for the treatment and/or prophylaxis of comorbidities and/or sequelae of diabetes mellitus, diabetic heart disorders, diabetic coronary heart disorders, diabetic coronary microvascular heart disorders, diabetic heart failure, diabetic cardiomyopathy and myocardial infarction, diabetic microangiopathy, diabetic retinopathy, diabetic neuropathy, diabetic nephropathy, diabetic erectile dysfunction, diabetic ulcers on the extremities, diabetic foot ulcers, for promoting diabetic wound healing, and for promoting wound healing of diabetic foot ulcers, in humans and animals by administration of an effective amount of at least one adrenoreceptor α2C receptor antagonist or of a medicament comprising at least one adrenoreceptor α2C receptor antagonist.

The present invention further provides a method for the treatment and/or prophylaxis of diabetic microangiopathies, diabetic retinopathy, diabetic neuropathy, diabetic nephropathy, diabetic erectile dysfunction, diabetic heart failure, diabetic coronary microvascular heart disorders, diabetic ulcers on the extremities, diabetic foot ulcers, for promoting diabetic wound healing, and for promoting wound healing of diabetic foot ulcers.

The present invention further provides a method for the treatment and/or prophylaxis of comorbidities and/or sequelae of diabetes mellitus, diabetic heart disorders, diabetic coronary heart disorders, diabetic coronary microvascular heart disorders, diabetic heart failure, diabetic cardiomyopathy and myocardial infarction, diabetic microangiopathy, diabetic retinopathy, diabetic neuropathy, diabetic nephropathy, diabetic erectile dysfunction, diabetic ulcers on the extremities, diabetic foot ulcers, for promoting diabetic wound healing, and for promoting wound healing of diabetic foot ulcers, in humans and animals by administration of an effective amount of at least one competitive adrenoreceptor α2C receptor antagonist or of a medicament comprising at least one competitive adrenoreceptor α2C receptor antagonist.

Adrenoreceptor α2C receptor antagonists in the context of the present invention are receptor ligands or compounds that block or inhibit the biological responses induced by adrenoreceptor α2C receptor agonists. Adrenoreceptor α2C receptor antagonists in the context of the present invention can be competitive antagonists, non-competitive antagonists, inverse agonists or allosteric modulators.

The compounds according to the invention can be used alone or, if required, in combination with other active compounds. The present invention further provides medicaments comprising a compound according to the invention and one or more further active compounds, in particular for the treatment and/or prophylaxis of the disorders mentioned above. Suitable active compounds for combination are, by way of example and with preference: active compounds which modulate lipid metabolism, antidiabetics, hypotensive agents, perfusion-enhancing and/or antithrombotic agents, and also antioxidants, aldosterone- and mineralocorticoid receptor antagonists, vasopressin receptor antagonists, organic nitrates and NO donors, IP receptor agonists, positively inotropically active compounds, ACE inhibitors, cGMP- and cAMP-modulating compounds, inhibitors of human neutrophile elastase, signal transduction cascade-inhibiting compounds, compounds that modulate the energy metabolism of the heart, chemokine receptor antagonists, p38 kinase inhibitors, NPY agonists, orexin agonists, anorectics, PAF-AH inhibitors, antiphlogistics (COX inhibitors, $LTB_4$ receptor antagonists, inhibitors of $LTB_4$ synthesis), analgesics (aspirin), antidepressants and other psychopharmaceuticals.

The present invention provides in particular combinations of at least one of the compounds according to the invention and at least one lipid metabolism-modulating active compound, antidiabetic, hypotensive active compound and/or antithrombotic agent.

The compounds according to the invention may preferably be combined with one or more of the active compounds mentioned below:

lipid metabolism-modulating active compounds, by way of example and with preference from the group of the HMG-CoA reductase inhibitors from the class of the statins such as, by way of example and with preference, lovastatin, simvastatin, pravastatin, fluvastatin, atorvastatin, rosuvastatin, cerivastatin or pitavastatin, inhibitors of HMG-CoA reductase expression, squalene synthesis inhibitors such as, by way of example and with preference, BMS-188494 or TAK-475, ACAT inhibitors such as, by way of example and with preference, melinamide, pactimibe, eflucimibe or SMP-797, LDL receptor inductors, cholesterol absorption inhibitors such as, by way of example and with preference, ezetimibe, tiqueside or pamaqueside, polymeric bile acid adsorbers such as, by way of example and with preference, cholestyramine, colestipol, colesolvam, CholestaGel or colestimide, bile acid reabsorption inhibitors such as, by way of example and with preference, ASBT (=IBAT) inhibitors such as elobixibat (AZD-7806), S-8921, AK-105, canosimibe (BARI-1741, AVE-5530), SC-435 or SC-635, MTP inhibitors such as, by way of example and with preference, implitapide or JTT-130, lipase inhibitors such as, by way of example and with preference, orlistat, LpL activators, fibrates, niacin, CETP inhibitors such as, by way of example and with preference, torcetrapib, dalcetrapib (JTT-705) or CETP vaccine (Avant), PPAR-γ and/or PPAR-δ agonists such as, by way of example and with preference, pioglitazone or rosiglitazone and/or endurobol (GW-501516), RXR modulators, FXR modulators, LXR modulators, thyroid hormones and/or thyroid mimetics such as, by way of example and with preference, D-thyroxine or 3,5,3'-triiodothyronine (T3), ATP citrate lyase inhibitors, Lp(a) antagonists, cannabinoid receptor 1-antagonists such as, by way of example and with preference, rimonabant or surinabant (SR-147778), leptin receptor agonists, bombesin receptor agonists, histamine receptor agonists, agonists of the niacin receptor such as, by way of example and with preference, niacin, acipimox, acifran or radecol, and the antioxidants/radical scavengers such as, by way of example and with preference, probucol, succinobucol (AGI-1067), BO-653 or AEOL-10150;

antidiabetics mentioned in Die Rote Liste 2014, chapter 12. Antidiabetics are preferably understood as meaning insulin and insulin derivatives and also orally effective hypoglycaemically active compounds. Here, insulin and insulin derivatives include both insulins of animal, human or biotechnological origin and mixtures thereof. The orally effective hypoglycaemically active compounds preferably include sulphonylureas, biguanides, meglitinide derivatives, glucosidase inhibitors and PPAR-gamma agonists. Sulphonylureas which may be mentioned are, by way of example and with preference, tolbutamide, glibenclamide, glimepiride, glipizide or gliclazide, biguanides which may be mentioned are, by way of example and with preference, metformin, meglitinide derivatives which may be mentioned are, by way of example and with preference, repaglinide or nateglinide, glucosidase inhibitors which may be mentioned are, by way of example and with preference, miglitol or acarbose, oxadiazolidinones, thiazolidinediones, GLP 1 receptor agonists, glucagon antagonists, insulin sensitizers, CCK 1 receptor agonists, leptin receptor agonists, inhibitors of liver enzymes involved in the stimulation of gluconeogenesis and/or glycogenolysis, modulators of glucose uptake and potassium channel openers such as, for example, those disclosed in WO 97/26265 and WO 99/03861;

hypotensive active compounds, by way of example and with preference from the group of the calcium antagonists such as, by way of example and with preference, nifedipine, amlodipine, verapamil or diltiazem, angiotensin AII antagonists such as, by way of example and with preference, losartan, valsartan, candesartan, embusartan or telmisartan, ACE inhibitors such as, by way of example and with preference, enalapril, captopril, ramipril, delapril, fosinopril, quinopril, perindopril or trandopril, beta receptor blockers such as, by way of example and with preference, propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol, alpha receptor blockers such as, by way of example and with preference, prazosin, ECE inhibitors, rho-kinase inhibitors and of the vasopeptidase inhibitors, and also of the diuretics such as, by way of example and with preference, a loop diuretic such as furosemide, bumetanide or torsemide, or a thiazide or thiazide-like diuretic such as chlorothiazide or hydrochlorothiazide or A1 antagonists such as rolofylline, tonopofylline and SLV-320;

agents which lower the symphathetic tone such as, by way of example and with preference, reserpin, clonidine or alpha-methyldopa, or in combination with a potassium channel agonist such as, by way of example and with preference, minoxidil, diazoxide, dihydralazine or hydralazine;

antithrombotic agents such as, by way of example and with preference, from the group of the platelet aggregation inhibitors such as, by way of example and with preference, aspirin, clopidogrel, ticlopidine, cilostazol or dipyridamole, or of the anticoagulants such as thrombin inhibitors such as, by way of example and with preference, ximelagatran, melagatran, bivalirudin or clexane, a GPIIb/IIIa antagonist such as, by way of example and with preference, tirofiban or abciximab, a factor Xa inhibitor such as, by way of example and with preference, rivaroxaban, edoxaban (DU-176b), apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428, with heparin or a low molecular weight (LMW) heparin derivative or with a vitamin K antagonist such as, by way of example and with preference, coumarin;

aldosterone and mineralocorticoid receptor antagonists such as, by way of example and with preference, spironolactone, eplerenone or finerenone;

vasopressin receptor antagonists such as, by way of example and with preference, conivaptan, tolvaptan, lixivaptan or satavaptan (SR-121463);

organic nitrates and NO donors such as, by way of example and with preference, sodium nitroprusside, nitroglycerol, isosorbide mononitrate, isosorbide dinitrate, molsidomine or SIN-1, or in combination with inhalative NO;

IP receptor agonists, such as, by way of example and with preference, iloprost, treprostinil, beraprost and selexipag (NS-304);

positive inotropic compounds, such as, by way of example and with preference, cardiac glycosides (digoxin), beta-adrenergic and dopaminergic agonists such as isoproterenol, adrenaline, noradrenaline, dopamine and dobutamine;

calcium sensitizers, by way of example and with preference levosimendan;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil and tadalafil, and PDE 3 inhibitors such as milrinone;

natriuretic peptides, for example atrial natriuretic peptide (ANP, anaritide), B-type natriuretic peptide or brain natriuretic peptide (BNP, nesiritide), C-type natriuretic peptide (CNP) and urodilatin;

NO-independent but haem-dependent stimulators of guanylate cyclase, such as especially the compounds described in WO 00/06568, WO 00/06569, WO 02/42301 and WO 03/095451;

NO- and haem-independent activators of guanylate cyclase, such as especially the compounds described in WO 01/19355, WO 01/19776, WO 01/19778, WO 01/19780, WO 02/070462 and WO 02/070510;

inhibitors of human neutrophil elastase (HNE), for example sivelestat and DX-890 (Reltran);

compounds which inhibit the signal transduction cascade, for example tyrosine kinase inhibitors and multikinase inhibitors, especially sorafenib, imatinib, gefitinib and erlotinib; and/or compounds which influence the energy metabolism of the heart, for example etomoxir, dichloroacetate, ranolazine and trimetazidine.

In the context of the present invention, particular preference is given to combinations comprising at least one of the compounds according to the invention and one or more further active compounds selected from the group consisting of HMG-CoA reductase inhibitors (statins), diuretics, beta-receptor blockers, organic nitrates and NO donors, ACE inhibitors, angiotensin AII antagonists, aldosterone and mineralocorticoid receptor antagonists, vasopressin receptor antagonists, platelet aggregation inhibitors and anticoagulants, and also their use for the treatment and/or prevention of the disorders mentioned above.

Particular preference in the context of the present invention is given to combinations comprising at least one of the compounds according to the invention and one or more further active compounds selected from the group consisting of heparin, antidiabetics, ACE inhibitors, diuretics and antibiotics, and also to their use in a method for promoting diabetic wound healing and for the treatment and/or prevention of diabetic ulcers on the extremities, in particular for promoting wound healing of diabetic foot ulcers.

Particular preference in the context of the present invention is given to the use of at least one of the compounds according to the invention in a method for promoting diabetic wound healing and for the treatment and/or prevention of diabetic ulcers on the extremities, in particular for promoting wound healing of diabetic foot ulcers, where the compound of the formula (I) is additionally employed for one or more of the following physical and/or topical therapies: wound management such as dressings, wound excision, weight reduction with appropriate footwear, PDGF (Regranex), hyperbaric oxygen therapy, wound therapy with negative pressure.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds of the invention can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

Oral administration is preferred.

In the exemplary use of the compounds of the formula (I) for promoting diabetic wound healing, in particular for promoting wound healing of diabetic foot ulcers, preference, in addition to oral administration, is also given to administration in the form of a topical formulation.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The compounds of the invention can be converted to the administration forms mentioned. This can be accomplished in a manner known per se by mixing with inert non-toxic pharmaceutically suitable auxiliaries. These auxiliaries include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

The present invention further provides medicaments comprising at least one inventive compound, preferably together with one or more inert non-toxic pharmaceutically suitable auxiliaries, and the use thereof for the purposes mentioned above.

In general, it has been found to be advantageous in the case of oral administration to administer amounts of from about 0.1 to 250 mg per 24 hours, preferably 0.1 to 50 mg per 24 hours, to achieve effective results. The dose may be divided into a plurality of administrations per day. Examples are administrations twice or three times per day.

It may nevertheless be necessary in some cases to deviate from the stated amounts, specifically as a function of body weight, route of administration, individual response to the active compound, nature of the preparation and time or interval over which administration takes place.

The present invention further provides a compound of the formula (I) as described above for use in a method for the treatment and/or prophylaxis of primary and secondary forms of diabetic microangiopathies, diabetic wound healing, diabetic ulcers on the extremities, in particular for promoting wound healing of diabetic foot ulcers, diabetic retinopathy, diabetic nephropathy, diabetic erectile dysfunction, diabetic heart failure, diabetic coronary microvascular heart disorders, peripheral and cardiac vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies.

The present invention further provides a compound of the formula (I) as described above for use in a method for the treatment and/or prophylaxis of primary and secondary forms of heart failure, peripheral and cardiovascular disorders, thromboembolic disorders and ischaemias, peripheral circulatory disturbances, Raynaud's phenomenon, microcirculatory disturbances, intermittent claudication, peripheral and autonomous neuropathies, and CREST syndrome, and also for diabetic wound healing, in particular for promoting wound healing of diabetic foot ulcers.

The present invention further provides a compound of the formula (I) as described above for preparing a medicament for the treatment and/or prophylaxis of primary and secondary forms of diabetic microangiopathies, diabetic wound healing, diabetic ulcers on the extremities, in particular for promoting wound healing of diabetic foot ulcers, diabetic retinopathy, diabetic nephropathy, diabetic erectile dysfunction, diabetic heart failure, diabetic coronary microvascular heart disorders, peripheral and cardiac vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies.

The present invention further provides the use of a compound of the formula (I) as described above for preparing a medicament for the treatment and/or prophylaxis of primary and secondary forms of heart failure, peripheral and cardiovascular disorders, thromboembolic disorders and ischaemias, peripheral circulatory disturbances, Raynaud's phenomenon, microcirculatory disturbances, intermittent claudication, peripheral and autonomous neuropathies, and CREST syndrome, and also for diabetic wound healing, in particular for promoting wound healing of diabetic foot ulcers.

The present invention further provides a medicament comprising a compound of the formula (I) as described above in combination with one or more inert non-toxic pharmaceutically suitable auxiliaries.

The present invention further provides a medicament comprising a compound of the formula (I) as described above in combination with one or more further active compounds selected from the group consisting of lipid metabolism-modulating active compounds, antidiabetics, hypotensive agents, agents which lower the sympathetic tone, perfusion-enhancing and/or antithrombotic agents and also antioxidants, aldosterone and mineralocorticoid receptor antagonists, vasopressin receptor antagonists, organic nitrates and NO donors, IP receptor agonists, positive inotropic compounds, calcium sensitizers, ACE inhibitors, cGMP- and cAMP-modulating compounds, natriuretic peptides, NO-independent stimulators of guanylate cyclase, NO-independent activators of guanylate cyclase, inhibitors of human neutrophil elastase, compounds which inhibit the signal transduction cascade, compounds which modulate the energy metabolism of the heart, chemokine receptor antagonists, p38 kinase inhibitors, NPY agonists, orexin agonists, anorectics, PAF-AH inhibitors, antiphlogistics, analgesics, antidepressants and other psychopharmaceuticals.

The present invention further provides a medicament as described above for the treatment and/or prophylaxis of primary and secondary forms of diabetic microangiopathies, diabetic wound healing, diabetic ulcers on the extremities, in particular for promoting wound healing of diabetic foot ulcers, diabetic retinopathy, diabetic nephropathy, diabetic erectile dysfunction, diabetic heart failure, diabetic coronary microvascular heart disorders, peripheral and cardiac vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies.

The present invention further provides a medicament as described above for the treatment and/or prophylaxis of primary and secondary forms of heart failure, peripheral and cardiovascular disorders, thromboembolic disorders and ischaemias, peripheral circulatory disturbances, Raynaud's phenomenon, microcirculatory disturbances, intermittent claudication, peripheral and autonomous neuropathies, and CREST syndrome, and also for diabetic wound healing, in particular for promoting wound healing of diabetic foot ulcers.

The present invention further provides a method for the treatment and/or prophylaxis of primary and secondary forms of diabetic microangiopathies, diabetic wound healing, diabetic ulcers on the extremities, in particular for promoting wound healing of diabetic foot ulcers, diabetic retinopathy, diabetic nephropathy, diabetic erectile dysfunction, diabetic heart failure, diabetic coronary microvascular heart disorders, peripheral and cardiac vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies in humans and animals by administration of an effective amount of at least one compound of the formula (I) as described above or of a medicament as described above.

The present invention further provides a method for the treatment and/or prophylaxis of primary and secondary forms of heart failure, peripheral and cardiovascular disorders, thromboembolic disorders and ischaemias, peripheral circulatory disturbances, Raynaud's phenomenon, microcirculatory disturbances, intermittent claudication, peripheral and autonomous neuropathies, and CREST syndrome, and also for diabetic wound healing, in particular for promoting wound healing of diabetic foot ulcers, in humans and animals by administration of an effective amount of at least one compound of the formula (I) as described above or of a medicament as described above.

Unless stated otherwise, the percentages in the tests and examples which follow are percentages by weight; parts are parts by weight. Solvent ratios, dilution ratios and concentration data for the liquid/liquid solutions are based in each case on volume. "w/v" means "weight/volume". For example, "10% w/v" means: 100 ml of solution or suspension comprise 10 g of substance.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "oxalate salt", "sodium salt" or "×HCl", "×CF3COOH", "×C2O42-", "×Na+" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

A) EXAMPLES

Abbreviations

Å Angström
br. broad signal (in NMR)
d day(s), doublet (in NMR)
TLC thin-layer chromatography
dd doublet of doublets (in NMR)
DMAP 4-dimethylaminopyridine
DMF N,N-dimethylformamide
DMSO dimethyl sulphoxide
EDC 1-(3-dimethylaminopropyl)-3-ethylcarbodiimide hydrochloride
eq. equivalent(s)
ESI electrospray ionization (in MS)
wt % percent by weight
h hour(s)
HATU O-(7-azabenzotriazol-1-yl)-N,N,N',N'-tetramethyluronium hexafluorophosphate
HOBT 1-hydroxy-1H-benzotriazole hydrate
HPLC high-pressure, high-performance liquid chromatography
HV high vacuum
LC-MS liquid chromatography-coupled mass spectroscopy
sol. solution
m multiplet (in NMR)
min minute(s)
MS mass spectroscopy
NMR nuclear magnetic resonance spectroscopy
q quartet (in NMR)
Rf retention factor (in TLC)
RP reversed phase (in HPLC)
RT room temperature
$R_t$ retention time (in HPLC)
s singlet (in NMR)
t triplet (in NMR)
T3P propylphosphonic anhydride 50% strength in ethyl acetate or DMF
THF tetrahydrofuran
UV ultraviolet LC-MS and HPLC Methods:

Method 1 (LC-MS):
Instrument: Waters ACQUITY SQD UPLC system; column: Waters Acquity UPLC HSS T3 1.8µ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 2 (LC-MS):
Instrument: Waters ACQUITY SQD UPLC system; column: Waters Acquity UPLC HSS T3 1.8µ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 210-400 nm.

Method 3 (LC-MS):
Instrument: Waters ACQUITY SQD UPLC system; column: Waters Acquity UPLC HSS T3 1.8µ 30×2 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.60 ml/min; UV detection: 208-400 nm.

Method 4 (LC-MS):
Instrument: Micromass Quattro Premier with Waters UPLC Acquity; column: Thermo Hypersil GOLD 1.9µ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; oven: 50° C.; flow rate: 0.33 ml/min; UV detection: 210 nm.

Method 5 (LC-MS):
MS instrument: Waters (Micromass) Quattro Micro; HPLC instrument type: Agilent 1100 series; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.01 min 100% A (flow rate: 2.5 ml)→5.00 min 100% A; oven: 50° C.; flow rate: 2 ml/min; UV detection: 210 nm.

Method 6 (LC-MS):
MS instrument type: Waters ZQ; HPLC instrument type: Agilent 1100 Series; UV DAD; column: Thermo Hypersil GOLD 3µ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→3.0 min 10% A→4.0 min 10% A→4.1 min 100%; oven: 55° C.; flow rate: 2 ml/min; UV detection: 210 nm.

Method 7 (LC-MS):

MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 8 (LC-MS):

MS instrument: Waters (Micromass) Quattro Micro; HPLC instrument: Agilent 1100 series; column: YMC-Triart C18 3μ 50×3 mm; mobile phase A: 1 l of water+0.01 mol of ammonium carbonate, mobile phase B: 1 l of acetonitrile; gradient: 0.0 min 100% A→2.75 min 5% A→4.5 min 5% A; oven: 40° C.; flow rate: 1.25 ml/min; UV detection: 210 nm.

Method 9 (preparative HPLC):

column: Waters XBridge, 50×19 mm, 10 am, mobile phase A: water+0.5% ammonium hydroxide, mobile phase B: acetonitrile, 5 min=95% A, 25 min=50% A, 38 min=50% A, 38.1 min=5% A, 43 min=5% A, 43.01 min=95% A, 48.0 min=5% A; flow rate 20 ml/min, UV detection: 210 nm.

Method 10 (preparative HPLC):

column: Chromatorex C18, 250×20 mm, 10 am; mobile phase A: water+0.5% formic acid, mobile phase B: acetonitrile, gradient: 0.0 min 95% A→3.0 min 95% A→25 min 70% A→38 min 70% A→38.1 min 95% A; flow rate: 20 ml/min; UV detection: 210 nm.

Method 11 (Preparative HPLC):

column: XBridge, 50×19 mm, 10 am, isocratic 40% water, 55% methanol, 5% 1% strength ammonium hydroxide; flow rate 20 ml/min, UV detection: 210 nm.

Method 12 (Preparative HPLC):

column: XBridge, 150×19 mm, 10 am, mobile phase A: water, mobile phase B: acetonitril, mobile phase C: constant+5% 1% strength ammonium hydroxide, 0.0 min 80% A→1 min=80% A→6.5 min=0% A→7.5 min 0% A→7.6 min 80% A→12.0 min 80% A; flow rate 25 ml/min, UV detection: 210 nm.

Method 13 (Preparative HPLC):

column: Waters XBridge, 50×19 mm, 10 am, mobile phase A: water+0.5% ammonium hydroxide, mobile phase B: acetonitrile, 0.0 min 95% A→5.0 min=95% A→25 min=70% A→38 min=70% A→38.1 min=5% A→43 min=5% A→43.01 min=95% A→48.0 min=95% A; flow rate 20 ml/min, UV detection: 210 nm.

Method 14 (Preparative HPLC):

column: XBridge, 50×19 mm, 10 μm, mobile phase A: water, mobile phase B: acetonitril, mobile phase C: constant+0.1% ammonium hydroxide, 0.0 min 48% A→8.30 min=48% A→8.35 min=0% A→9.15 min 0% A→9.20 min 48% A→11.00 min 48% A; flow rate 25 ml/min, UV detection: 210 nm.

The microwave reactor used was an instrument of the Biotage Initiator™ type.

The NMR data were assigned unless the signals were concealed by solvent.

Starting Materials

Example 1A tert-Butyl (3R)-3-methyl-1,4'-bipiperidine-1'-carboxylate hydrochloride 12.89 g (64.7 mmol) of tert-butyl 4-oxopiperidine-1-carboxylate together with 7.70 g (77.6 mmol) of (3R)-3-methylpiperidine and about 2 g of molecular sieve 3 Å in 220 ml of dichloromethane were stirred at RT for 1 h. 20.6 g (97.0 mmol) of sodium triacetoxyborohydride were then added to this suspension, and the mixture was stirred at RT for a further 16 h. For work-up, the mixture was diluted with 200 ml of dichloromethane and washed twice with in each case 100 ml of saturated sodium bicarbonate solution. The aqueous phase was extracted once with 100 ml of dichloromethane and the combined organic phases were washed twice with in each case 100 ml of saturated sodium chloride solution. The organic phase was dried over sodium sulphate, filtered and concentrated under reduced pressure. The residue obtained was dissolved using about 50 ml of dichloromethane, and 20 ml of 4M hydrogen chloride in dioxane were added. The mixture was stirred for another 10 min approximately and then concentrated by evaporation, and the solid residue obtained was triturated with diethyl ether. The product was filtered off with suction, washed with ether and dried under HV. This gave 10.7 g (49% of theory) of the target compound.

LC-MS [Method 2]: $R_t$=0.54 min; MS (ESIpos): m/z=283 (M+H)$^+$

Example 2A (3R)-3-Methyl-1,4'-bipiperidine dihydrochloride 196 g (615 mmol) of the compound from Example 1A were dissolved in 1.2 l of dichloromethane, and 230 ml (922 mmol) of 4M hydrogen chloride in dioxane were added, with the temperature of the mixture being kept at 25-30° C. The product started to crystallize after the addition was about ⅓ complete. The mixture was then stirred at RT for 20 h. To bring the reaction to completion, a further 154 ml (614 mmol) 4M of 4M hydrogen chloride in dioxane were added. The mixture was stirred at RT for another 6 h, and 500 ml of tert-butyl methyl ether were then added. The resulting precipitate was filtered off, washed twice with in each case about 400 ml of tert-butyl methyl ether and dried under reduced pressure at about 60° C. This gave 154 g (97% of theory) of the target product.

¹H-NMR (400 MHz, DMSO-d₆): δ [ppm]=0.90 (d, 3H), 1.01-1.17 (m, 1H), 1.65-2.12 (m, 5H), 2.18-2.35 (m, 2H), 2.73-2.98 (m, 3H), 3.21-3.47 (m, 4H), 8.96 (br. s., 1H), 9.12 (br. s., 1H), 10.86 (br. s., 1H).

Example 3A tert-Butyl 4-[3-(cyclopropylmethoxy)piperidin-1-yl]-3,6-dihydropyridine-1(2H)-carboxylate

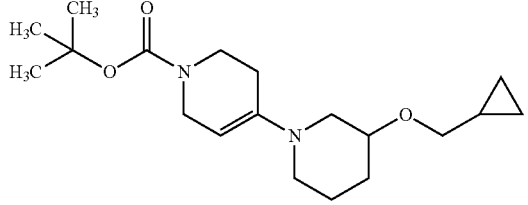 [SMILES: CC(C)(C)OC(=O)N1CC=C(N2CCCC(OCC3CC3)C2)CC1]

4.89 g (24.5 mmol) of tert-butyl 4-oxopiperidine-1-carboxylate together with 4.70 g (24.5 mmol) of 3-(cyclopropylmethoxy)piperidine hydrochloride and 93 mg (0.49 mmol) of p-toluenesulphonic acid in 40 ml of toluene were heated under reflux on a water separator for 18 h. After cooling to RT, the solvent was evaporated under reduced pressure and the residue was dried under high vacuum. This gave 8.25 g (100% of theory) of the product which was converted further without further purification.

Example 4A tert-Butyl 3-(cyclopropylmethoxy)-1,4'-bipiperidine-1'-carboxylate hydrochloride

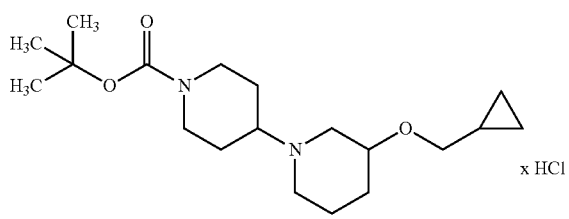 [SMILES: CC(C)(C)OC(=O)N1CCC(N2CCCC(OCC3CC3)C2)CC1]

8.25 g (24.5 mmol) of the compound from Example 3A were dissolved in 75 ml of ethyl acetate, and 1.00 g of palladium on carbon (10%) was added. The mixture was stirred under atmospheric pressure at RT for 18 h. Subsequently, the mixture was filtered through kieselguhr, the kieselguhr was washed with ethyl acetate and the filtrate was concentrated under reduced pressure. The residue was dissolved in about 50 ml of diethyl ethyl, and 6.2 ml of 4M hydrogen chloride in dioxane were added. The resulting precipitate was stirred for about 5 min, filtered off and washed with diethyl ether. Drying under high vacuum gave 5.90 g (64% of theory) of the desired product.

LC-MS [Method 2]: R$_t$=0.66 min; MS (ESIpos): m/z=339 (M+H)⁺

¹H-NMR (400 MHz, DMSO-d₆): δ [ppm]=0.10-0.25 (m 2H), 0.41-0.51 (m, 2H), 0.91-1.08 (m, 1H), 1.21-1.33 (m, 1H), 1.40 (s, 9H), 1.48-1.62 (m, 2H), 1.65-2.12 (m, 5H), 2.58-2.85 (m, 3H), 2.98-3.10 (m, 1H), 3.20-3.50 (m, 5H), 3.71-3.82 (m, 1H), 3.95-4.13 (m, 2H), 8.92 and 10.72 (br. 2s, 1H).

Example 5A 3-(Cyclopropylmethoxy)-1,4'-bipiperidine dihydrochloride

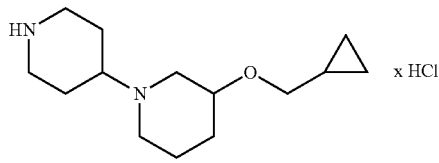 [SMILES: C1CC(OCC2CC2)CN(C2CCNCC2)C1]

5.90 g (15.7 mmol) of the compound from Example 4A were dissolved in 80 ml of dichloromethane, and 79 ml (19.7 mmol) of 4M hydrogen chloride in dioxane were added, with the temperature of the mixture being kept at 25-30° C. The product started to crystallize after the addition was about ⅓ complete. The mixture was then stirred at RT for 22 h. For work-up, the solvent was removed under reduced pressure and the residue was stirred with about 50 ml of diethyl ether. The resulting precipitate was filtered off, washed with in each case about 50 ml of diethyl ether and dried under reduced pressure at about 40° C. This gave 4.64 g (95% of theory) of the target product.

¹H-NMR (400 MHz, DMSO-d₆): δ [ppm]=0.10-0.30 (m 2H), 0.41-0.53 (m, 2H), 0.92-1.10 (m, 1H), 1.26-1.41 (m, 1H), 1.52-1.75 (m, 1H), 1.77-2.40 (m, 8H), 2.62-2.75 (m, 1H), 2.78-2.98 (m, 3H), 3.00-3.19 (m, 1H), 3.21-3.47 (m, 4H), 3.80-3.90 (m, 1H), 8.85-9.40 (br. m, 2H), 11.30 (br. s., 1H).

Example 6A

6-[(2-Methoxyethyl)amino]nicotinic acid

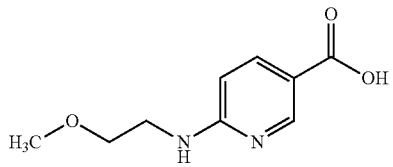

5.00 g (31.7 mmol) of 6-chloronicotinic acid, 27.6 ml (317 mmol) of 2-methoxyethylamine and 35 ml of 2-propanol were, divided into 5 portions, heated in the microwave at 180° C. for 1 h. After cooling to RT, the batches were combined, stirred with 500 ml of tert-butyl methyl ether and filtered off. The solid was taken up in 30 ml of water and acidified to pH 4 using 10% strength acetic acid, and the resulting precipitate was filtered off with suction, washed with tert-butyl methyl ether and dried under HV, giving 2.20 g (35% of theory) of the title compound. After concentration of the filtrate to about ⅓ of the solvent volume, crystallization gave a further 1.00 g (16% of theory) of the title compound.

¹H-NMR (400 MHz, DMSO-d₆): δ [ppm]=2.81 (td, 2H), 3.40 (td, 2H), 3.45 (br. s., 3H), 6.41-6.52 (m, 1H), 7.07 (br. s., 1H), 7.76 (d, 1H), 8.49 (s, 1H).

Example 7A 6-(Morpholin-4-yl)nicotinic acid

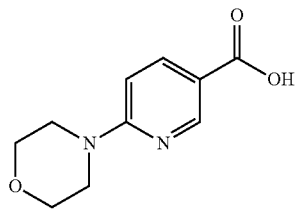 [SMILES: O=C(O)c1ccc(N2CCOCC2)nc1]

A mixture of 5.00 g (31.7 mmol) of 6-chloronicotinic acid and 27.7 ml (317 mmol) of morpholine was heated under reflux for 18 h. After cooling to RT, the mixture was stirred with tert-butyl methyl ether and filtered off. The solid was taken up in a little water and acidified to pH 4 using 10% strength acetic acid, and the resulting precipitate was filtered off with suction, washed with tert-butyl methyl ether and dried in a vacuum drying cabinet, giving 5.94 g (85% of theory) of the title compound.

LC-MS [Method 8]: $R_t$=1.35 min; MS (ESIpos): m/z=209 (M+H)⁺

¹H-NMR (400 MHz, DMSO-d₆): δ [ppm]=3.55-3.63 (m, 4H), 3.64-3.73 (m, 4H), 6.86 (d, 1H), 7.95 (dd, 1H), 8.64 (d, 1H), 11.53-13.28 (m, 1H).

Example 8A (6-Chloropyridin-3-yl)[(3R)-3-methyl-1,4'-bipiperidin-1'-yl]methanone hydrochloride

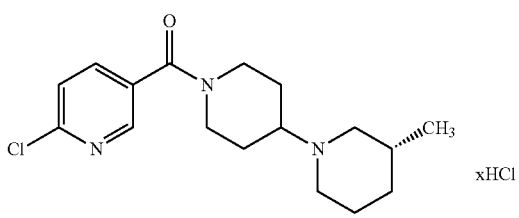 [SMILES: C[C@@H]1CCCN(C2CCN(C(=O)c3ccc(Cl)nc3)CC2)C1]

17.1 ml (98 mmol) of N,N-diisopropylethylamine were added to a mixture of 3.09 g (19.6 mmol) of 6-chloronicotinic acid and 5.00 g (19.6 mmol) of (3R)-3-methyl-1,4'-bipiperidine dihydrochloride in 39 ml of acetonitrile. 13.7 ml (23.5 mmol) of T3P (50% by weight strength solution in ethyl acetate) were then added dropwise, and the mixture was stirred at RT for 18 h. For work-up, saturated sodium bicarbonate solution was added and the mixture was stirred for 30 min and then extracted three times with dichloromethane. The combined organic phases were washed with saturated sodium chloride solution, dried over magnesium sulphate, filtered and concentrated. The residue was dissolved in a little dichloromethane, and 5 ml of 4N hydrochloric acid in dioxane were added. The mixture was concentrated and stirred with tert-butyl methyl ether and the precipitate formed was filtered off and dried in a vacuum drying cabinet at 50° C. This gave 5.95 g (81% of theory) of the title compound.

LC-MS [Method 1]: $R_t$=0.42 min; MS (ESIpos): m/z=322 (M+H)⁺

¹H-NMR (400 MHz, DMSO-d₆): δ [ppm]=0.90 (d, 3H), 0.97-1.16 (m, 1H), 1.60-2.30 (m, 8H), 2.70-2.96 (m, 2H), 3.00-3.22 (m, 1H), 3.39-3.51 (m, 1H), 3.56-3.72 (m, 1H), 4.44-4.74 (m, 1H), 7.64 (d, 1H), 7.94 (dd, 1H), 8.50 (d, 1H), 10.48-10.70 (br s, 1H).

Example 9A (6-Fluoropyridin-3-yl)[(3R)-3-methyl-1,4'-bipiperidin-1'-yl]methanone

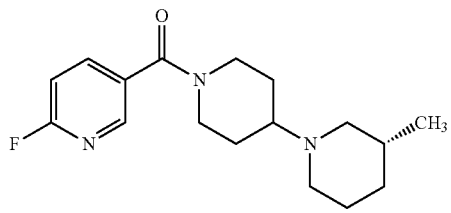 [SMILES: C[C@@H]1CCCN(C2CCN(C(=O)c3ccc(F)nc3)CC2)C1]

18.5 ml (106 mmol) of N,N-diisopropylethylamine were added to a mixture of 3.00 g (21.3 mmol) of 6-fluoronicotinic acid and 5.43 g (21.3 mmol) of (3R)-3-methyl-1,4'-bipiperidine dihydrochloride in 72 ml of acetonitrile. 14.9 ml (25.5 mmol) of T3P (50% by weight strength solution in ethyl acetate) were then added dropwise, and the mixture was stirred at RT for 18 h. For work-up, 20 ml of saturated sodium bicarbonate solution were added, the mixture was stirred for 30 min, the organic phase was concentrated and the residue was extracted twice with ethyl acetate. The combined organic phases were washed with saturated sodium chloride solution, dried over magnesium sulphate, filtered, concentrated and dried under HV. This gave 5.70 g (88% of theory) of the title compound.

LC-MS [Method 8]: $R_t$=2.35 min; MS (ESIpos): m/z=306 (M+H)⁺

¹H-NMR (400 MHz, DMSO-d₆): δ [ppm]=0.74-0.88 (m, 4H), 1.33-1.87 (m, 9H), 2.00-2.12 (m, 1H), 2.70-2.83 (m, 3H), 2.93-3.13 (m, 1H), 3.45-3.63 (m, 1H), 4.41-4.57 (m, 1H), 7.26 (dd, 1H), 8.05 (td, 1H), 8.31 (d, 1H).

Example 10A (6-Bromopyridin-3-yl)[(3R)-3-methyl-1,4'-bipiperidin-1'-yl]methanone

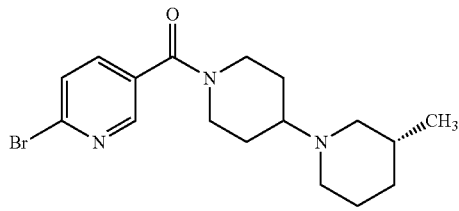 [SMILES: C[C@@H]1CCCN(C2CCN(C(=O)c3ccc(Br)nc3)CC2)C1]

8.64 ml (49.5 mmol) of N,N-diisopropylethylamine were added to a mixture of 2.00 g (9.90 mmol) of 6-bromonicotinic acid and 2.53 g (9.90 mmol) of (3R)-3-methyl-1,4'-bipiperidine dihydrochloride in 20 ml of acetonitrile. 6.94 ml (11.9 mmol) of T3P (50% by weight strength solution in ethyl acetate) were then added dropwise, and the mixture was stirred at RT for 18 h. For work-up, 50 ml of saturated sodium bicarbonate solution were added and the mixture was stirred for 30 min and then extracted twice with dichloromethane. The combined organic phases were washed with saturated sodium bicarbonate solution and water, dried over magnesium sulphate, filtered, concentrated and dried under HV. This gave 3.40 g (93% of theory) of the title compound.

LC-MS [Method 1]: $R_t$=0.48 min; MS (ESIpos): m/z=366 and 368 (M+H)$^+$ $^1$H-NMR (400 MHz, DMSO-d$_6$): δ [ppm]=0.72-0.88 (m, 4H), 1.30-1.86 (m, 9H), 2.00-2.16 (m, 1H), 2.67-2.83 (m, 3H), 2.95-3.11 (m, 1H), 3.44-3.61 (m, 1H), 4.35-4.58 (m, 1H), 7.70-7.75 (m, 1H), 7.77-7.82 (m, 1H), 8.44 (d, 1H).

Example 11A

Methyl 2-(2-oxa-6-azaspiro[3.3]hept-6-yl)pyrimidine-5-carboxylate

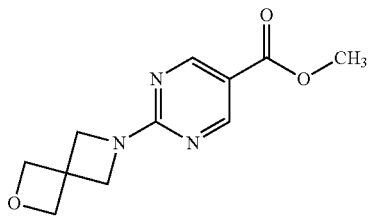 [SMILES: COC(=O)c1cnc(N2CC3(COC3)C2)nc1]

14.70 g (85.18 mmol) of methyl 2-chloropyrimidine-5-carboxylate were dissolved in 200 ml of acetonitrile, and 41.20 mg of potassium carbonate (298.14 mmol) were added. 24.17 g (127.77 mmol) of 2-oxa-6-azaspiro[3.3]heptane oxalate salt, prepared according to Angew. Chem. Int. Ed. 2008, 47, 4512-4515, were then added, and the mixture was stirred at 60° C. for about 16 h. The mixture was then stirred with water and extracted three times with in each case 200 ml of ethyl acetate. The aqueous phase was then extracted once with about 200 ml of dichloromethane. The combined organic phases were dried over sodium sulphate, filtered and concentrated. The residue was stirred with about 200 ml of diethyl ether. The precipitated solid was filtered off with suction, washed with a little diethyl ether and dried under HV. This gave 17.70 g (88% of theory) of the target compound.

LC-MS [Method 1]: $R_t$=0.61 min; MS (ESIpos): m/z=236 (M+H)$^+$ $^1$H-NMR (400 MHz, DMSO-d$_6$): δ [ppm]=3.33 (s, 3H), 4.32 (s, 4H), 4.73 (s, 4H), 8.70-8.81 (m, 2H).

Example 12A 2-(2-Oxa-6-azaspiro[3.3]hept-6-yl)pyrimidine-5-carboxylic acid

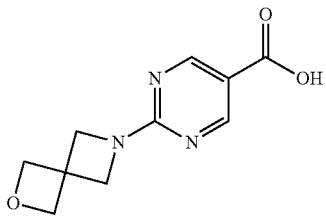 [SMILES: O=C(O)c1cnc(N2CC3(COC3)C2)nc1]

17.7 g (75 mmol) of the compound from example 11A were initially charged in 120 ml of ethanol, 148 ml of 1 molar sodium hydroxide solution were added and the mixture was stirred at RT for 18 h. The mixture was concentrated and then initially dissolved in about 150 ml of water and then adjusted to pH 5 with 1 M hydrochloric acid. The precipitated product was filtered off with suction and washed with water. This gave 16.3 g of product (98% of theory).

LC-MS [Method 7]: $R_t$=0.53 min; MS (ESIpos): m/z=222 (M+H)$^+$ $^1$H-NMR (400 MHz, DMSO-d$_6$): δ [ppm]=4.30 (s, 4H), 4.73 (s, 4H), 8.74 (s, 2H), 12.87 (br. s, 1H).

Example 13A

Ethyl 2-[(2R)-2-(tert-butoxycarbonyl)pyrrolidin-1-yl]pyrimidine-5-carboxylate

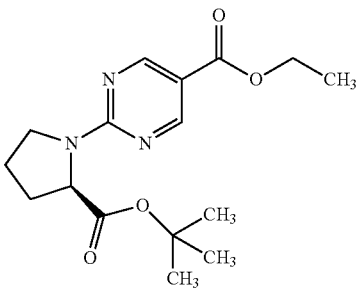 [SMILES: CCOC(=O)c1cnc(N2CCC[C@@H]2C(=O)OC(C)(C)C)nc1]

818 mg (4.78 mmol) of t-butyl D-prolinate were added dropwise to a suspension of 1.00 g (4.34 mmol) of ethyl 2-(methylsulphonyl)pyrimidine-5-carboxylate and 2.40 g (17.4 mmol) of potassium carbonate in 10 ml of acetonitrile. After stirring at RT for 18 h, the reaction mixture was diluted with ethyl acetate and filtered off, the residue was washed with ethyl acetate/dichloromethane and the filtrate was concentrated. The crude product was purified chromatographically on silica gel (elution with cyclohexane/ethyl acetate 95:5-70:30), which gave 564 mg (40% of theory) of the title compound.

LC-MS [Method 1]: $R_t$=1.19 min; MS (ESIpos): m/z=322 (M+H)$^+$ $^1$H-NMR (400 MHz, DMSO-d$_6$): δ [ppm]=1.29 (t, 3H), 1.37 (s, 9H), 1.87-2.04 (m, 3H), 2.26-2.39 (m, 1H), 3.57-3.75 (m, 2H), 4.27 (q, 2H), 4.44-4.48 (m, 1H), 8.74 (d, 1H), 8.83 (d, 1H).

Example 14A

2-[(2R)-2-(tert-Butoxycarbonyl)pyrrolidin-1-yl]pyrimidine-5-carboxylic acid

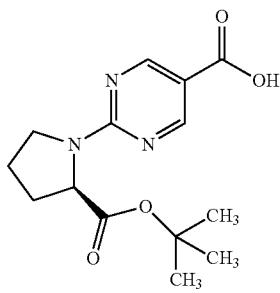 [SMILES: CC(C)(C)OC(=O)[C@H]1CCCN1c1ncc(C(=O)O)cn1]

8.6 ml of a 1N solution of lithium hydroxide were added to a solution of 564 mg (1.76 mmol) of the compound from Example 13A in 20 ml of THF/methanol (5:1), and the mixture was stirred at RT for 18 h. For workup, the reaction mixture was concentrated, acidified with 6N hydrochloric acid and concentrated. The residue obtained was triturated with water. The precipitated solid was filtered off, washed with water, and dried in a vacuum drying cabinet at 50° C. This gave 400 mg (78% of theory) of the title compound.

LC-MS [Method 1]: $R_t$=0.90 min; MS (ESIpos): m/z=294 (M+H)$^+$ $^1$H-NMR (400 MHz, DMSO-d$_6$): δ [ppm]=1.37 (s, 9H), 1.87-2.04 (m, 3H), 2.25-2.37 (m, 1H), 3.56-3.73 (m, 2H), 4.41-4.49 (m, 1H), 8.71 (d, 1H), 8.81 (d, 1H), 12.41-13.33 (br. s, 1H).

Example 15A tert-Butyl 1-(5-{[(3R)-3-methyl-1,4'-bipiperidin-1'-yl]carbonyl}pyrimidin-2-yl)-D-prolinate

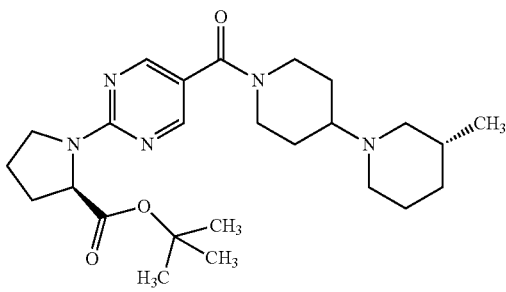 [SMILES: C[C@@H]1CCCN(C2CCN(C(=O)c3cnc(N4CCC[C@@H]4C(=O)OC(C)(C)C)nc3)CC2)C1]

0.42 ml (2.39 mmol) of N,N-diisopropylethylamine was added to a mixture of 100 mg (0.34 mmol) of the compound from Example 14A and 87 mg (0.34 mmol) of the compound from Example 2A in 3 ml of acetonitrile. 0.24 ml (0.41 mmol) of T3P (50% by weight strength solution in ethyl acetate) were then added dropwise, and the mixture was stirred at RT for 18 h. For work-up, 1 ml of saturated sodium bicarbonate solution was added, the mixture was stirred for 15 min and then filtered through an Extrelut cartridge and eluted with dichloromethane, and the filtrate was concentrated. The residue was purified by preparative HPLC [Method 9], giving 115 mg (73% of theory) of the title compound.

LC-MS [Method 8]: $R_t$=3.16 min; MS (ESIpos): m/z=458 (M+H)$^+$ $^1$H-NMR (400 MHz, DMSO-d$_6$): δ [ppm]=0.73-0.89 (m, 4H), 1.28-1.80 (m, 18H), 1.84-2.12 (m, 4H), 2.23-2.37 (m, 1H), 2.61-3.22 (m, 4H), 3.4-4.8 (m, 5H), 8.34-8.49 (m, 2H).

Example 16A

Ethyl 2-(4,4-difluoropiperidin-1-yl)pyrimidine-5-carboxylate

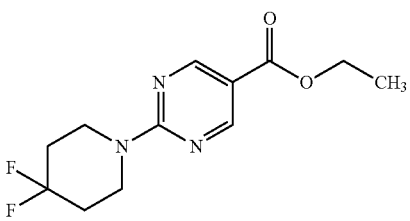 [SMILES: CCOC(=O)c1cnc(N2CCC(F)(F)CC2)nc1]

579 mg (4.78 mmol) of 4,4-difluoropiperidine were added to a suspension of 1.00 g (4.34 mmol) of ethyl 2-(methylsulphonyl)pyrimidine-5-carboxylate and 1.80 g (13.0 mmol) of potassium carbonate in 10 ml of acetonitrile. The mixture was stirred at RT for 18 h. The reaction mixture was then diluted with ethyl acetate and filtered off, the residue was washed with ethyl acetate/dichloromethane and the filtrate was concentrated. The crude product was purified on silica gel (elution: cyclohexane/ethyl acetate 8:1-5:1), which gave 500 mg (42% of theory) of the product.

LC-MS [Method 1]: $R_t$=1.08 min; MS (ESIpos): m/z=272 (M+H)$^+$ $^1$H-NMR (400 MHz, DMSO-d$_6$): δ [ppm]=1.29 (t, 3H), 1.97-2.11 (m, 4H), 3.96-4.03 (m, 4H), 4.28 (q, 2H), 8.82 (s, 2H).

Example 17A 2-(4,4-Difluoropiperidin-1-yl)pyrimidine-5-carboxylic acid

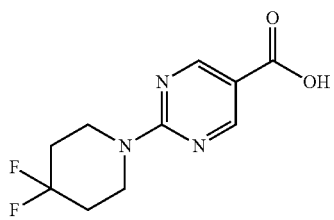 [SMILES: O=C(O)c1cnc(N2CCC(F)(F)CC2)nc1]

1.2 ml of a 3N solution of sodium hydroxide were added to a solution of 500 mg (1.84 mmol) of the compound from Example 16A in 5 ml of ethanol, and the mixture was stirred at RT for 18 h. For work-up, the reaction mixture was acidified with 6N HCl and the resulting precipitate was filtered off, washed with water and dried under HV. This gave 399 mg (89% of theory) of the title compound.

LC-MS [Method 1]: $R_t$=0.78 min; MS (ESIpos): m/z=244 (M+H)$^+$ $^1$H-NMR (400 MHz, DMSO-d$_6$): δ [ppm]=1.94-2.11 (m, 4H), 3.92-4.04 (m, 4H), 8.80 (s, 2H).

Example 18A

Ethyl 2-[(2R)-2-(methoxymethyl)pyrrolidin-1-yl]pyrimidine-5-carboxylate

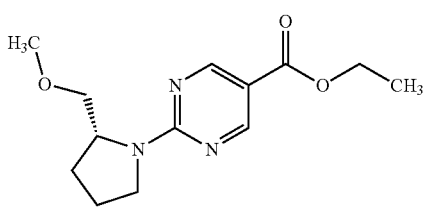 [SMILES: CCOC(=O)c1cnc(N2CCC[C@@H]2COC)nc1]

450 mg (3.91 mmol) of (R)-(+)-2-(methoxymethyl)pyrrolidine were added to a suspension of 818 mg (3.52 mmol) of ethyl 2-(methylsulphonyl)pyrimidine-5-carboxylate and 1.47 g (10.7 mmol) of potassium carbonate in 9.0 ml of acetonitrile. The mixture was stirred at RT for 18 h. The reaction mixture was then diluted with ethyl acetate and filtered off, the residue was washed with ethyl acetate/dichloromethane and the filtrate was concentrated. The crude product was purified on silica gel (elution: cyclohexane/ethyl acetate 8:1-5:1), which gave 558 mg (59% of theory) of the title compound.

LC-MS [Method 8]: $R_t$=2.75 min; MS (ESIpos): m/z=266 (M+H)$^+$ $^1$H-NMR (400 MHz, DMSO-d$_6$): δ [ppm]=1.29 (t, 3H), 1.86-2.09 (m, 4H), 3.26 (s, 3H), 3.36 (dd, 1H), 3.46-3.63 (m, 3H), 4.22-4.35 (m, 3H), 8.79 (s, 2H).

Example 19A

2-[(2R)-2-(Methoxymethyl)pyrrolidin-1-yl]pyrimidine-5-carboxylic acid

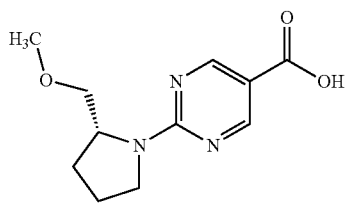 [SMILES: COC[C@H]1CCCN1c1ncc(C(=O)O)cn1]

1.4 ml of a 3N solution of sodium hydroxide were added to a solution of 540 mg (2.04 mmol) of the compound from Example 18A in 5 ml of ethanol, and the mixture was stirred at RT for 18 h. For work-up, the reaction mixture was concentrated, taken up in a little water and acidified with 6N hydrochloric acid, concentrated and dried under HV. The crude product obtained (797 mg, 60% pure) was directly reacted further.

LC-MS [Method 8]: $R_t$=1.55 min; MS (ESIpos): m/z=238 (M+H)$^+$

Example 20A (5-Fluoropyrazin-2-yl) [(3R)-3-methyl-1,4'-bipiperidin-1'-yl]methanone

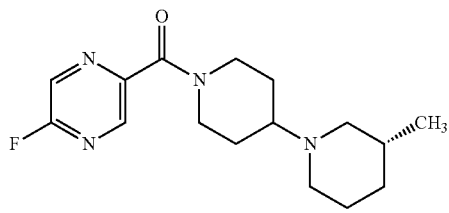 [SMILES: C[C@@H]1CCCN(C2CCN(C(=O)c3cnc(F)cn3)CC2)C1]

260 mg (1.83 mmol) of 5-fluoropyrazine-2-carboxylic acid and 560 mg of the compound from Example 2A (2.20 mmol) were dissolved in 2 ml of acetonitrile, and 1.1 ml (6.57 mmol) of N,N-diisopropylethylamine were added. 1.2 ml (2.21 mmol) of T3P (50% by weight strength solution in DMF) were then added, and the mixture was stirred at RT for 18 h. Subsequently, the mixture was concentrated, water were added and the mixture was extracted with about 50 ml of ethyl acetate. The organic phase was washed once with saturated aqueous sodium bicarbonate solution and once with saturated aqueous sodium chloride solution. The crude product was purified by preparative HPLC [Method 9], giving 156 mg of product (28% of theory).

LC-MS [Method 1]: $R_t$=0.35 min; MS (ESIpos): m/z=307 (M+H)$^+$

Working Examples

Example 1

[(3R)-3-Methyl-1,4'-bipiperidin-1'-yl][6-(morpholin-4-yl)pyridin-3-yl]methanone formic acid salt

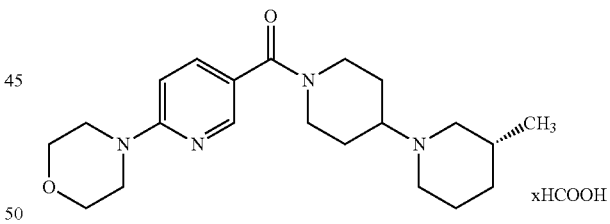

In a closed vessel, a mixture of 100 mg (0.28 mmol) of the compound from Example 8A, 73 μl (0.84 mmol) of morpholine, 0.24 ml (1.40 mmol) of N,N-diisopropylethylamine and 8.4 mg (0.056 mmol) of sodium iodide in 2.0 ml of DMSO was heated at 90° C. for 18 h. The reaction mixture was purified directly by preparative HPLC [Method 10], giving 93.0 mg (79% of theory) of the title compound.

Alternatively, a mixture of 100 mg (0.28 mmol) of the compound from Example 8A, 73 μl (0.84 mmol) of morpholine, 0.24 ml (1.40 mmol) of N,N-diisopropylethylamine and 6.8 mg (0.056 mmol) of DMAP in 2.0 ml of dioxane was heated in the microwave at 160° C. for 7 h. Purification of the reaction mixture by preparative HPLC [Method 9] gave 80 mg (68% of theory) of the title compound.

LC-MS [Method 8]: $R_t$=2.56 min; MS (ESIpos): m/z=373 (M+H)$^+$

¹H-NMR (400 MHz, DMSO-d₆): δ [ppm]=0.78-0.92 (m, 4H), 1.35-1.69 (m, 6H), 1.71-1.82 (m, 2H), 1.83-1.92 (m, 1H), 2.12-2.22 (m, 1H), 2.58-2.68 (m, 1H), 2.73-3.04 (m, 4H), 3.46-3.54 (m, 4H), 3.64-3.72 (m, 4H), 3.73-4.75 (m, 2H), 6.84 (d, 1H), 7.60 (dd, 1H), 8.19 (s, 2H).

Example 2

[(3R)-3-Methyl-1,4'-bipiperidin-1'-yl][6-(morpholin-4-yl)pyridin-3-yl]methanone

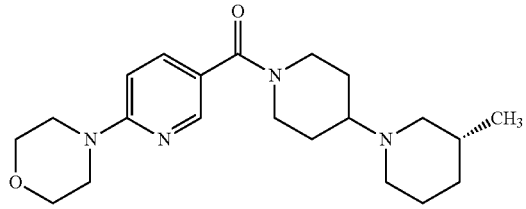 [SMILES: C[C@@H]1CCCN(C2CCN(C(=O)c3ccc(N4CCOCC4)nc3)CC2)C1]

4.2 ml (24 mmol) of N,N-diisopropylethylamine was added to a mixture of 1.00 g (4.80 mmol) of the compound from Example 7A and 1.47 g (5.76 mmol) of the compound from Example 2A in 50 ml of acetonitrile. 3.4 ml (5.8 mmol) of T3P (50% by weight strength solution in ethyl acetate) were then added dropwise, and the mixture was stirred at RT for 18 h. For work-up, 50 ml of saturated sodium bicarbonate solution were added, the mixture was stirred for 30 min and the organic phase was concentrated substantially. The mixture was then extracted twice with ethyl acetate, and the combined organic phases were washed twice with saturated sodium bicarbonate solution and saturated sodium chloride solution, dried over magnesium sulphate, filtered and concentrated. The crude product was purified by preparative HPLC [Method 11], giving 1.15 g (64% of theory) of the title compound.

LC-MS [Method 8]: R$_t$=2.50 min; MS (ESIpos): m/z=373 (M+H)⁺

¹H-NMR (400 MHz, DMSO-d₆): δ [ppm]=0.73-0.89 (m, 4H), 1.31-1.81 (m, 9H), 1.99-2.11 (m, 1H), 2.40-2.50 (m, 1H), 2.65-3.10 (m, 4H), 3.47-3.54 (m, 4H), 3.64-3.72 (m, 4H), 3.77-4.55 (m, 2H), 6.83 (d, 1H), 7.60 (dd, 1H), 8.19 (d, 1H).

Example 3

{6-[(2R)-2-(Methoxymethyl)pyrrolidin-1-yl]pyridin-3-yl}[(3R)-3-methyl-1,4'-bipiperidin-1'-yl]methanone formic acid salt

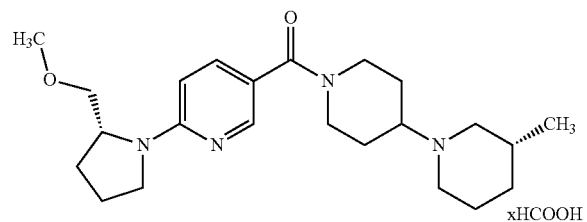

In a microwave, a mixture of 100 mg (0.28 mmol) of the compound from Example 8A, 96 mg (0.84 mmol) of (2R)-2-(methoxymethyl)pyrrolidine, 0.24 ml (1.40 mmol) of N,N-diisopropylethylamine and 42 mg (0.28 mmol) of caesium fluoride in 0.5 ml of N-methyl-2-pyrrolidone was heated at 220° C. for 1.5 h. After cooling to RT, water was added, the mixture was extracted three times with ethyl acetate and the combined organic phases were washed with saturated sodium chloride solution, dried over sodium sulphate, filtered and concentrated. The residue obtained was purified by preparative HPLC [Method 10], giving 20 mg (15% of theory) of the title compound.

LC-MS [Method 1]: R$_t$=0.42 min; MS (ESIpos): m/z=401 (M+H)⁺

¹H-NMR (400 MHz, DMSO-d₆): δ [ppm]=0.76-0.90 (m, 4H), 1.32-2.16 (m, 15H), 2.72-3.04 (m, 4H), 3.26 (s, 3H), 3.42-3.52 (m, 2H), 3.85-4.38 (m, 2H), 6.50 (d, 1H), 7.54 (dd, 1H), 8.16 (d, 1H), 8.22 (br. s, 1H, formic acid).

Example 4

{6-[(2-Methoxyethyl)amino]pyridin-3-yl}[(3R)-3-methyl-1,4'-bipiperidin-1'-yl]methanone

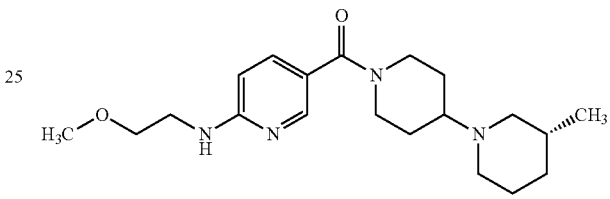

2.5 ml (14 mmol) of N,N-diisopropylethylamine were added to a mixture of 567 mg (2.89 mmol) of the compound from Example 6A and 811 mg (3.18 mmol) of the compound from Example 2A in 6.0 ml of acetonitrile. 2.1 ml (3.5 mmol) of T3P (50% by weight strength solution in ethyl acetate) were then added dropwise, and the mixture was stirred at RT for 18 h. For work-up, 15 ml of saturated sodium bicarbonate solution were added, the mixture was stirred for 15 min and the organic phase was concentrated substantially and then extracted three times with dichloromethane. The combined organic phases were dried over magnesium sulphate, filtered and concentrated. The crude product was purified by preparative HPLC [Method 12], giving 847 mg (80% of theory) of the title compound.

LC-MS [Method 8]: R$_t$=2.23 min; MS (ESIpos): m/z=361 (M+H)⁺

¹H-NMR (400 MHz, DMSO-d₆): δ [ppm]=0.74-0.86 (m, 4H), 1.28-1.81 (m, 9H), 1.99-2.10 (m, 1H), 2.69-2.98 (m, 4H), 3.27 (s, 3H), 3.40-3.49 (m, 4H), 3.79-4.36 (m, 2H), 6.50 (d, 1H), 6.98-7.05 (m, 1H), 7.41 (dd, 1H), 8.04 (d, 1H).

Example 5

[6-(4,4-Difluoropiperidin-1-yl)pyridin-3-yl][(3R)-3-methyl-1,4'-bipiperidin-1'-yl]methanone

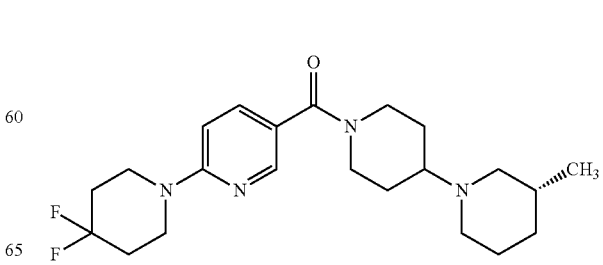

In a microwave, a mixture of 100 mg (0.279 mmol) of the compound from Example 8A, 132 mg (0.837 mmol) of 4,4-difluoropiperidine hydrochloride, 0.24 ml (1.4 mmol) of N,N-diisopropylethylamine and 6.8 mg (0.056 mmol) of DMAP in 1.0 ml of methanol was heated at 140° C. for 6 h. The crude product was purified by preparative HPLC [Method 9], giving 60 mg (53% of theory) of the title compound.

LC-MS [Method 8]: $R_t$=2.72 min; MS (ESIpos): m/z=407 (M+H)$^+$ $^1$H-NMR (400 MHz, DMSO-d$_6$): δ [ppm]=0.75-0.88 (m, 4H), 1.30-1.80 (m, 9H), 1.92-2.10 (m, 5H), 2.71-3.08 (m, 4H), 3.69-3.77 (m, 4H), 3.78-4.63 (m, 2H), 6.96 (d, 1H), 7.60 (dd, 1H), 8.19 (d, 1H).

Example 6

{6-[(2-Methoxyethyl)(methyl)amino]pyridin-3-yl}[(3R)-3-methyl-1,4'-bipiperidin-1'-yl]methanone hydrochloride

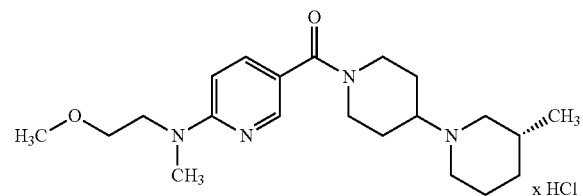

In a microwave, a mixture of 100 mg (0.28 mmol) of the compound from Example 8A, 124 mg (1.40 mmol) of methoxyethylmethylamine, 0.24 ml (1.4 mmol) of N,N-diisopropylethylamine and 42 mg (0.28 mmol) of caesium fluoride in 0.5 ml of N-methyl-2-pyrrolidone was heated at 240° C. for 30 min After cooling to RT, water was added and the mixture was extracted three times with ethyl acetate. The combined organic phases were dried over magnesium sulphate, filtered and concentrated. The residue was purified by preparative HPLC [Method 9], giving 58 mg (55% of theory) of the title compound as the free base. The product was dissolved in dichloromethane and, using 0.5 ml of 4M hydrogen chloride in dioxane, converted into the corresponding hydrochloride, giving 61 mg (53% of theory).

Free Base:

LC-MS [Method 8]: $R_t$=2.37 min; MS (ESIpos): m/z=375 (M+H)$^+$ $^1$H-NMR (400 MHz, DMSO-d$_6$): δ [ppm]=0.74-0.88 (m, 4H), 1.29-1.81 (m, 9H), 1.97-2.10 (m, 1H), 2.70-2.98 (m, 4H), 3.05 (s, 3H), 3.25 (s, 3H), 3.46-3.52 (m, 2H), 3.69-3.74 (m, 2H), 3.80-4.42 (m, 2H), 6.62 (d, 1H), 7.54 (dd, 1H), 8.14 (d, 1H).

HCl Salt:

LC-MS [Method 1]: $R_t$=0.39 min; MS (ESIpos): m/z=375 (M+H)$^+$ $^1$H-NMR (400 MHz, DMSO-d$_6$): δ [ppm]=0.90 (d, 3H), 1.01-1.16 (m, 1H), 1.57-2.22 (m, 9H), 2.74-3.10 (m, 4H), 3.19 (s, 3H), 3.26 (s, 3H), 6.96-7.13 (m, 1H), 7.74-7.88 (m, 1H), 8.11 (s, 1H), 10.56-10.77 (m, 1H).

Example 7

[3-(Cyclopropylmethoxy)-1,4'-bipiperidin-1'-yl][6-(morpholin-4-yl)pyridin-3-yl]methanone

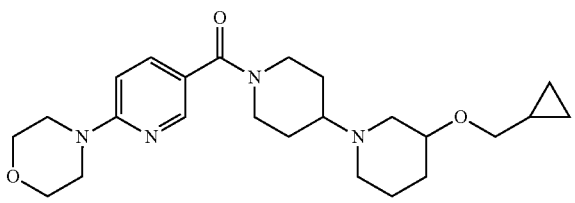

0.39 ml (2.22 mmol) of N,N-diisopropylethylamine was added to a mixture of 100 mg (0.32 mmol) of the compound from Example 7A and 118 mg (0.38 mmol) of the compound from Example 5A in 2.0 ml of acetonitrile. 0.22 ml (0.38 mmol) of T3P (50% by weight strength solution in ethyl acetate) were then added dropwise, and the mixture was stirred at RT for 18 h. For work-up, 2.0 ml of saturated sodium bicarbonate solution were added, the mixture was stirred for 15 min and then filtered through an Extrelut cartridge and eluted with ethyl acetate. The filtrate was concentrated and purified by preparative HPLC [Method 9], giving 86.8 mg (61% of theory) of the title compound.

LC-MS [Method 8]: $R_t$=2.38 min; MS (ESIpos): m/z=429 (M+H)$^+$ $^1$H-NMR (400 MHz, DMSO-d$_6$): δ [ppm]=0.09-0.17 (m, 2H), 0.39-0.46 (m, 2H), 0.86-1.12 (m, 2H), 1.26-1.49 (m, 3H), 1.56-1.78 (m, 3H), 1.84-1.98 (m, 2H), 2.02-2.15 (m, 1H), 2.60-3.09 (m, 5H), 3.21-3.28 (m, 3H), 3.47-3.56 (m, 4H), 3.65-3.73 (m, 4H), 3.73-4.61 (m, 2H), 6.84 (d, 1H), 7.60 (dd, 1H), 8.19 (d, 1H).

Example 8

{6-[(2,6-Difluorobenzyl)(methyl)amino]pyridin-3-yl}[(3R)-3-methyl-1,4'-bipiperidin-1'-yl]methanone

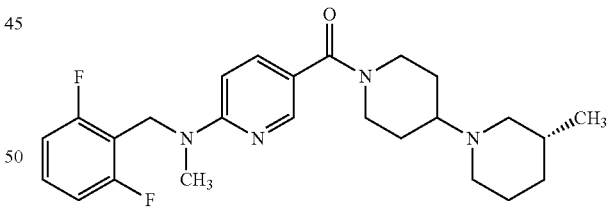

In a microwave, a mixture of 100 mg (0.28 mmol) of the compound from Example 8A and 132 mg (0.84 mmol) of 1-(2,6-difluorophenyl)-N-methylmethanamine was heated at 140° C. for 10 min and then at 180° C. for 30 min After cooling to RT, the reaction mixture was diluted with water and acetonitrile and purified by preparative HPLC [Method 9], giving 75.3 mg (60% of theory) of the title compound.

LC-MS [Method 8]: $R_t$=3.27 min; MS (ESIpos): m/z=443 (M+H)$^+$ $^1$H-NMR (400 MHz, DMSO-d$_6$): δ [ppm]=0.75-0.87 (m, 4H), 1.31-1.79 (m, 9H), 2.00-2.10 (m, 1H), 2.69-2.95 (m, 3H), 2.97 (s, 3H), 3.63-4.36 (m, 2H), 4.89 (s, 2H), 6.72 (d, 1H), 7.06-7.15 (m, 2H), 7.35-7.45 (m, 1H), 7.58 (dd, 1H), 8.15-8.18 (m, 1H).

Example 9

[6-(1,1-Dioxidothiomorpholin-4-yl)pyridin-3-yl][(3R)-3-methyl-1,4'-bipiperidin-1'-yl]methanone

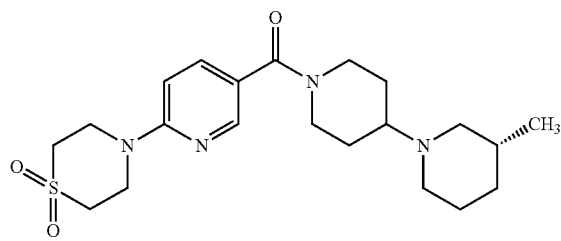 [SMILES: C[C@@H]1CCCN(C2CCN(C(=O)c3ccc(N4CCS(=O)(=O)CC4)nc3)CC2)C1]

In a microwave, a mixture of 100 mg (0.29 mmol) of the compound from Example 9A, 79 mg (0.59 mmol) of thiomorpholine 1,1-dioxide and 0.26 ml (1.46 mmol) of N,N-diisopropylethylamine in 1.0 ml of N-methyl-2-pyrrolidone was heated at 220° C. for 2.5 h. After cooling to RT, the reaction mixture was diluted with water and extracted twice with ethyl acetate. The combined organic phases were washed with saturated sodium chloride solution, dried over magnesium sulphate and concentrated and the residue was purified by preparative HPLC [Method 9], giving 30 mg (22% of theory) of the title compound.

LC-MS [Method 2]: $R_t$=0.44 min; MS (ESIpos): m/z=421 (M+H)$^+$ $^1$H-NMR (500 MHz, DMSO-d$_6$): δ [ppm]=0.76-0.87 (m, 4H), 1.33-1.81 (m, 9H), 2.01-2.11 (m, 1H), 2.68-3.05 (m, 4H), 3.09-3.16 (m, 4H), 4.06-4.13 (m, 4H), 3.5-4.5 (m, 2H), 7.02 (d, 1H), 7.64 (dd, 1H), 8.21 (d, 1H).

Example 10

(6-{[(2 S)-1-Hydroxybutan-2-yl]amino}pyridin-3-yl)[(3R)-3-methyl-1,4'-bipiperidin-1'-yl]methanone

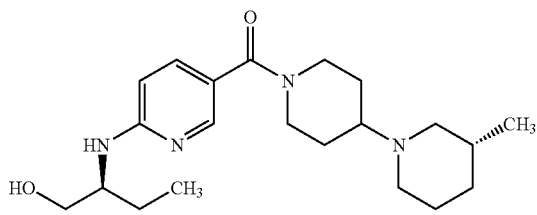 [SMILES: CC[C@@H](CO)Nc1ccc(C(=O)N2CCC(N3CCC[C@@H](C)C3)CC2)cn1]

In a microwave, a mixture of 100 mg (3.27 mmol) of the compound from Example 9A, 58 mg (0.66 mmol) of (S)-(+)-2-amino-1-butanol and 0.29 ml (1.64 mmol) of N,N-diisopropylethylamine in 1.1 ml of 2-propanol was heated at 180° C. for 1 h and then at 200° C. for 3 h. After cooling to RT, the reaction mixture was concentrated, diluted with water and acetonitrile and purified by preparative HPLC [Method 9], giving 105 mg (78% of theory) of the title compound.

LC-MS [Method 8]: $R_t$=2.35 min; MS (ESIpos): m/z=375 (M+H)$^+$ $^1$H-NMR (400 MHz, DMSO-d$_6$): δ [ppm]=0.74-0.84 (m, 4H), 0.88 (t, 3H), 1.29-1.83 (m, 11H), 2.00-2.13 (m, 1H), 2.70-3.01 (m, 4H), 3.41-3.50 (m, 1H), 3.75-3.88 (m, 1H), 3.91-4.37 (m, 2H), 4.60-4.66 (m, 1H), 6.49 (d, 1H), 6.66 (d, 1H), 7.38 (dd, 1H), 8.02 (d, 1H).

Example 11

{6[(1-Hydroxybutan-2-yl)amino]pyridin-3-yl}[(3R)-3-methyl-1,4'-bipiperidin-1'-yl]methanone

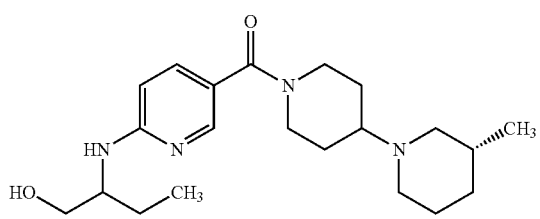 [SMILES: CCC(CO)Nc1ccc(C(=O)N2CCC(N3CCC[C@@H](C)C3)CC2)cn1]

In a microwave, a mixture of 500 mg (1.64 mmol) of the compound from Example 9A, 0.31 ml (0.33 mmol) of 2-amino-1-butanol and 1.4 ml (8.2 mmol) of N,N-diisopropylethylamine in 3.0 ml of N-methyl-2-pyrrolidone was heated at 180° C. for 30 min. 0.31 ml (0.38 mmol) of DL-2-amino-1-butanol was then added, and the mixture was heated at 180° C. for a further 15 min. After cooling to room temperature, 100 ml of water were added and the mixture was extracted three times with 50 ml of ethyl acetate. The combined organic phases were washed with saturated sodium chloride solution, dried over magnesium sulphate and concentrated. The residue was purified by preparative HPLC [Method 14], giving 400 mg (65% of theory) of the title compound.

LC-MS [Method 8]: $R_t$=2.18 min; MS (ESIpos): m/z=375 (M+H)$^+$ $^1$H-NMR (400 MHz, DMSO-d$_6$): δ [ppm]=0.74-0.84 (m, 4H), 0.88 (t, 3H), 1.30-1.81 (m, 11H), 2.00-2.10 (m, 1H), 2.42-2.50 (m, 1H), 2.69-2.97 (m, 4H), 3.42-3.51 (m, 1H), 3.76-3.90 (m, 1H), 3.91-4.33 (m, 2H), 4.60-4.68 (m, 1H), 6.49 (d, 1H), 6.66 (d, 1H), 7.38 (dd, 1H), 8.02 (d, 1H).

Example 12

2-[(5-{[(3R)-3-Methyl-1,4'-bipiperidin-1'-yl]carbonyl}pyridin-2-yl)amino]butyl carbamate

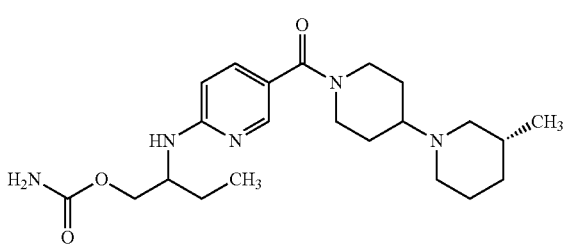 [SMILES: CCC(COC(N)=O)Nc1ccc(C(=O)N2CCC(N3CCC[C@@H](C)C3)CC2)cn1]

24.4 μl (0.280 mmol) of chlorosulphonyl isocyanate were added dropwise to a solution, pre-cooled to −15° C., of 75.0 mg (0.200 mmol) of the compound from Example 11 in acetonitrile, and the mixture was stirred at this temperature for 1 h. 6 ml of water were then added and the mixture was stirred at 60° C. for 18 h. After cooling to RT, the reaction mixture was concentrated to half its original volume and purified by preparative HPLC [Method 13], giving 27 mg (32% of theory) of the title compound.

LC-MS [Method 8]: R$_t$=2.20 min; MS (ESIpos): m/z=418 (M+H)$^+$ $^1$H-NMR (400 MHz, DMSO-d$_6$): δ [ppm]=0.75-0.85 (m, 4H), 0.89 (t, 3H), 1.26-1.84 (m, 11H), 1.91-2.16 (m, 1H), 2.69-3.02 (m, 4H), 3.89-3.94 (m, 2H), 3.94-4.25 (m, 3H), 6.34-6.64 (m, 3H), 6.81-6.86 (m, 1H), 7.41 (dd, 1H), 8.04 (d, 1H).

Example 13

[6-(3-Methoxypyrrolidin-1-yl)pyridin-3-yl][(3R)-3-methyl-1,4'-bipiperidin-1'-yl]methanone

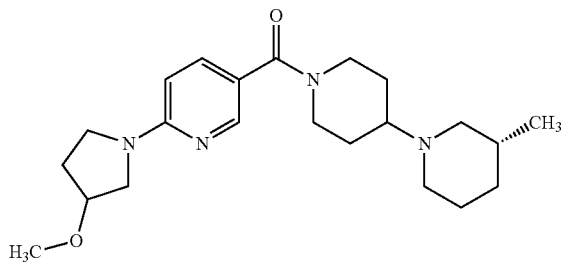

In a microwave, a mixture of 100 mg (0.38 mmol) of the compound from Example 9A, 90 mg (0.66 mmol) of 3-methoxypyrrolidine hydrochloride and 0.29 ml (1.64 mmol) of N,N-diisopropylethylamine in 1.0 ml of N-methyl-2-pyrrolidone was heated at 180° C. for 30 min After cooling to room temperature, the reaction mixture was diluted with water and extracted twice with ethyl acetate. The combined organic phases were washed with saturated sodium chloride solution, dried over magnesium sulphate, filtered and concentrated. The residue was purified by preparative HPLC [Method 13], giving 70.0 mg (54% of theory) of the title compound.

LC-MS [Method 8]: R$_t$=2.34 min; MS (ESIpos): m/z=387 (M+H)$^+$ $^1$H-NMR (400 MHz, DMSO-d$_6$): δ [ppm]=0.73-0.90 (m, 4H), 1.29-1.86 (m, 9H), 1.97-2.13 (m, 3H), 2.70-3.02 (m, 4H), 3.26 (s, 3H), 3.36-3.42 (m, 1H), 3.46-3.57 (m, 3H), 3.72-4.46 (m, 2H), 6.45 (d, 1H), 7.54 (dd, 1H), 8.15 (d, 1H).

Example 14

{6-[(1-Methoxybutan-2-yl)amino]pyridin-3-yl}[(3R)-3-methyl-1,4'-bipiperidin-1'-yl]methanone

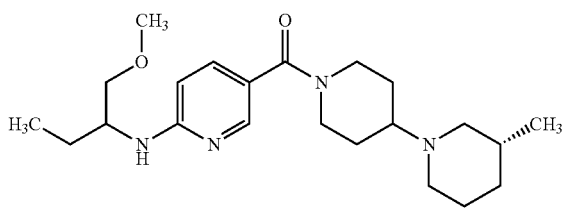 [SMILES: CCC(COC)Nc1ccc(C(=O)N2CCC(N3CCC[C@@H](C)C3)CC2)cn1]

A mixture of 100 mg (0.27 mmol) of the compound from Example 10A, 85 mg (0.82 mmol) of 1-methoxy-2-butylamine, 131 mg (1.37 mmol) of sodium tert-butoxide, 4.4 mg (0.008 mmol) of 2-(dicyclohexylphosphino)-3,6-dimethoxy-2,4,6-triisopropyl-1,1-biphenyl and 5.0 mg (0.005 mmol) of tris(dibenzylideneacetone)dipalladium(0) in 3.0 ml of toluene was stirred at RT for 1 h and then at 90° C. for 18 h. For work-up, the mixture was filtered through kieselguhr, eluting with ethyl acetate, and the filtrate was concentrated. The residue was purified by preparative HPLC [Method 9], giving 18 mg (16% of theory) of the title compound.

LC-MS [Method 8]: R$_t$=2.90 min; MS (ESIpos): m/z=389 (M+H)$^+$ $^1$H-NMR (400 MHz, DMSO-d$_6$): δ [ppm]=0.75-0.91 (m, 7H), 1.29-1.80 (m, 11H), 1.94-2.13 (m, 1H), 2.70-2.93 (m, 3H), 3.25 (s, 3H), 3.89-4.24 (m, 3H), 6.47-6.52 (m, 1H), 6.72-6.80 (m, 1H), 7.37-7.41 (m, 1H), 8.02-8.04 (m, 1H).

Example 15

[(3R)-3-Methyl-1,4'-bipiperidin-1'-yl][6-(3-methylpiperidin-1-yl)pyridin-3-yl]methanone

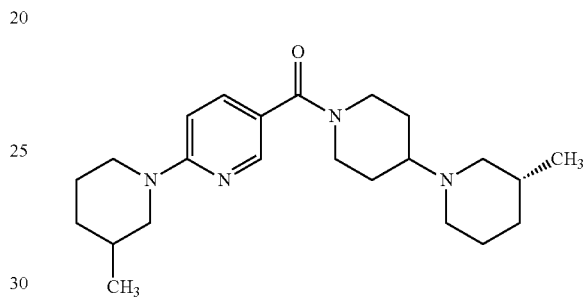

0.37 ml (2.15 mmol) of N,N-diisopropylethylamine was added to a mixture of 945 mg (0.43 mmol) of 6-(3-methylpiperidin-1-yl)nicotinic acid and 110 mg (0.43 mmol) of the compound from Example 2A in 1.9 ml of acetonitrile. 0.30 ml (0.52 mmol) of T3P (50% by weight strength solution in ethyl acetate) was then added dropwise, and the mixture was stirred at RT for 18 h. For work-up, 1.5 ml of saturated sodium bicarbonate solution were added, the mixture was stirred for 20 min and then filtered through an Extrelut cartridge, washing with ethyl acetate. The filtrate was concentrated and the residue was purified by preparative HPLC [Method 9], giving 101 mg (60% of theory) of the title compound.

LC-MS [Method 8]: R$_t$=2.84 min; MS (ESIpos): m/z=385 (M+H)$^+$ $^1$H-NMR (400 MHz, DMSO-d$_6$): δ [ppm]=0.74-0.86 (m, 4H), 0.90 (d, 3H), 1.09-1.21 (m, 1H), 1.30-1.82 (m, 13H), 1.99-2.11 (m, 1H), 2.68-3.05 (m, 5H), 3.5-4.5 (m, 2H), 4.22-4.30 (m, 2H), 6.81 (d, 1H), 7.52 (dd, 1H), 8.14 (d, 1H).

Example 16

[(3R)-3-Methyl-1,4'-bipiperidin-1'-yl][2-(morpholin-4-yl)pyrimidin-5-yl]methanone

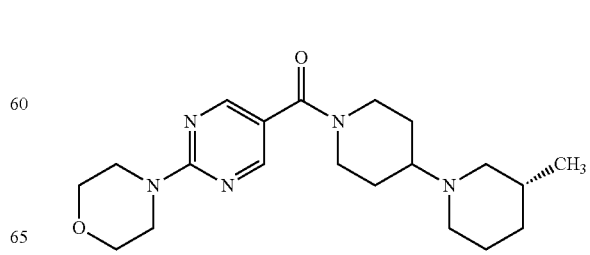

4.37 ml (25.1 mmol) of N,N-diisopropylethylamine were added to a mixture of 0.750 g (3.59 mmol) of 2-(morpholin-4-yl)pyrimidine-5-carboxylic acid and 1.01 g (3.94 mmol) of the compound from Example 2A in 15 ml of acetonitrile. 2.51 ml (4.30 mmol) of T3P (50% by weight strength solution in ethyl acetate) were then added dropwise, and the mixture was stirred at RT for 18 h. For work-up, 50 ml of saturated sodium bicarbonate solution were added and the mixture was stirred for 20 min and then extracted three times with ethyl acetate. The combined organic phases were washed with saturated sodium bicarbonate solution and saturated sodium chloride solution, dried over magnesium sulphate, filtered and concentrated. The residue was purified by preparative HPLC [Method 9], giving 790 mg (59% of theory) of the title compound.

LC-MS [Method 8]: $R_t$=2.28 min; MS (ESIpos): m/z=374 $(M+H)^+$ $^1$H-NMR (400 MHz, DMSO-d$_6$): δ [ppm]=0.75-0.89 (m, 4H), 1.31-1.80 (m, 9H), 1.99-2.10 (m, 1H), 2.70-3.12 (m, 4H), 3.62-3.69 (m, 4H), 3.74-3.79 (m, 4H), 3.80-4.60 (m, 2H), 8.45 (s, 2H).

Example 17

[3-(Cyclopropylmethoxy)-1,4'-bipiperidin-1'-yl][2-(morpholin-4-yl)pyrimidin-5-yl]methanone

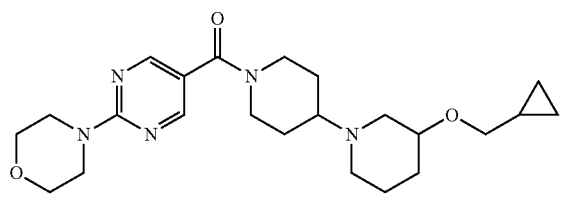 [SMILES: O=C(c1cnc(N2CCOCC2)nc1)N1CCC(N2CCCC(OCC3CC3)C2)CC1]

0.42 ml (2.39 mmol) of N,N-diisopropylethylamine was added to a mixture of 100 mg (0.48 mmol) of 2-(morpholin-4-yl)pyrimidine-5-carboxylic acid and 149 mg (0.48 mmol) of the compound from Example 5A in 2.0 ml of acetonitrile. 0.34 ml (0.57 mmol) of T3P (50% by weight strength solution in ethyl acetate) was then added dropwise, and the mixture was stirred at RT for 18 h. For work-up, 1.5 ml of saturated sodium bicarbonate solution were added, the mixture was stirred for 20 min and then filtered through an Extrelut cartridge, washing with ethyl acetate. The filtrate was concentrated and the residue was purified by preparative HPLC [Method 9], giving 128 mg (61% of theory) of the title compound.

LC-MS [Method 8]: $R_t$=2.36 min; MS (ESIpos): m/z=430 $(M+H)^+$ $^1$H-NMR (400 MHz, DMSO-d$_6$): δ [ppm]=0.05-0.19 (m, 2H), 0.37-0.48 (m, 2H), 0.86-1.12 (m, 2H), 1.25-1.50 (m, 3H), 1.55-1.81 (m, 3H), 1.82-1.99 (m, 2H), 2.03-2.15 (m, 1H), 2.61-3.16 (m, 4H), 3.20-3.30 (m, 3H), 3.62-3.71 (m, 4H), 3.71-3.80 (m, 4H), 3.5-5.0 (m, 2H), 8.46 (s, 2H).

Example 18

[(3R)-3-Methyl-1,4'-bipiperidin-1'-yl][2-(2-oxa-6-azaspiro[3.3]hept-6-yl)pyrimidin-5-yl]methanone

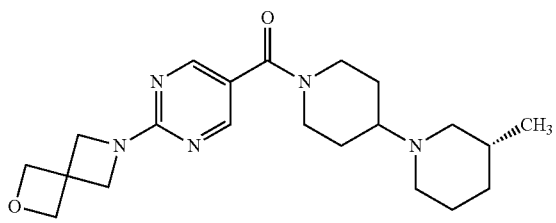 [SMILES: C[C@@H]1CCCN(C2CCN(C(=O)c3cnc(N4CC5(COC5)C4)nc3)CC2)C1]

0.28 ml (1.59 mmol) of N,N-diisopropylethylamine was added to a mixture of 58 mg (0.23 mmol) of the compound from Example 12A and 58 mg (0.23 mmol) of the compound from Example 2A in 1.9 ml of acetonitrile. 0.16 ml (0.27 mmol) of T3P (50% by weight strength solution in ethyl acetate) were then added dropwise, and the mixture was stirred at RT for 18 h. For work-up, 1.0 ml of saturated sodium bicarbonate solution were added, the mixture was stirred for 15 min and then filtered through an Extrelut cartridge, eluting with dichloromethane. The filtrate was concentrated and the residue was purified by preparative HPLC [Method 9], giving 20 mg (23% of theory) of the title compound.

LC-MS [Method 8]: $R_t$=2.05 min; MS (ESIpos): m/z=386 $(M+H)^+$ $^1$H-NMR (400 MHz, DMSO-d$_6$): δ [ppm]=0.74-0.88 (m, 4H), 1.32-1.80 (m, 9H), 1.98-2.11 (m, 1H), 2.68-3.10 (m, 4H), 4.25 (s, 4H), 4.72 (s, 4H), 8.40 (s, 2H).

Example 19

[2-(4,4-Difluoropiperidin-1-yl)pyrimidin-5-yl][(3R)-3-methyl-1,4'-bipiperidin-1'-yl]methanone

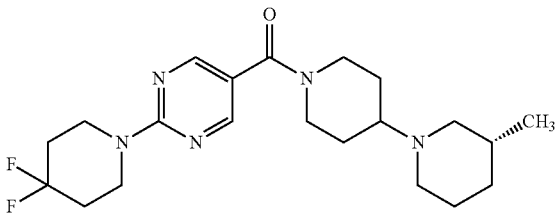 [SMILES: C[C@@H]1CCCN(C2CCN(C(=O)c3cnc(N4CCC(F)(F)CC4)nc3)CC2)C1]

0.50 ml (2.88 mmol) of N,N-diisopropylethylamine was added to a mixture of 100 mg (0.41 mmol) of the compound from Example 17A and 105 mg (0.41 mmol) of the compound from Example 2A in 4.0 ml of acetonitrile. 0.29 ml (0.49 mmol) of T3P (50% by weight strength solution in ethyl acetate) were then added dropwise, and the mixture was stirred at RT for 18 h. For work-up, 1.0 ml of saturated sodium bicarbonate solution were added, the mixture was stirred for 15 min and then filtered through an Extrelut cartridge, eluting with ethyl acetate. The filtrate was concentrated and the residue was purified by preparative HPLC [Method 9], giving 113 mg (67% of theory) of the title compound.

LC-MS [Method 8]: $R_t$=2.82 min; MS (ESIpos): m/z=408 $(M+H)^+$ $^1$H-NMR (400 MHz, DMSO-d$_6$): δ [ppm]=0.74-0.89 (m, 4H), 1.32-1.79 (m, 9H), 1.94-2.11 (m, 5H), 2.69-3.18 (m, 4H), 3.48-4.85 (m, 6H), 8.47 (s, 2H).

Example 20

{2-[(2R)-2-(Methoxymethyl)pyrrolidin-1-yl]pyrimidin-5-yl}[(3R)-3-methyl-1,4'-bipiperidin-1'-yl]methanone

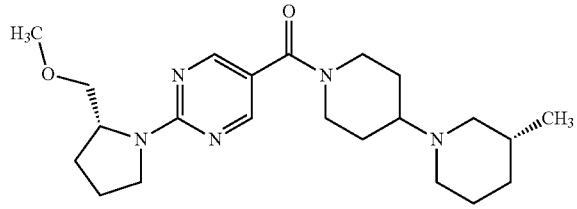

0.46 ml (2.66 mmol) of N,N-diisopropylethylamine was added to a mixture of 150 mg (0.38 mmol) of the compound from Example 19A and 97 mg (0.38 mmol) of the compound from Example 2A in 4.0 ml of acetonitrile. 0.27 ml (0.46 mmol) of T3P (50% by weight strength solution in ethyl acetate) were then added dropwise, and the mixture was stirred at RT for 18 h. For work-up, 1 ml of saturated sodium bicarbonate solution were added, the mixture was stirred for 15 min and then filtered through an Extrelut cartridge, eluting with ethyl acetate. The filtrate was concentrated and the residue was purified by preparative HPLC [Method 9], giving 95.0 mg (62% of theory) of the title compound.

LC-MS [Method 8]: R$_t$=2.59 min; MS (ESIpos): m/z=402 (M+H)$^+$ $^1$H-NMR (400 MHz, DMSO-d$_6$): δ [ppm]=0.71-0.96 (m, 4H), 1.27-1.82 (m, 9H), 1.86-2.15 (m, 5H), 2.69-3.12 (m, 4H), 3.26 (s, 3H), 3.40-3.58 (m, 3H), 3.59-4.59 (m, 3H), 8.43 (s, 2H).

Example 21

[5-(1,1-Dioxidothiomorpholin-4-yl)pyrazin-2-yl][(3R)-3-methyl-1,4'-bipiperidin-1'-yl]methanone

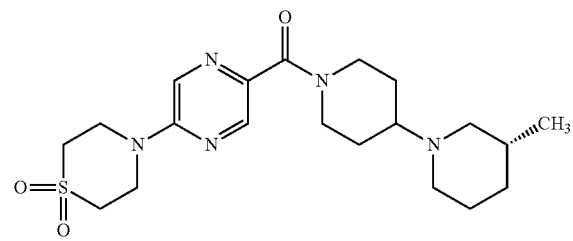 [SMILES: C[C@@H]1CCCN(C2CCN(C(=O)c3cnc(N4CCS(=O)(=O)CC4)cn3)CC2)C1]

0.14 ml of N-methyl-2-pyrrolidone was added to 50 mg (0.16 mmol) of the compound from Example 20A and 66 mg of thiomorpholine 1,1-dioxide (0.49 mmol), and the mixture was stirred in the microwave at 180° C. for 45 min. The reaction was then purified by preparative HPLC [Method 9], giving 36 mg (53% of theory) of the title compound.

LC-MS [Method 1]: R$_t$=0.45 min; MS (ESIpos): m/z=422 (M+H)$^+$ $^1$H-NMR (400 MHz, DMSO-d$_6$): δ [ppm]=0.82 (d, 4H), 1.29-1.47 (m, 3H), 1.47-1.71 (m, 4H), 1.71-1.82 (m, 2H), 1.98-2.13 (m, 1H), 2.68-2.79 (m, 3H), 2.96-3.12 (m, 1H), 3.20 (br. s., 5H), 4.00-4.10 (m, 1H), 4.11-4.21 (m, 4H), 4.41-4.56 (m, 1H), 8.34-8.39 (m, 1H), 8.40-8.46 (m, 1H).

B) ASSESSMENT OF PHYSIOLOGICAL EFFICACY

The suitability of the compounds according to the invention for treating cardiovascular disorders can be demonstrated in the following assay systems:

B-1) In Vitro Assays

B-1a) Antagonism Against Adrenoreceptors

Antagonism against the adrenoreceptor $α_{1A}$ was tested using a recombinant human $α_{1A}$ receptor CHO cell line which additionally also recombinantly expresses mtAeq (mitochondrial aequorin). Antagonism against the adrenoreceptor $α_{2A}$ was tested using a recombinant human $α_{2A}$-Gα16 receptor fusion protein CHO cell line (PerkinElmer Life Sciences) which additionally also recombinantly expresses mtAeq. Antagonism against the adrenoreceptor $α_{2B}$ was tested using a recombinant human $α_{2B}$ receptor CHO cell line (PerkinElmer Life Sciences) which additionally also recombinantly expresses mtAeq. Antagonism against the adrenoreceptor $α_{2C}$ was tested using a recombinant human $α_{2C}$ receptor CHO cell line which additionally also recombinantly expresses a chimeric G protein (Gαqi3) and mtOb (mitochondrial obelin).

The cells were cultivated at 37° C. and 5% CO$_2$ in Dulbecco's modified Eagle's Medium/NUT mix F12 with L-glutamine which additionally contained 10% (v/v) inactivated foetal calf serum, 1 mM sodium pyruvate, 0.9 mM sodium bicarbonate, 50 U/ml penicillin, 50 μg/ml streptomycin, 2.5 μg/ml amphotericin B and 1 mg/ml Geneticin. The cells were passaged with enzyme-free Hank's-based cell dissociation buffer. All cell culture reagents used were from Invitrogen (Carlsbad, USA).

Luminescence measurements were carried out on white 384-well microtitre plates. 2000 cells/well were plated in a volume of 25 μl and cultivated for one day at 30° C. and 5% CO$_2$ in cell culture medium with coelenterazine ($α_{2A}$ and $α_{2B}$: 5 μg/ml; $α_{1a/c}$ and $α_{2C}$: 2.5 μg/ml). Serial dilutions of the test substances (10 μl) were added to the cells. After 5 minutes, noradrenaline was added to the cells (35 μl; final concentrations: 20 nM ($α_{1a/c}$ and $α_{2C}$) or 200 nM ($α_{2A}$ and $α_{2B}$)), and the emitted light was measured for 50 seconds using a CCD (charge-coupled device) camera (Hamamatsu Corporation, Shizuoka, Japan) in a light-tight box. The test substances were tested up to a maximum concentration of 10 μM. The IC$_{50}$ values were calculated from the appropriate dose-response curves. The results for the antagonism against the adrenoreceptor $α_{2C}$ are shown in Table 1:

TABLE 1

| Example No. | IC$_{50}$ [nM] |
| --- | --- |
| 1 | 28 |
| 2 | 50 |
| 3 | 11 |
| 4 | 36 |
| 5 | 18 |
| 6 | 33 |
| 7 | 13 |
| 8 | 4.5 |
| 9 | 27 |
| 10 | 18 |

TABLE 1-continued

| Example No. | IC$_{50}$ [nM] |
| --- | --- |
| 11 | 62 |
| 12 | 21 |
| 13 | 12 |
| 14 | 16 |
| 15 | 27 |
| 16 | 54 |
| 17 | 14 |
| 18 | 24 |
| 19 | 19 |
| 20 | 41 |
| 21 | 71 |

B-1b) Binding Studies on Human α1- and α2-Adrenergic Receptors

To prepare cell membranes with human $\alpha_1$- and $\alpha_2$-adrenergic receptors, CHO cells stably overexpressing $\alpha_1$- and $\alpha_2$-adrenergic receptors are lysed and then subjected to differential centrifugation. After lysis in binding buffer (50 mM tris(hydroxymethyl)aminomethane/1 N hydrochloric acid, 5 mM magnesium chloride, pH 7.4) using an Ultra Turrax (Jahnke & Kunkel, Werk), the homogenate is centrifuged at 1000 g and at 4° C. for 10 min. The resulting sediment is discarded and the supernatant is centrifuged at 20 000 g and at 4° C. for 30 min. The supernatant is discarded and the sediment is resuspended in binding buffer and stored at −70° C. until the binding test. For the binding test the radioligands $^3$H-MK-912 (2.2-3.2 TBq/mmol, PerkinElmer) (0.4 nM for $\alpha_{2C}$-adrRez and 1 nM for $\alpha_{2A}$-adrRez), 0.25 nM $^3$H-prazosin ($\alpha_{1AC}$-adrRez; 2.6-3.3 TBq/mmol, PerkinElmer), 0.25 nM $^3$H-rauwolscine ($\alpha_{2B}$-adrRez, 2.6-3.2 TBq/mmol, PerkinElmer) are incubated for 60 minutes with 5-20 μg cell membranes in binding buffer (total test volume 0.2 ml) in the presence of the test substances at 30° C. in 96-well filter plates (FC/B glass fibre, Multiscreen Millipore). The incubating is terminated by aspiration of the unbound radioactivity and the plates are then washed with binding buffer and subsequently dried at 40° C. for 1 hour. Liquid scintillator (Ultima Gold, PerkinElmer) is then added and the radioactivity that remained on the plates is measured in a liquid scintillation counter (Microbeta, Wallac). Non-specific binding is defined as radioactivity in the presence of 1-10 μM WB-4101 ($\alpha_{2C}$-adrRez and $\alpha_{2A}$-adrRez), prazosin ($\alpha_{2B}$-adrRez and $\alpha_{1AC}$-adrRez) (all from Sigma) and is generally <25% of the bound total radioactivity. The binding data (IC$_{50}$ and dissociation constant K$_i$) are determined using the program GraphPad Prism Version 4.0.

B-2) In Vivo Assays

B-2a) Relaxation Measurement on Isolated Rat Tail Arteries

Male Wistar rats (200-250 g) were euthanized with carbon dioxide. The tail artery is prepared and incubated in Krebs-Henseleit buffer at 4° C. for 17 h (composition in mmol/l: NaCl 112, KCl 5.9, CaCl$_2$ 2.0 MgCl$_2$ 1.2, NaH$_2$PO$_4$ 1.2, NaHCO$_3$ 25, glucose 11.5). The artery is cut into rings of length 2 mm, transferred to an organ bath filled with 5 ml of Krebs-Henseleit buffer and connected to a wire myograph (DMT, Denmark). The buffer is warmed to 27° C. and sparged with 95% 02, 5% CO$_2$. Before each experiment, the responsiveness of the preparation is tested by adding potassium-containing Krebs-Henseleit solution (50 mmol/l KCl). After an equilibration phase of 60 minutes, contraction of the vessel rings is induced with 30 nmol/l UK 14.304. The test substance is then added cumulatively in increasing concentration. Relaxation is shown as a reduction in the contraction induced by UK 14.304.

B-2b) Haemodynamics CHF Rat

Male old Wistar, ZDF/Crl-Lepr fa/fa, SHR-SP or Sprague Dawley rats (Charles River; 250-300 g) are anaesthetized with 5% isoflurane in an anaesthesis cage, intubated and then ventilated artificially (rate: 60 breaths/min; ratio inspiration to expiration: 50:50; positive end-expiratory pressure: 1 cm H$_2$O; tidal volume: 10 ml/kg of body weight; FIO$_2$: 0.5; 2% isoflurane). The body temperature is maintained at 37-38° C. by a heating mat. 0.05 mg/kg Temgesic is given s.c. as analgesic. For the haemodynamic measurement, the rats are tracheotomized and ventilated artificially (rate: 60 breaths/min; ratio inspiration to expiration: 50:50; positive end-expiratory pressure: 1 cm H$_2$O; tidal volume: 10 ml/kg of body weight; FIO$_2$: 0.5). Anaesthesia is maintained by inhalative isoflurane anaesthesia. The left-ventricular pressure is determined via the left carotid artery using a Millar microtip catheter (Millar SPR-320 2F). Systolic left-ventricular pressure (sLVP), end-diastolic ventricular pressure (LVEDP), contractility (+dPdt) and relaxation force (−dPdt) are determined as derived parameters. Following the haemodynamic measurements, the heart is removed and the ratio of right to left ventricle including septum is determined. Furthermore, plasma samples are obtained to determine plasma biomarkers and plasma substance concentrations.

B-2c) Measurement of Blood Flow and Blood Pressure in Rats

Wistar rats (Hsd Cpb:Wu) of a weight of 250-350 g or ZDF rats (ZDF/Crl-Lepr fa/fa) of a weight of 330-520 g are anaesthetized using 2.5% isoflurane in an oxygen/laughing gas mixture (40:60). To determine the blood flow in the carotid artery and the femoral artery, the anaesthetized rat is brought into a supine position, and the left carotid artery and the right femoral artery are then carefully exposed. Blood flow is measured by placing flow probes (Transonic Flowprobe) at the vessels. By introducing a PE50 artery catheter into the left femoral artery, blood pressure and heart rate are determined (Transducer Ref. 5203660: from Braun CH). The substances are administered as a bole injection or a continuous infusion via a venous catheter in the left femoral vein.

Following the preparation of the animals, there is a 5 min baseline interval. Infusion of the AR alpha2C antagonist is then started. In the steady state (32 min after the start of the experiment), the femoral flow is determined in relation (% difference) to the initial flow.

B-2d) Assay of Perfusion-Enhancing Substances (Haemodynamics)

To reduce perfusion, the right external iliac artery in anaesthetized (for example anaesthesia by inhalating isoflurane, enflurane) rats (for example ZDF/Crl-Lepr fa/fa) is ligated under sterile conditions. Depending on the degree of collateralization of the animals, it is additionally necessary to ligate the femoral artery to reduce perfusion. After the operation or else preventatively, the test animals are treated orally, intragastrically (uptake by stomach tube or through feed or drinking water), intraperitoneally, intravenously, intraarterially, intramuscularly, inhalatively or subcutaneously with the test substances. The test substances are administered enterally or parenterally, once or more than once per day over a period of up to 50 weeks, or administration is continuous via subcutaneously implanted osmotic mini-pumps (for example Alzet pumps). During the experiment, microperfusion and temperature of the lower extremities are documented. Here, under anaesthesia, a temperature-sensitive laser doppler probe (Periflux) is fastened with adhesive to the paws of the rats, allowing the measurement of microperfusion and skin temperature. Depending on the test protocol, samples such as blood (interim diagnostics) and other bodily fluids, urine or organs are removed to carry out further in vitro examinations, or, to document haemodynamics, blood pressure and heart rate are measured via a catheter in the carotid artery. At the end of the experiment, the animals are painlessly sacrificed.

B-2e) Assay of Perfusion-Enhancing Substances (Microcirculation)

In diabetic (ZDFfa/fa) and healthy rats (Wistar), a laser doppler probe was fastened under anaesthesia conditions (isoflurane anaesthesia) at the sole of the paw for measuring cutaneous microcirculation. The test animals were once treated orally with the test substances. During the experiment, microperfusion and temperature of the lower extremities were documented continuously. Here, a temperature-sensitive laser doppler probe (Periflux, 02C) was fastened with adhesive to the paws of the animals, allowing the measurement of microperfusion and skin temperature. The microcirculation measurement values were measured on both paws 30 min after oral administration of the test substance. From these data, means were calculated and compared to those of placebo-treated animals. What is shown are the minimum effective doses (MED) where the test substances showed a significantly improved microcirculation compared with placebo (vehicle=10% EtOH+30% PEG400+60% water for injection; 1 ml/kg) and the factor by which microcirculation is improved at this dose compared to placebo. Also stated is the MED for the significant increase of skin temperature (ttest).

Microcirculation data for adrenoreceptor $\alpha_{2C}$ receptor antagonist of the compound of Example 11 and for comparative substance ORM12741, an AR $\alpha$2C receptor antagonist from Orion, are shown in Table 2:

TABLE 2

| Example No. | MED [mg/kg] microcirculation | MED [mg/kg] skin temperature |
|---|---|---|
| 11 | 1 (2.4×) | 1 |
| ORM-12741 (Orion) | 0.1 (1.9×) | 0.01 |

B-2f) Assay of Perfusion-Enhancing Substances (Motoric Function) in the Treadmill Test To determine the motor function, the running behaviour of mice (for example eNOS knock out mice, wild-type mice C-57 Bl6 or ApoE knock out mice) is examined on treadmills. To get the mice used to using the treadmill voluntarily, 4-5 weeks before the start of the experiment the animals are put singly into cages with the treadmill and trained. 2 weeks before the start of the experiment, the movements of the mice on the treadmill are recorded by a computer-linked photo cell, and various running parameters such as, for example, daily distance run, individual distances covered, but also their temporal distribution over the day are determined According to their natural running behaviour, the animals are randomized into groups (8-12 animals) (control group, sham group and one or more substance groups). After the customization phase of 2 weeks, to reduce perfusion in the hind legs the femoral arteries on both sides are ligated under anaesthesia and under sterile conditions (for example anaesthesia by inhaling isoflurane). After the operation or else preventatively, the test animals are treated orally, intragastrically (uptake by stomach tube or through feed or drinking water), intraperitoneally, intravenously, intraarterially, intramuscularly, inhalatively or subcutaneously with the test substances. The test substances are administered enterally or parenterally, once or more than once per day over a period of up to 5 weeks, or administration is continuous via subcutaneously implanted osmotic mini-pumps. The running behaviour of the animals is monitored and recorded over a period of several weeks after the operation. At the end of the experiment, the animals are painlessly sacrificed. Depending on the test protocol, samples such as blood and other bodily fluids or organs are removed to carry out further in vitro examinations (S. Vogelsberger Neue Tiermodelle für die Indikation Claudicatio Intermittens [Novel animal models for the indication intermittent claudication] (pocket book), publisher: VVB Laufersweiler Verlag (March 2006), ISBN-10: 383595007X, ISBN-13: 978-3835950078).

B-2g) Assay of Perfusion-Enhancing Substances (Measurement of the Occlusion Pressure)

To reduce perfusion, the right external iliac artery in anaesthetized (for example anaesthesia by inhaling isoflurane) rats (for example ZDF rats) is ligated under sterile conditions. Depending on the degree of collateralization of the animals, it is additionally necessary to ligate the femoral artery to reduce perfusion. After the operation or else preventatively, the test animals are treated orally, intragastrically (uptake by stomach tube or through feed or drinking water), intraperitoneally, intravenously, intraarterially, intramuscularly, inhalatively or subcutaneously with the test substances. The test substances are administered enterally or parenterally, once or more than once per day over a period of up to 5 weeks, or administration is continuous via subcutaneously implanted osmotic mini-pumps (for example Alzet pumps). The occlusion pressures of the animals are measured before the operation (subsequent randomization) and once every week over a period of up to 2 months after the operation. Here, under anaesthesia an inflatable cuff is placed around the hind legs of the rats, and a temperature-adjustable laser doppler probe (Periflux) is fastened with adhesive on the paws. The cuffs are inflated until the laser doppler probes no longer measure any blood flow. The pressure in the cuffs is then continuously reduced and the pressure at which blood flow is detected again is determined. Depending on the test protocol, samples such as blood (interim diagnostics) and other bodily fluids or organs are removed for further in vitro examinations. At the end of the experiment, the animals are sacrificed painlessly (S. Vogelsberger Neue Tiermodelle far die Indikation Claudicatio Intermittens [New Animal Models for the Indication Intermittent Claudication] (pocket book), publisher: VVB Laufersweiler Verlag (March 2006), ISBN-10: 383595007X, ISBN-13: 978-3835950078.)

B-2h) Examination of Substances Affecting Wound Healing (Ulcer Model)

To induce a superficial wound, diabetic mice (db/db, i.e. BKS.Cg-m Dock7m+/+Leprdb/J mice) were anaesthetized with isoflurane. A continuous lesion (10 mm×10 mm) is placed on the left side of a skin area where the hairs have been removed and which has been disinfected. The animals are then randomized to the different treatment groups. In all groups, the wounds are covered with dressings (Systagenix Wound Management, UK). Daily (from day 1 after wound placing) the animals are treated by gavage (200 vehicle=10% EtOH+30% PEG400+60% water for injection) with the substances at the stated dosages. On days 4, 8, 12, 16 and 20, the animals are anaesthetized, the dressings are removed and the wound size is measured using digital photos. The photos are evaluated by an automatic calibrated planimetric process.

The results are shown as remaining wound sizes over the course of the experiment. To this end, all individual values are referenced in percent to the individual animal at the day the wound was placed.

B-2i) Examination of Substances Affecting Kidney Function

In animals suffering from acute or disease-related kidney damage (e.g. STZ rat, ZDF rat, ZDF rat with DOCA implant, UUO kidney damage model, glomerulonephritis model, diabetes, atherosclerosis), diuresis is carried out at regular intervals before or during continuous treatment with the test substances. The test animals are treated orally, intragastrically (uptake by stomach tube or through feed or drinking water), intraperitoneally, intravenously, intraarterially, intramuscularly, inhalatively or subcutaneously with the test substances. The test substances are administered enterally or parenterally, once or more than once per day, or administration is continuous via subcutaneously implanted osmotic mini-pumps (for example Alzet pumps). Over the entire duration of the test, plasma and urine parameters are determined.

B-2j) Haemodynamics in Anaesthetized Dogs

Healthy Mongrel® dogs (Marshall BioResources, Marshall Farms Inc; Clyde N.Y.; USA) or Mongrel® dogs suffering from heart failure of both sexes and having a weight of 25-35 kg are used. Anaesthesia is initiated by slow i.v. administration of 25 mg/kg sodium thiopental (Trapanal®) and 0.15 mg/kg alcuronium chloride (Alloferin®) and maintained during the experiment by means of a continuous infusion of 0.04 mg/kg*h fentanyl (Fentanyl®), 0.25 mg/kg*h droperidol (Dihydrobenzperidol®) and 15 µg/kg/h alcuronium chloride (Alloferin®). After intubation, the animals are ventilated by the ventilator at a constant respiratory volume such that an end-tidal $CO_2$ concentration of about 5% is achieved. Ventilation is performed with room air, enriched with about 30% oxygen (normoxia). To measure the haemodynamic parameters, a liquid-filled catheter is implanted into the femoral artery for measuring blood pressure. A Swan-Ganz® catheter having two lumens is introduced in a flow-directed manner via the jugular vein into the pulmonary artery (distal lumen for measuring the pressure in the pulmonary artery, proximal lumen for measuring the central vein pressure). Using a temperature sensor at the tip of the catheter, the continuous cardiac output (CCO) is determined. Blood flow is measured at various vascular beds such as the coronary artery, the carotid artery or the femoral artery by placing flow probes (Transonic Flowprobe) at the vessels in question. The pressure in the left ventricle is measured after introduction of a microtip catheter (Millar® Instruments) via the carotid artery into the left ventricle, and the dP/dt ratio as a measure of contractility is derived therefrom. Substances are administered i.v. via the femoral vein or intraduodenally as cumulative dose/activity curve (bolus or continuous infusion). The haemodynamic signals are recorded and evaluated by means of pressure transducers/amplifiers and PONEMAH® as data aquisition software.

To induce heart failure, a pacemaker is implanted into the dogs under sterile conditions. After induction of anaesthesia with pentobarbital-Na (15 to 30 mg kg$^{-1}$ i.v.) followed by intubation and subsequent ventilation (room air; Sulla 808, Dräger®, Germany), anaesthesia is maintained by continuous infusion of pentobarbital (1-5 mg kg$^{-1}$ h$^{-1}$) and fentanyl (10-40 µg kg$^{-1}$h$^{-1}$). A pacemaker cable (Setrox S60®, Biotronik, Germany) is implanted via an incision of the left jugular vein and placed in the right ventricle. The cable is connected to the pacemaker (Logos®, Biotronik, Germany), which is positioned in a small subcutaneous pocket between the shoulder blades. Ventricular pacing is started only 7 days after the surgical intervention, to obtain heart failure at a frequency of 220 beats/min over a period of 10-28 days.

B-2k) Determination of the Antidepressant Effect in the Rat-Forced-Swimming-Test Rats which are forced to swim in a narrow room from which there is no escape adapt after an initial phase of increased activity by adopting a characteristic rigid posture and only carry out those movements which are absolutely required to keep the head above the water. This immobility can be reduced by a number of clinically active antidepressants (e.g. Cryan J F, Markou A, Lucki I. Assessing antidepressant activity in rodents: recent developments and future needs. Trends Pharmacol. Sci. 2002; 23:238-245). The method used here is based on the protocol of Porsolt et al. (Porsolt R D, Anton G, Blavet N, Jalfre M. Behavioural despair in rats: a new model sensitive to antidepressant treatments. Eur. J. Pharmacol. 1978; 47379-91; and Porsolt R D, Brossard G, Hautbois C, Roux S. Rodent models of depression forced swimming and tail suspension behavioral despair tests in rats and mice. Curr. Protoc. Neurosci. 2001; Chapter 8:Unit 8.10A, 1-10) and De Vry et al. (De Vry J, Maurel S, Schreiber R, de Beun R, Jentzsch K R. Comparison of hypericum extracts with imipramine and fluoxetine in animal models of depression and alcoholism. Eur. Neuropsychopharmacology 1999; 9:461-468). In two sessions (training and test) at an interval of 24 h, the rats are forced to swim in a narrow cylinder filled with water from which there is no escape. The training session (duration 15 min) is carried out before the treatment with substance without recording the behaviour in order to familiarize the rats with the 5-minute test session 24 h later. During both sessions, the rats are individually placed into the cylinders filled with water, which are optically separated from one another. After the session, the rats are removed from the water and dried. About 24, 5 and 1 h prior to the test session, the rats are treated with test substance or vehicle solution; the first administration takes place immediately after the training session. 3 substance administrations prior to the test session lead to more stable pharmacological results than a single administration. The test sessions are recorded electronically using a surveillance video camera and, after storage, analysed off-line using a computer. For each animal, the behaviour is analysed by 3-4 independent observers who score the total time of immobility in seconds over the 5-minute test session.

Passive behaviour or immobility is defined as a rat which drifts in the water in an upright position and makes only small movements to keep the head above the water or to maintain its body in a balanced stable position. In contrast, active behaviour is characterized by active swimming movements, e.g. forceful movements of front or hind legs and/or tail, climbing or diving.

For each animal and treatment group, the mean of the duration of immobility determined by the observers is calculated. Differences in the duration of immobility between the groups are examined statistically by ANOVA or a suitable non-parametric test with $p<0.05$ as significance level.

B-21) Radiotelemetric Measurement of Blood Pressure and Heart Rate of Conscious Rats A commercially available telemetry system from Data Sciences International DSI, USA, is employed for the measurements on conscious rats described below. The system consists of 3 main components: (1) implantable transmitters (Physiotel® telemetry transmitter), (2) receivers (Physiotel® receiver), which are linked via a multiplexer (DSI Data Exchange Matrix) to a (3) data acquisition computer. The telemetry system makes it possible to continuously record blood pressure, heart rate and body motion of conscious animals in their usual habitat.

The studies are conducted on adult female Wistar rats with a body weight of >200 g. After transmitter implantation, the experimental animals are housed singly in type III Makrolon® cages. They have free access to standard feed and water. The day/night rhythm in the test laboratory is set by changing the illumination of the room.

Transmitter Implantation:

The telemetry transmitters used (PA-C40, DSI) are surgically implanted under aseptic conditions in the experimental animals at least 14 days before the first experimental use.

For the implantation, the fasted animals are anaesthetized with isoflurane (IsoFlo®, Abbott, initiation 5%, maintenance 2%) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (Vetbond™, 3M). The transmitter housing is fixed intraperitoneally to the abdominal wall muscle, and the wound is closed layer by layer. Post-operatively, an antibiotic (Ursocyclin® 10%, 60 mg/kg s.c., 0.06 ml/100 g body weight, Serumwerk Bernburg AG, Germany) for infection prophylaxis and an analgesic (Rimadyl®, 4 mg/kg s.c., Pfizer, Germany) are administered.

Substances and Solutions:

Unless stated otherwise, the substances to be studied are administered orally to a group of animals in each case (n=6). In accordance with an administration volume of 2 ml/kg of body weight, the test substances are dissolved in suitable solvent mixtures. A solvent-treated group of animals is used as control.

Experimental Outline:

The telemetry measuring system is configured for 24 animals.

Each of the instrumented rats living in the system is assigned a separate receiving antenna (RPC-1 Receiver, DSI). The implanted senders can be activated externally via an installed magnetic switch and are switched to transmission during the pre-run of the experiment. The signals emitted can be detected online by a data acquisition system (Dataquest™ A.R.T. for Windows, DSI) and processed accordingly.

In the standard procedure, the following are measured for 10-second periods in each case: (1) systolic blood pressure (SBP), (2) diastolic blood pressure (DBP), (3) mean arterial pressure (MAP), (4) heart rate (HR) and (5) activity (ACT). These parameters are measured over 24 hours after administration.

The acquisition of measurements is repeated under computer control at 5-minute intervals. The source data obtained as absolute values are corrected in the diagram with the currently measured barometric pressure (Ambient Pressure Reference Monitor, APR-1, DSI).

Evaluation:

After the end of the experiment, the acquired individual data are sorted using the analysis software (Dataquest™ A.R.T. 4.1 Analysis). The blank value is taken to be the mean of the pre-run (i.e. before substance administration) (4 absolute values) and this is compared to the absolute value of the measurement, giving the deviation in %. The data are smoothed over a presettable period by determination of the means (15 minute mean).

LITERATURE

K. Witte, K. Hu, J. Swiatek, C. Müssig, G. Ertl and B. Lemmer, Experimental heart failure in rats: effects on cardiovascular circadian rhythms and on myocardial β-adrenergic signaling, Cardiovasc. Res. 47 (2): 203-405, 2000.

C) WORKING EXAMPLES FOR PHARMACEUTICAL COMPOSITIONS

The substances according to the invention can be converted to pharmaceutical preparations as follows:

Tablet:

Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.

Production:

The mixture of the compound of Example 1, lactose and starch is granulated with a 5% strength solution (m/m) of the PVP in water. After drying, the granules are mixed with the magnesium stearate for 5 min. This mixture is compressed in a conventional tabletting press (see above for format of the tablet).

Oral Suspension:

Composition:

1000 mg of the compound of Example 1, 1000 mg of ethanol (96%), 400 mg of Rhodigel (xanthan gum) (from FMC, USA) and 99 g of water.

10 ml of oral suspension correspond to a single dose of 100 mg of the compound of the invention.

Production:

The Rhodigel is suspended in ethanol, and the compound of Example 1 is added to the suspension. The water is added while stirring. The mixture is stirred for approx. 6 h until the Rhodigel has finished swelling.

Intravenously Administrable Solution:

Composition:

1 mg of the compound of Example 1, 15 g of polyethylene glycol 400 and 250 g of water for injection purposes.

Production:

The compound of Example 1 is dissolved together with polyethylene glycol 400 by stirring in the water. The solution is sterilized by filtration (pore diameter 0.22 μm) and dispensed under aseptic conditions into heat-sterilized infusion bottles. The latter are closed with infusion stoppers and crimped caps.

The invention claimed is:

1. A compound of the formula (I)

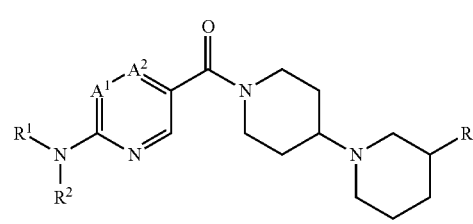

in which
$R^1$ represents $C_2$-$C_6$-alkyl or benzyl,
  where alkyl may be substituted by 1 to 2 substituents independently of one another selected from the group consisting of hydroxy, $C_1$-$C_4$-alkoxy, $C_1$-$C_4$-cycloalkyloxy and aminocarbonyloxo,
  where benzyl may be substituted by 1 or 2 substituents independently of one another selected from halogen;
and
$R^2$ is selected from the group consisting of hydrogen and $C_1$-$C_4$-alkyl;
or
$R^1$ and $R^2$ together with the nitrogen atom to which they are attached form a 4- to 7-membered N-heterocycle,
  where the N-heterocycle may be substituted by 1 to 3 substituents independently of one another selected from the group consisting of $C_1$-$C_4$-alkyl, $C_1$-$C_4$-alkoxy, $C_1$-$C_4$-alkoxy-$C_1$-$C_4$-alkyl, halogen, oxo, hydroxy, monofluoromethyl, difluoromethyl, trifluoromethyl, hydroxycarbonyl, tert-butoxycarbonyl and aminocarbonyl,
  or
  where the N-heterocycle may have two substituents which, together with the carbon atom of the N-heterocycle to which they are jointly attached, form a 4- to 6-membered heterocycle,
    where this N-heterocycle for its part may be substituted by 1 to 3 substituents independently of one another selected from the group consisting of oxo, methyl and ethyl;
$R^3$ represents $C_1$-$C_3$-alkyl, $C_1$-$C_3$-alkoxycarbonyl, $C_3$-$C_6$-cycloalkyl, $C_3$-$C_6$-cycloalkyl-$C_1$-$C_3$-alkoxy, $C_3$-$C_6$-cycloalkoxy, trifluoromethoxy-$C_1$-$C_4$-alkoxy, 5- or 6-membered heteroaryl or —OCONR$^4$R$^5$,
  where alkyl may be substituted by a substituent selected from the group consisting of $C_1$-$C_4$-alkoxy, $C_3$-$C_6$-cycloalkoxy, trifluoromethoxy and phenoxy,
    in which this phenoxy for its part may be substituted by 1 to 3 substituents independently of one another selected from the group consisting of halogen,
  and
  where heteroaryl may be substituted by 1 to 3 substituents independently of one another selected from the group consisting of $C_1$-$C_4$-alkyl and $C_3$-$C_6$-cycloalkyl,
    where this alkyl for its part may be substituted by a substituent selected from the group consisting of $C_1$-$C_3$-alkoxy and $C_3$-$C_6$-cycloalkyl,
$R^4$ represents $C_1$-$C_4$-alkyl,
$R^5$ represents hydrogen or $C_1$-$C_4$-alkyl,
or
$R^4$ and $R^5$ together with the nitrogen atom to which they are attached form a pyrrolidinyl ring,
$A^1$ represents CH and $A^2$ represents N;
or
$A^1$ represents N and $A^2$ represents CH;
or
$A^1$ and $A^2$ represent CH;
or one of the salts thereof, solvates thereof or solvates of the salts thereof.

2. The compound of the formula (I) according to claim 1 in which
$R^1$ represents $C_2$-$C_6$-alkyl or benzyl,
  where alkyl may be substituted by 1 to 2 substituents independently of one another selected from the group consisting of hydroxy, $C_1$-$C_4$-alkoxy and aminocarbonyloxo,
  where benzyl may be substituted by 1 or 2 substituents independently of one another selected from fluorine and chlorine;
and
$R^2$ is selected from the group consisting of hydrogen and $C_1$-$C_4$-alkyl;
or
$R^1$ and $R^2$ together with the nitrogen atom to which they are attached form an azetidine, pyrrolidine, piperidine, azepane, piperazine, morpholine, thiomorpholine, 1-oxidothiomorpholine or 1,1-dioxidothiomorpholine,
  where azetidine, pyrrolidine, piperidine, azepane, piperazine, morpholine, thiomorpholine, 1-oxidothiomorpholine and 1,1-dioxidothiomorpholine may be substituted by 1 to 3 substituents independently of one another selected from the group consisting of $C_1$-$C_2$-alkyl, $C_1$-$C_2$-alkoxy, $C_1$-$C_2$-alkoxy-$C_1$-$C_2$-alkyl and halogen,
  or
  where azetidine, pyrrolidine, piperidine, azepane, piperazine, morpholine, thiomorpholine, 1-oxidothiomorpholine and 1,1-dioxidothiomorpholine may have two substituents which together with the carbon atom of the azetidine, pyrrolidine, piperidine, azepane, piperazine, morpholine, thiomorpholine, 1-oxidothiomorpholine or 1,1-dioxidothiomorpholine to which they are jointly attached form an azetidine or oxetane,
    where this azetidine or oxetane for its part may be substituted by 1 to 2 substituents independently of one another selected from the group consisting of 3-methyl and 3-ethyl,
$R^3$ is selected from the group consisting of $C_1$-$C_4$-alkyl and $C_3$-$C_6$-cycloalkyl-$C_1$-$C_4$-alkoxy;
$A^1$ represents CH and $A^2$ represents N;
or
$A^1$ represents N and $A^2$ represents CH;
or
$A^1$ and $A^2$ represent CH;
or one of the salts thereof, solvates thereof or solvates of the salts thereof.

3. The compound of the formula (I) according to claim 1 in which
$R^1$ represents $C_2$-$C_4$-alkyl or benzyl,
  where alkyl may be substituted by 1 to 2 substituents independently of one another selected from the group consisting of hydroxy, $C_1$-$C_2$-alkoxy and aminocarbonyloxo,
  where benzyl may be substituted by 1 or 2 fluorine substituents,
and
$R^2$ represents hydrogen or $C_1$-$C_2$-alkyl;
or
$R^1$ and $R^2$ together with the nitrogen atom to which they are attached form an azetidine, pyrrolidine, piperidine, morpholine or 1,1-dioxidothiomorpholine,
  where azetidine, pyrrolidine, piperidine, morpholine or 1,1-dioxidothiomorpholine may be substituted by 1 to 2 substituents selected independently from the group consisting of methyl, methoxy, methoxymethyl and fluorine,
  or
  where azetidine, pyrrolidine, piperidine, morpholine and 1,1-dioxidothiomorpholine may have two substituents which together with the carbon atom of the azetidine, pyrrolidine, piperidine, morpholine or 1,1- dioxidothiomorpholine to which they are jointly attached form an azetidine or oxetane,
where this azetidine or oxetane for its part may be substituted by 1 to 2 substituents independently of one another selected from the group consisting of 3-methyl and 3-ethyl,
$R^3$ is selected from the group consisting of methyl and cyclopropylmethoxy;
$A^1$ represents CH and $A^2$ represents N;
or
$A^1$ represents N and $A^2$ represents CH;
or
$A^1$ and $A^2$ represent CH;
or one of the salts thereof, solvates thereof or solvates of the salts thereof.

4. The compound of the formula (I) according to claim 1 in which
$R^1$ is selected from the group consisting of methoxyethyl, hydroxy-sec-butyl, sec-butyl carbamate, methoxy-sec-butyl and benzyl,
where benzyl may be substituted by 1 to 2 fluorine substituents;
and
$R^2$ represents hydrogen or methyl;
or
$R^1$ and $R^2$ together with the nitrogen atom to which they are attached form an azetidine, pyrrolidine, piperidine, morpholine or 1,1-dioxidothiomorpholine,
where azetidine, pyrrolidine, piperidine, morpholine or 1,1-dioxidothiomorpholine may be substituted by 1 to 2 substituents selected independently from the group consisting of methyl, methoxy, methoxymethyl and fluorine,
or
where azetidine may have two substituents which, together with the carbon atom of the azetidine to which they are jointly attached, form an oxetane,
$R^3$ is selected from the group consisting of methyl and cyclopropylmethoxy;
$A^1$ is CH;
and
$A^2$ represents N;
or
$A^1$ represents N;
and
$A^2$ represents CH;
or
$A^1$ and $A^2$ represent CH;
or one of the salts thereof, solvates thereof or solvates of the salts thereof.

5. A method of making the compound of the formula (I) of claim 1 or the salts thereof, the solvates thereof or the solvates of the salts thereof, where
[A] compounds of the formula (II)

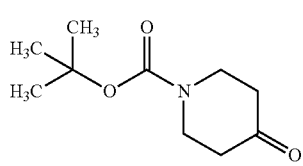

are reacted with compounds of the formula (III)

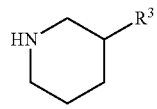

in which $R^3$ has the meanings given above,
in the presence of a reducing agent to give compounds of the formula (IV)

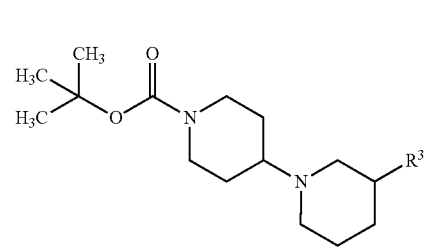

in which $R^3$ has the meanings given above,
or
[B] compounds of the formula (IV)

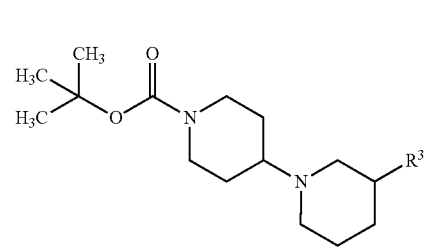

in which $R^3$ has the meanings given above,
are reacted in the presence of an acid to give compounds of the formula (V)

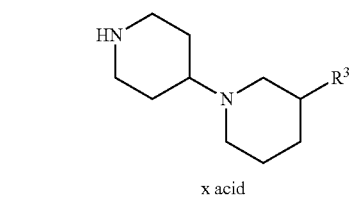

in which $R^3$ has the meanings given above,
or
[C] compounds of the formula (VI)

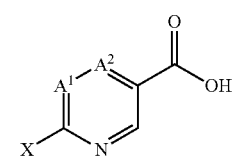

in which X represents halogen, preferably fluorine, chlorine or bromine, or sulphonylmethane, in which A¹ represents CH and A² represents CH or N, are reacted with compounds of the formula (VII)

(VII)

$R^1\underset{}{\overset{H}{N}}R^2$ in which R¹ and R² have the meanings given above, to give compounds of the formula (VIII)

(VIII)

[structure: pyrimidine/pyridine ring with A¹, A² positions, NR¹R² substituent, and C(=O)OH group]

in which A¹ represents CH, A² represents CH or N and R¹ and R² have the meanings given above,
or
[D] compounds of the formula (VIII)

(VIII)

[structure: same as above]

in which R', R², A¹ and A² have the meanings given above,
are reacted with compounds of the formula (V)

(V)

[structure: HN-piperidine-N-piperidine-R³]

x acid in which R³ has the meanings given above,
in the presence of a dehydrating agent to give compounds of the formula (I) or
[E] compounds of the formula (VI)

(VI)

[structure: ring with A¹, A², X substituent, and C(=O)OH]

in which X represents halogen, preferably fluorine, chlorine or bromine, or sulphonylmethane, A¹ and A² have the meanings given above, with the proviso that, if X represents halogen, A¹ represents CH and A² represents CH or N,
are reacted with compounds of the formula (V)

(V)

[structure: HN-piperidine-N-piperidine-R³]

x acid in which R³ has the meanings given above,
in the presence of a dehydrating agent to give compounds of the formula (IX)

(IX)

[structure: ring with A¹, A², X, and C(=O)-N-piperidine-N-piperidine-R³]

in which R³, A¹ and A² have the meanings given above and
in which X represents halogen, preferably fluorine, chlorine or bromine, or sulphonylmethane,
with the proviso that, if X represents halogen, A¹ represents CH and A² represents CH or N,
or
[F] compounds of the formula (IX)

(IX)

[structure: same as above]

in which R³, A¹ and A² have the meanings given above and
in which X represents halogen, preferably fluorine, chlorine or bromine, or sulphonyl methane,
with the proviso that, if X represents halogen, A¹ represents CH and A² represents CH or N,
are reacted with compounds of the formula (VII)

(VII)

$R^1\underset{}{\overset{H}{N}}R^2$ in which R¹ and R² have the meanings given above,
to give compounds of the formula (I) in which R¹, R², R³, A¹ and A² have the meanings given above, with the proviso that, if X in formula (IX) represents halogen, A¹ represents CH and A² represents CH or N, or

[G] compounds of the formula (X)

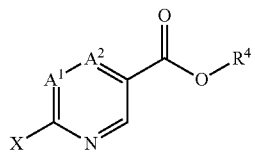

in which
X represents halogen, preferably chlorine, fluorine or bromine, or sulphonylmethane,
R⁴ represents C₁-C₄-alkyl, preferably methyl or ethyl, and
A¹ and A² have the meanings given above,
are reacted in the presence of a base with compounds of the formula (VII)

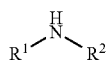

in which R¹ and R² have the meanings given above,
to give compounds of the formula (XI)

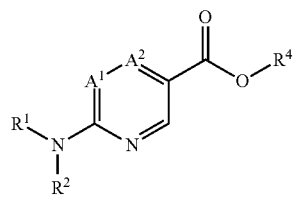

R⁴ represents C₁-C₄-alkyl, preferably methyl or ethyl, and
in which R¹, R², A¹ and A² have the meanings given above,
or

[H] compounds of the formula (VIII)

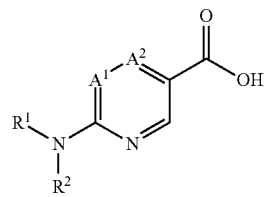

in which R', R², A¹ and A² have the meanings given above, are reacted with compounds of the formula (V)

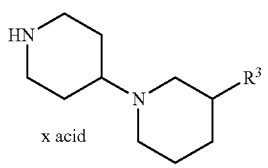

in which R³ has the meanings given above,
in the presence of a dehydrating agent to give compounds of the formula (I) or

[I] compounds of the formula (VIII)

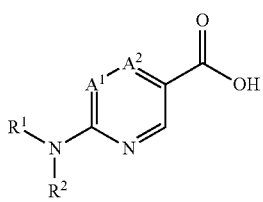

in which R¹, R², A¹ and A² have the meanings given above,
are reacted with piperidin-4-one to give compounds of the formula (XII)

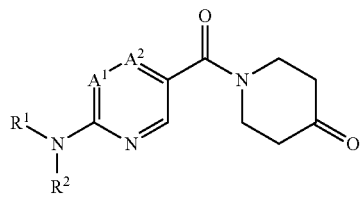

in which R¹, R², A¹ and A² have the meanings given above,
or

[J] compounds of the formula (XII)

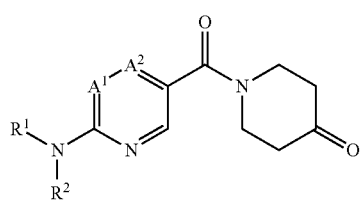

in which R', R², A¹ and A² have the meanings given above,
are reacted with compounds of the formula (III)

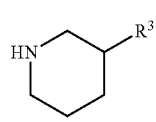

in which R³ has the meanings given above,
in the presence of a reducing agent to give compounds of the formula (I).

6. A compound of the formula (XI) or (VIII)

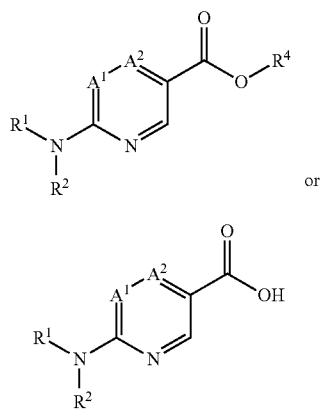

in which
R¹ represents benzyl, where benzyl is substituted by 2 fluorine substituents;
and
R² represents methyl;
R⁴ represents $C_1$-$C_4$-alkyl, preferably methyl or ethyl;
A¹ and A² represent CH;
and the salts thereof, the solvates thereof and the solvates of the salts thereof.

7. A method of antagonizing an adrenoreceptor in an individual that suffers from diabetic ulcers on the extremities comprising administering an effective amount of the compound of claim 1.

8. A medicament comprising the compound of claim 1 in combination with one or more inert non-toxic pharmaceutically suitable auxiliaries.

9. A medicament comprising the compound of claim 1 in combination with one or more further active compounds selected from the group consisting of lipid metabolism-modulating active compounds, antidiabetics, hypotensive agents, agents which lower the sympathetic tone, perfusion-enhancing and/or antithrombotic agents and also antioxidants, aldosterone and mineralocorticoid receptor antagonists, vasopressin receptor antagonists, organic nitrates and NO donors, IP receptor agonists, positive inotropic compounds, calcium sensitizers, ACE inhibitors, cGMP- and cAMP-modulating compounds, natriuretic peptides, NO-independent stimulators of guanylate cyclase, NO-independent activators of guanylate cyclase, inhibitors of human neutrophil elastase, compounds which inhibit the signal transduction cascade, compounds which modulate the energy metabolism of the heart, chemokine receptor antagonists, p38 kinase inhibitors, NPY agonists, orexin agonists, anorectics, PAF-AH inhibitors, antiphlogistics, analgesics, antidepressants and other psychopharmaceuticals.

10. A method of antagonizing an adrenoreceptor in an individual that suffers from at least one of primary and secondary forms of diabetic microangiopathies, diabetic wounds, diabetic ulcers on the extremities, diabetic foot ulcers, diabetic retinopathy, diabetic nephropathy, diabetic erectile dysfunction, diabetic heart failure, diabetic coronary microvascular heart disorders, peripheral and cardiac vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies comprising administering an effective amount of the medicament of claim 8.

11. A method of antagonizing an adrenoreceptor in an individual that suffers from at least one of primary and secondary forms of diabetic microangiopathies, diabetic wounds, diabetic ulcers on the extremities, diabetic foot ulcers, diabetic retinopathy, diabetic nephropathy, diabetic erectile dysfunction, diabetic heart failure, diabetic coronary microvascular heart disorders, peripheral and cardiac vascular disorders, thromboembolic disorders and ischaemias, peripheral circulatory disturbances, Raynaud's phenomenon, CREST syndrome, microcirculatory disturbances, intermittent claudication, and peripheral and autonomous neuropathies, in humans and animals comprising administering an effective amount of the compound of claim 1.

12. A method of antagonizing an adrenoreceptor in an individual that suffers from diabetic ulcers on the extremities comprising administering the medicament of claim 8.

13. A method of antagonizing an adrenoreceptor in an individual that suffers from diabetic disorders or diabetic diseases using the compound of claim 1.

14. A method of antagonizing an adrenoreceptor in an individual that suffers from diabetic disorders or diabetic diseases by administration of an effective amount of the medicament of claim 8.

15. A medicament comprising the compound of claim 1 in combination with one or more further active compounds selected from the group consisting of rivaroxaban, iloprost, and inhibitors of phosphodiesterases (PDE) 1, 2, 3, 4, and/or 5.

16. A method of antagonizing an adrenoreceptor in an individual that suffers from peripheral occlusive disease comprising administering an effective amount of the compound of claim 1.

17. A method of antagonizing an adrenoreceptor in an individual that suffers from at least one of peripheral and cardiac vascular disorders, peripheral circulatory disturbances, or intermittent claudication comprising administering an effective amount of the compound of claim 1.

18. A method of antagonizing an adrenoreceptor in an individual that suffers from at least one of peripheral and cardiac vascular disorders, peripheral circulatory disturbances, or intermittent claudication comprising administering an effective amount of the medicament of claim 8.

19. A method of antagonizing an adrenoreceptor in an individual that suffers from peripheral occlusive disease comprising administering an effective amount of the medicament of claim 8.

* * * * *